(12) United States Patent
Yoshikane et al.

(10) Patent No.: US 11,970,549 B2
(45) Date of Patent: Apr. 30, 2024

(54) ANTIBODY CAPABLE OF BINDING SPECIFICALLY TO 5' TO 3' EXONUCLEASE ACTIVE DOMAIN OF DNA POLYMERASE

(71) Applicants: TOYOBO CO., LTD., Osaka (JP); NATIONAL UNIVERSITY CORPORATION UNIVERSITY OF TOYAMA, Toyama (JP)

(72) Inventors: Takafumi Yoshikane, Tsuruga (JP); Nobuyuki Kurosawa, Toyama (JP); Masaharu Isobe, Toyama (JP)

(73) Assignees: TOYOBO CO., LTD., Osaka (JP); NATIONAL UNIVERSITY CORPORATION UNIVERSITY OF TOYAMA, Toyama (JP)

( * ) Notice: Subject to any disclaimer, the term of this patent is extended or adjusted under 35 U.S.C. 154(b) by 0 days.

(21) Appl. No.: 17/996,601

(22) PCT Filed: Dec. 10, 2021

(86) PCT No.: PCT/JP2021/045700
§ 371 (c)(1),
(2) Date: Oct. 19, 2022

(87) PCT Pub. No.: WO2022/124418
PCT Pub. Date: Jun. 16, 2022

(65) Prior Publication Data
US 2023/0140801 A1    May 4, 2023

(30) Foreign Application Priority Data

Dec. 11, 2020  (JP) ................................ 2020-206269
Jun. 14, 2021  (JP) ................................ 2021-098632

(51) Int. Cl.
*C07K 16/40* (2006.01)
(52) U.S. Cl.
CPC ........ *C07K 16/40* (2013.01); *C07K 2317/565* (2013.01)
(58) Field of Classification Search
None
See application file for complete search history.

(56) References Cited

U.S. PATENT DOCUMENTS

2010/0143898 A1    6/2010  Kutyavin

FOREIGN PATENT DOCUMENTS

| CN | 112409490 A | 2/2021 |
|---|---|---|
| JP | 2012-520080 A | 9/2012 |
| JP | 2017-163904 A | 9/2017 |
| WO | WO 2010/105074 A1 | 9/2010 |
| WO | WO 2016/136324 A1 | 9/2016 |

OTHER PUBLICATIONS

Schroeder et al. J Allergy Clin Immunol 2010, 125:S41-S52.*
Lloyd et al. Protein Engineering, Design & Selection 2009, 22:159-168.*
Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*
Daiss et al., "Topographical Characterization of the DNA Polymerase from *Thermus aquaticus*—Defining Groups of Inhibitor mAbs by Epitope Mapping and Functional Analysis Using Surface Plasmon Resonance," *J. Immunol. Methods*, 183(1): 15-26 (1995).
Holland et al., "Detection of Specific Polymerase Chain Reaction Product by Utilizing the 5'→3' Exonuclease Activity of *Thermus aquaticus* DNA Polymerase," *Proc. Natl. Acad. Sci. USA*, 88(16): 7276-7280 (1991).
Kim et al., "Mutagenesis of the Positively Charged Conserved Residues in the 5' Exonuclease Domain of Taq DNA Polymerase," *Mol. Cells*, 7(4): 468-472 (1997).
Kim et al., "Roles of the Conserved Carboxylic Residues in the Active-Site of 5'-3' Exonuclease of Taq DNA Polymerase," *J. Microbiol. Biotechnol.*, 9(4): 381-385 (1999).
Lyamichev et al., "Comparison of the 5' Nuclease Activities of Taq DNA Polymerase and Its Isolated Nuclease Domain," *Proc. Natl. Acad. Sci. USA*, 96(11): 6143-6148 (1999).
Lyamichev et al., "Structure-Specific Endonucleolytic Cleavage of Nucleic Acids by Eubacterial DNA Polymerases," *Science.*, 260(5109): 778-783 (1993).
Ruscitti et al., "Selective Immunoneutralization of the Multiple Activities of *Escherichia coli* DNA Polymerase I Supports the Model for Separate Active Sites and Indicates a Complex 5' to 3' Exonuclease," *J. Biol. Chem.*, 267(24): 16806-16811 (1992).
Japan Patent Office, Notice of Reasons for Refusal in Japanese Patent Application No. 2021-098787 (dated Aug. 17, 2021).
Japan Patent Office, Decision of Refusal in Japanese Patent Application No. 2021-098787 (dated Dec. 14, 2021).
Japan Patent Office, Notice of Reasons for Refusal in Japanese Patent Application No. 2021-098787 (dated Jun. 7, 2022).
Japan Patent Office, International Search Report in International Patent Application No. PCT/JP2021/045700 (dated Feb. 22, 2022).
Sela-Culang et al., "The Structural Basis of Antibody-Antigen Recognition," *Front. Immunol.*, 4: 302 (2013).

(Continued)

*Primary Examiner* — Sharon X Wen
(74) *Attorney, Agent, or Firm* — Leydig, Voit & Mayer, Ltd.

(57) ABSTRACT

The invention provides an antibody that specifically binds to a 5' to 3' exonuclease domain of a DNA polymerase, or a fragment thereof. The antibody inhibits the 5' to 3' exonuclease activity of a DNA polymerase, or a fragment thereof.

10 Claims, No Drawings
Specification includes a Sequence Listing.

(56) References Cited

OTHER PUBLICATIONS

Zemlin, et al., "Expressed Murine and Human CDR-H3 Intervals of Equal Length Exhibit Distinct Repertoires that Differ in their Amino Acid Composition and Predicted Range of Structures," *J. Mol. Biol.*, 334(4): 733-749 (2003).
Japan Patent Office, Office Action in Japanese Patent Application No. 2022-568364 (Feb. 20, 2024).

* cited by examiner

SEQUENCE LISTING

<160> NUMBER OF SEQ ID NOS: 95

<210> SEQ ID NO 1
<211> LENGTH: 290
<212> TYPE: PRT
<213> ORGANISM: Thermus aquaticus

<400> SEQUENCE: 1

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser
    290
```

<210> SEQ ID NO 2
<211> LENGTH: 292
<212> TYPE: PRT
<213> ORGANISM: Thermus thermophilus

<400> SEQUENCE: 2

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
```

```
                    20                  25                  30
Leu Thr Thr Ser Arg Gly Glu Pro Val Gln Ala Val Tyr Gly Phe Ala
                35                  40                  45
Lys Ser Leu Leu Lys Ala Leu Lys Glu Asp Gly Tyr Lys Ala Val Phe
            50                  55                  60
Val Val Phe Asp Ala Lys Ala Pro Ser Phe Arg His Glu Ala Tyr Glu
65                  70                  75                  80
Ala Tyr Lys Ala Gly Arg Ala Pro Thr Pro Glu Asp Phe Pro Arg Gln
                85                  90                  95
Leu Ala Leu Ile Lys Glu Leu Val Asp Leu Leu Gly Phe Thr Arg Leu
            100                 105                 110
Glu Val Pro Gly Tyr Glu Ala Asp Asp Val Leu Ala Thr Leu Ala Lys
        115                 120                 125
Lys Ala Glu Lys Glu Gly Tyr Glu Val Arg Ile Leu Thr Ala Asp Arg
    130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Arg
                165                 170                 175
Pro Glu Gln Trp Val Asp Phe Arg Ala Leu Val Gly Asp Pro Ser Asp
            180                 185                 190
Asn Leu Pro Gly Val Lys Gly Ile Gly Glu Lys Thr Ala Leu Lys Leu
        195                 200                 205
Leu Lys Glu Trp Gly Ser Leu Glu Asn Leu Leu Lys Asn Leu Asp Arg
    210                 215                 220
Val Lys Pro Glu Asn Val Arg Glu Lys Ile Lys Ala His Leu Glu Asp
225                 230                 235                 240
Leu Arg Leu Ser Leu Glu Leu Ser Arg Val Arg Thr Asp Leu Pro Leu
                245                 250                 255
Glu Val Asp Leu Ala Gln Gly Arg Glu Pro Asp Arg Glu Gly Leu Arg
            260                 265                 270
Ala Phe Leu Glu Arg Leu Glu Phe Gly Ser Leu Leu His Glu Phe Gly
        275                 280                 285
Leu Leu Glu Ala
    290

<210> SEQ ID NO 3
<211> LENGTH: 292
<212> TYPE: PRT
<213> ORGANISM: Thermus sp. Z05

<400> SEQUENCE: 3

Met Lys Ala Met Leu Pro Leu Phe Glu Pro Lys Gly Arg Val Leu Leu
1               5                   10                  15
Val Asp Gly His His Leu Ala Tyr Arg Thr Phe Phe Ala Leu Lys Gly
            20                  25                  30
Leu Thr Thr Ser Arg Gly Glu Pro Val Gln Ala Val Tyr Gly Phe Ala
                35                  40                  45
Lys Ser Leu Leu Lys Ala Leu Lys Glu Asp Gly Tyr Lys Ala Val Phe
            50                  55                  60
Val Val Phe Asp Ala Lys Ala Pro Ser Phe Arg His Glu Ala Tyr Glu
65                  70                  75                  80
Ala Tyr Lys Ala Gly Arg Ala Pro Thr Pro Glu Asp Phe Pro Arg Gln
                85                  90                  95
```

```
Leu Ala Leu Ile Lys Glu Leu Val Asp Leu Leu Gly Phe Thr Arg Leu
                100                 105                 110

Glu Val Pro Gly Phe Glu Ala Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala
    290

<210> SEQ ID NO 4
<211> LENGTH: 8
<212> TYPE: PRT
<213> ORGANISM: Guinea pig

<400> SEQUENCE: 4

Gly Phe Thr Phe Asp Asp Tyr Gly
1               5

<210> SEQ ID NO 5
<211> LENGTH: 8
<212> TYPE: PRT
<213> ORGANISM: Guinea pig

<400> SEQUENCE: 5

Gly Phe Thr Phe Ser Asn Tyr Tyr
1               5

<210> SEQ ID NO 6
<211> LENGTH: 8
<212> TYPE: PRT
<213> ORGANISM: Guinea pig

<400> SEQUENCE: 6

Gly Phe Thr Phe Asn Asn Tyr Tyr
1               5

<210> SEQ ID NO 7
<211> LENGTH: 8
<212> TYPE: PRT
<213> ORGANISM: Guinea pig

<400> SEQUENCE: 7
```

```
Gly Phe Thr Phe Ser Ser Tyr Tyr
1               5

<210> SEQ ID NO 8
<211> LENGTH: 8
<212> TYPE: PRT
<213> ORGANISM: Guinea pig

<400> SEQUENCE: 8

Gly Phe Thr Phe Ser Lys Trp Tyr
1               5

<210> SEQ ID NO 9
<211> LENGTH: 8
<212> TYPE: PRT
<213> ORGANISM: Guinea pig

<400> SEQUENCE: 9

Gly Phe Thr Phe Ser His Tyr Tyr
1               5

<210> SEQ ID NO 10
<211> LENGTH: 8
<212> TYPE: PRT
<213> ORGANISM: Guinea pig

<400> SEQUENCE: 10

Gly Phe Thr Phe Ser Asn Tyr Trp
1               5

<210> SEQ ID NO 11
<211> LENGTH: 8
<212> TYPE: PRT
<213> ORGANISM: Guinea pig

<400> SEQUENCE: 11

Gly Phe Thr Phe Ser Ser Tyr Gly
1               5

<210> SEQ ID NO 12
<211> LENGTH: 8
<212> TYPE: PRT
<213> ORGANISM: Guinea pig

<400> SEQUENCE: 12

Ile Ser Leu Ser Gly Gly Ser Ser
1               5

<210> SEQ ID NO 13
<211> LENGTH: 8
<212> TYPE: PRT
<213> ORGANISM: Guinea pig

<400> SEQUENCE: 13

Ile Ser Asn Thr Gly Gly Ser Thr
1               5

<210> SEQ ID NO 14
<211> LENGTH: 8
<212> TYPE: PRT
<213> ORGANISM: Guinea pig

<400> SEQUENCE: 14

Ile Ser Asn Thr Gly Gly Thr Thr
```

```
<210> SEQ ID NO 15
<211> LENGTH: 8
<212> TYPE: PRT
<213> ORGANISM: Guinea pig

<400> SEQUENCE: 15

Ile Ser Asn Ser Gly Ser Ser Thr
1               5

<210> SEQ ID NO 16
<211> LENGTH: 8
<212> TYPE: PRT
<213> ORGANISM: Guinea pig

<400> SEQUENCE: 16

Ile Thr Tyr His Ser Asp Asp Met
1               5

<210> SEQ ID NO 17
<211> LENGTH: 8
<212> TYPE: PRT
<213> ORGANISM: Guinea pig

<400> SEQUENCE: 17

Ile Ser Gly Gly Gly Ser Tyr Ile
1               5

<210> SEQ ID NO 18
<211> LENGTH: 8
<212> TYPE: PRT
<213> ORGANISM: Guinea pig

<400> SEQUENCE: 18

Ile Lys Gly Asp Ser Ser Thr Ile
1               5

<210> SEQ ID NO 19
<211> LENGTH: 8
<212> TYPE: PRT
<213> ORGANISM: Guinea pig

<400> SEQUENCE: 19

Ile Gly Gly His Gly Thr His Val
1               5

<210> SEQ ID NO 20
<211> LENGTH: 8
<212> TYPE: PRT
<213> ORGANISM: Guinea pig

<400> SEQUENCE: 20

Ile Asn Thr Asp Gly Gly Thr Thr
1               5

<210> SEQ ID NO 21
<211> LENGTH: 14
<212> TYPE: PRT
<213> ORGANISM: Guinea pig

<400> SEQUENCE: 21

Val Arg Arg Arg Thr Gly Val Pro Thr Thr Gly Phe Asp Val
1               5                   10
```

-continued

<210> SEQ ID NO 22
<211> LENGTH: 12
<212> TYPE: PRT
<213> ORGANISM: Guinea pig

<400> SEQUENCE: 22

Val Arg Ala Pro Ile Gly Val Ala Tyr Phe Asp Val
1               5                   10

<210> SEQ ID NO 23
<211> LENGTH: 12
<212> TYPE: PRT
<213> ORGANISM: Guinea pig

<400> SEQUENCE: 23

Val Arg Ala Pro Ile Gly Leu Ala Tyr Phe Asp Thr
1               5                   10

<210> SEQ ID NO 24
<211> LENGTH: 15
<212> TYPE: PRT
<213> ORGANISM: Guinea pig

<400> SEQUENCE: 24

Ala Arg Asp Gly Ala Leu Gly Leu Ala Val Asn Trp Phe Asp Asn
1               5                   10                  15

<210> SEQ ID NO 25
<211> LENGTH: 15
<212> TYPE: PRT
<213> ORGANISM: Guinea pig

<400> SEQUENCE: 25

Val Arg Asp Gly Ala Leu Gly Leu Ala Val Asn Trp Phe Asp Asn
1               5                   10                  15

<210> SEQ ID NO 26
<211> LENGTH: 11
<212> TYPE: PRT
<213> ORGANISM: Guinea pig

<400> SEQUENCE: 26

Ala Thr Ser Asp Asp Tyr Tyr Ala Leu Asn Ile
1               5                   10

<210> SEQ ID NO 27
<211> LENGTH: 15
<212> TYPE: PRT
<213> ORGANISM: Guinea pig

<400> SEQUENCE: 27

Thr Thr Ala Tyr Tyr Ser Arg Tyr Ser Tyr Tyr Met Phe Asp Val
1               5                   10                  15

<210> SEQ ID NO 28
<211> LENGTH: 7
<212> TYPE: PRT
<213> ORGANISM: Guinea pig

<400> SEQUENCE: 28

Thr Thr Ala Leu Arg Asp Val
1               5

<210> SEQ ID NO 29

```
<211> LENGTH: 6
<212> TYPE: PRT
<213> ORGANISM: Guinea pig

<400> SEQUENCE: 29

Gln Ser Ile Ser Asn Tyr
1               5

<210> SEQ ID NO 30
<211> LENGTH: 6
<212> TYPE: PRT
<213> ORGANISM: Guinea pig

<400> SEQUENCE: 30

Gln Ser Val Lys Asn Tyr
1               5

<210> SEQ ID NO 31
<211> LENGTH: 6
<212> TYPE: PRT
<213> ORGANISM: Guinea pig

<400> SEQUENCE: 31

Gln Ser Val Lys Ser Tyr
1               5

<210> SEQ ID NO 32
<211> LENGTH: 6
<212> TYPE: PRT
<213> ORGANISM: Guinea pig

<400> SEQUENCE: 32

Gln Ser Val Ser Lys Tyr
1               5

<210> SEQ ID NO 33
<211> LENGTH: 6
<212> TYPE: PRT
<213> ORGANISM: Guinea pig

<400> SEQUENCE: 33

Gln Gly Ile Ser Ser Tyr
1               5

<210> SEQ ID NO 34
<211> LENGTH: 6
<212> TYPE: PRT
<213> ORGANISM: Guinea pig

<400> SEQUENCE: 34

Gln Gly Ile Ser Asn Tyr
1               5

<210> SEQ ID NO 35
<211> LENGTH: 6
<212> TYPE: PRT
<213> ORGANISM: Guinea pig

<400> SEQUENCE: 35

Gln Gly Val Ser Ser Phe
1               5

<210> SEQ ID NO 36
<211> LENGTH: 4
<212> TYPE: PRT
```

```
<213> ORGANISM: Guinea pig

<400> SEQUENCE: 36

Ser Leu Ala Ser
1

<210> SEQ ID NO 37
<211> LENGTH: 4
<212> TYPE: PRT
<213> ORGANISM: Guinea pig

<400> SEQUENCE: 37

Ser Leu Pro Ser
1

<210> SEQ ID NO 38
<211> LENGTH: 4
<212> TYPE: PRT
<213> ORGANISM: Guinea pig

<400> SEQUENCE: 38

Arg Arg Ala Thr
1

<210> SEQ ID NO 39
<211> LENGTH: 4
<212> TYPE: PRT
<213> ORGANISM: Guinea pig

<400> SEQUENCE: 39

Asn Leu Tyr Ser
1

<210> SEQ ID NO 40
<211> LENGTH: 4
<212> TYPE: PRT
<213> ORGANISM: Guinea pig

<400> SEQUENCE: 40

Tyr Leu Tyr Ser
1

<210> SEQ ID NO 41
<211> LENGTH: 4
<212> TYPE: PRT
<213> ORGANISM: Guinea pig

<400> SEQUENCE: 41

Thr Arg Ala Thr
1

<210> SEQ ID NO 42
<211> LENGTH: 8
<212> TYPE: PRT
<213> ORGANISM: Guinea pig

<400> SEQUENCE: 42

Leu Gln Ser Tyr Ile Tyr Pro Leu
1               5

<210> SEQ ID NO 43
<211> LENGTH: 8
<212> TYPE: PRT
<213> ORGANISM: Guinea pig
```

```
<400> SEQUENCE: 43

Gln Gln Tyr Gln Ser Trp Pro Tyr
1               5

<210> SEQ ID NO 44
<211> LENGTH: 8
<212> TYPE: PRT
<213> ORGANISM: Guinea pig

<400> SEQUENCE: 44

Gln Gln Tyr Gln Ser Trp Pro His
1               5

<210> SEQ ID NO 45
<211> LENGTH: 8
<212> TYPE: PRT
<213> ORGANISM: Guinea pig

<400> SEQUENCE: 45

Tyr Gln Tyr Asn Ser Gly Trp Thr
1               5

<210> SEQ ID NO 46
<211> LENGTH: 9
<212> TYPE: PRT
<213> ORGANISM: Guinea pig

<400> SEQUENCE: 46

Gln Gln Tyr Gly Ser Ser Pro Pro Thr
1               5

<210> SEQ ID NO 47
<211> LENGTH: 9
<212> TYPE: PRT
<213> ORGANISM: Guinea pig

<400> SEQUENCE: 47

Gln Gln Tyr Gly Asn Ser Pro Pro Thr
1               5

<210> SEQ ID NO 48
<211> LENGTH: 9
<212> TYPE: PRT
<213> ORGANISM: Guinea pig

<400> SEQUENCE: 48

Phe Gln Tyr Tyr Ser Gly Ser Pro Thr
1               5

<210> SEQ ID NO 49
<211> LENGTH: 832
<212> TYPE: PRT
<213> ORGANISM: Thermus aquaticus

<400> SEQUENCE: 49

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60
```

```
Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                 85                  90                  95

Ala Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
        290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
        370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
        450                 455                 460

Glu Glu Ile Ala Arg Leu Glu Ala Glu Val Phe Arg Leu Ala Gly His
465                 470                 475                 480
```

```
Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 50
<211> LENGTH: 834
<212> TYPE: PRT
<213> ORGANISM: Thermus thermophilus

<400> SEQUENCE: 50

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30
```

```
Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
                115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
            420                 425                 430

His Glu Val Glu Lys Pro Leu Ser Arg Val Leu Ala His Met Glu Ala
        435                 440                 445
```

```
Thr Gly Val Arg Leu Asp Val Ala Tyr Leu Gln Ala Leu Ser Leu Glu
    450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                    485                 490                 495
Phe Asp Glu Leu Arg Leu Pro Ala Leu Gly Lys Thr Gln Lys Thr Gly
                500                 505                 510
Lys Arg Ser Thr Ser Ala Ala Val Leu Glu Ala Leu Arg Glu Ala His
                515                 520                 525
Pro Ile Val Glu Lys Ile Leu Gln His Arg Glu Leu Thr Lys Leu Lys
530                 535                 540
Asn Thr Tyr Val Asp Pro Leu Pro Ser Leu Val His Pro Arg Thr Gly
545                 550                 555                 560
Arg Leu His Thr Arg Phe Asn Gln Thr Ala Thr Ala Thr Gly Arg Leu
                    565                 570                 575
Ser Ser Ser Asp Pro Asn Leu Gln Asn Ile Pro Val Arg Thr Pro Leu
                580                 585                 590
Gly Gln Arg Ile Arg Arg Ala Phe Val Ala Glu Ala Gly Trp Ala Leu
            595                 600                 605
Val Ala Leu Asp Tyr Ser Gln Ile Glu Leu Arg Val Leu Ala His Leu
610                 615                 620
Ser Gly Asp Glu Asn Leu Ile Arg Val Phe Gln Gly Lys Asp Ile
625                 630                 635                 640
His Thr Gln Thr Ala Ser Trp Met Phe Gly Val Pro Pro Glu Ala Val
                    645                 650                 655
Asp Pro Leu Met Arg Arg Ala Ala Lys Thr Val Asn Phe Gly Val Leu
                660                 665                 670
Tyr Gly Met Ser Ala His Arg Leu Ser Gln Glu Leu Ala Ile Pro Tyr
            675                 680                 685
Glu Glu Ala Val Ala Phe Ile Glu Arg Tyr Phe Gln Ser Phe Pro Lys
690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Tyr Val Pro Asp Leu Asn
                    725                 730                 735
Ala Arg Val Lys Ser Val Arg Glu Ala Ala Glu Arg Met Ala Phe Asn
                740                 745                 750
Met Pro Val Gln Gly Thr Ala Ala Asp Leu Met Lys Leu Ala Met Val
            755                 760                 765
Lys Leu Phe Pro Arg Leu Arg Glu Met Gly Ala Arg Met Leu Leu Gln
770                 775                 780
Val His Asp Glu Leu Leu Leu Glu Ala Pro Gln Ala Arg Ala Glu Glu
785                 790                 795                 800
Val Ala Ala Leu Ala Lys Glu Ala Met Glu Lys Ala Tyr Pro Leu Ala
                    805                 810                 815
Val Pro Leu Glu Val Glu Val Gly Met Gly Glu Asp Trp Leu Ser Ala
                820                 825                 830
Lys Gly

<210> SEQ ID NO 51
<211> LENGTH: 326
<212> TYPE: PRT
<213> ORGANISM: Guinea pig
```

<400> SEQUENCE: 51

```
Ala Pro Ser Val Phe Pro Leu Ala Ala Ser Cys Val Asp Thr Ser Gly
1               5                   10                  15

Ser Met Met Thr Leu Gly Cys Leu Val Lys Gly Tyr Phe Pro Glu Pro
            20                  25                  30

Val Thr Val Lys Trp Asn Ser Gly Ala Leu Thr Ser Gly Val His Thr
        35                  40                  45

Phe Pro Ala Val Leu Gln Ser Gly Leu Tyr Ser Leu Thr Ser Met Val
    50                  55                  60

Thr Val Pro Ser Ser Gln Lys Lys Ala Thr Cys Asn Val Ala His Pro
65                  70                  75                  80

Ala Ser Ser Thr Lys Val Asp Lys Thr Val Glu Pro Ile Arg Thr Pro
                85                  90                  95

Gln Pro Asn Pro Cys Thr Cys Pro Lys Cys Pro Pro Glu Asn Leu
            100                 105                 110

Gly Gly Pro Ser Val Phe Ile Phe Pro Pro Lys Pro Lys Asp Thr Leu
        115                 120                 125

Met Ile Ser Leu Thr Pro Arg Val Thr Cys Val Val Val Asp Val Ser
    130                 135                 140

Gln Asp Glu Pro Glu Val Gln Phe Thr Trp Phe Val Asp Asn Lys Pro
145                 150                 155                 160

Val Gly Asn Ala Glu Thr Lys Pro Arg Val Glu Gln Tyr Asn Thr Thr
                165                 170                 175

Phe Arg Val Glu Ser Val Leu Pro Ile Gln His Gln Asp Trp Leu Arg
            180                 185                 190

Gly Lys Glu Phe Lys Cys Lys Val Tyr Asn Lys Ala Leu Pro Ala Pro
        195                 200                 205

Ile Glu Lys Thr Ile Ser Lys Thr Lys Gly Ala Pro Arg Met Pro Asp
    210                 215                 220

Val Tyr Thr Leu Pro Pro Ser Arg Asp Glu Leu Ser Lys Ser Lys Val
225                 230                 235                 240

Ser Val Thr Cys Leu Ile Ile Asn Phe Phe Pro Ala Asp Ile His Val
                245                 250                 255

Glu Trp Ala Ser Asn Arg Val Pro Val Ser Glu Lys Glu Tyr Lys Asn
            260                 265                 270

Thr Pro Pro Ile Glu Asp Ala Asp Gly Ser Tyr Phe Leu Tyr Ser Lys
        275                 280                 285

Leu Thr Val Asp Lys Ser Ala Trp Asp Gln Gly Thr Val Tyr Thr Cys
    290                 295                 300

Ser Val Met His Glu Ala Leu His Asn His Val Thr Gln Lys Ala Ile
305                 310                 315                 320

Ser Arg Ser Pro Gly Lys
                325
```

<210> SEQ ID NO 52
<211> LENGTH: 101
<212> TYPE: PRT
<213> ORGANISM: Guinea pig

<400> SEQUENCE: 52

```
Thr Ile Ser Leu Phe Pro Pro Ser Ser Glu Glu Val Thr Ala Gly Ser
1               5                   10                  15

Ala Ser Val Val Cys Phe Ile Asn Ser Phe Tyr Pro Arg Asp Ile Thr
            20                  25                  30
```

```
Val Lys Trp Lys Val Asp Gly Ser Glu Arg Ser Gln Gly Ile Leu Asn
        35                  40                  45

Ser Tyr Thr Asp Gln Asp Ser Lys Asp Asn Thr Tyr Ser Leu Ser Ser
     50                  55                  60

Thr Leu Ala Leu Thr Ala Ser Glu Tyr Asn Gln His Glu Arg Tyr Thr
 65                  70                  75                  80

Cys Glu Val Ser His Ala Gly Leu Thr Ser Pro Ala Ala Lys Thr Ile
                 85                  90                  95

Asn Arg Ser Glu Cys
            100

<210> SEQ ID NO 53
<211> LENGTH: 320
<212> TYPE: PRT
<213> ORGANISM: Mus musculus

<400> SEQUENCE: 53

Pro Pro Ser Val Tyr Pro Leu Ala Pro Gly Ser Ala Ala Gln Thr Asn
 1               5                  10                  15

Ser Met Val Thr Leu Gly Cys Leu Val Lys Gly Tyr Phe Pro Glu Pro
             20                  25                  30

Val Thr Val Thr Trp Asn Ser Gly Ser Leu Ser Ser Gly Val His Thr
        35                  40                  45

Phe Pro Ala Val Leu Gln Ser Asp Leu Tyr Thr Leu Ser Ser Ser Val
     50                  55                  60

Thr Val Pro Ser Ser Thr Trp Pro Ser Glu Thr Val Thr Cys Asn Val
 65                  70                  75                  80

Ala His Pro Ala Ser Ser Thr Lys Val Asp Lys Lys Ile Val Pro Arg
                 85                  90                  95

Asp Cys Gly Cys Lys Pro Cys Ile Cys Thr Val Pro Glu Val Ser Ser
            100                 105                 110

Val Phe Ile Phe Pro Pro Lys Pro Lys Asp Val Leu Thr Ile Thr Leu
        115                 120                 125

Thr Pro Lys Val Thr Cys Val Val Val Asp Ile Ser Lys Asp Asp Pro
    130                 135                 140

Glu Val Gln Phe Ser Trp Phe Val Asp Asp Val Glu Val His Thr Ala
145                 150                 155                 160

Gln Thr Gln Pro Arg Glu Glu Gln Phe Asn Ser Thr Phe Arg Ser Val
                165                 170                 175

Ser Glu Leu Pro Ile Met His Gln Asp Trp Leu Asn Gly Lys Glu Phe
            180                 185                 190

Lys Cys Arg Val Asn Ser Ala Ala Phe Pro Ala Pro Ile Glu Lys Thr
        195                 200                 205

Ile Ser Lys Thr Lys Gly Arg Pro Lys Ala Pro Gln Val Tyr Thr Ile
    210                 215                 220

Pro Pro Pro Lys Glu Gln Met Ala Lys Asp Lys Val Ser Leu Thr Cys
225                 230                 235                 240

Met Ile Thr Asp Phe Phe Pro Glu Asp Ile Thr Val Glu Trp Gln Trp
                245                 250                 255

Asn Gly Gln Pro Ala Glu Asn Tyr Lys Asn Thr Gln Pro Ile Met Asp
            260                 265                 270

Thr Asp Gly Ser Tyr Phe Val Tyr Ser Lys Leu Asn Val Gln Lys Ser
        275                 280                 285

Asn Trp Glu Ala Gly Asn Thr Phe Thr Cys Ser Val Leu His Glu Gly
```

```
              290                 295                 300
Leu His Asn His His Thr Glu Lys Ser Leu Ser His Ser Pro Gly Lys
305                 310                 315                 320

<210> SEQ ID NO 54
<211> LENGTH: 101
<212> TYPE: PRT
<213> ORGANISM: Mus musculus

<400> SEQUENCE: 54

Thr Val Ser Ile Phe Pro Pro Ser Ser Glu Gln Leu Thr Ser Gly Gly
1               5                   10                  15

Ala Ser Val Val Cys Phe Leu Asn Asn Phe Tyr Pro Lys Asp Ile Asn
                20                  25                  30

Val Lys Trp Lys Ile Asp Gly Ser Glu Arg Gln Asn Gly Val Leu Asn
            35                  40                  45

Ser Trp Thr Asp Gln Asp Ser Lys Asp Ser Thr Tyr Ser Met Ser Ser
        50                  55                  60

Thr Leu Thr Leu Thr Lys Asp Glu Tyr Glu Arg His Asn Ser Tyr Thr
65                  70                  75                  80

Cys Glu Ala Thr His Lys Thr Ser Thr Ser Pro Ile Val Lys Ser Phe
                85                  90                  95

Asn Arg Gly Glu Cys
            100

<210> SEQ ID NO 55
<211> LENGTH: 834
<212> TYPE: PRT
<213> ORGANISM: Thermus sp. Z05

<400> SEQUENCE: 55

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
```

```
            195                 200                 205
Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Lys Glu Gly Arg Val His Arg
            325                 330                 335

Ala Lys Asp Pro Leu Ala Gly Leu Lys Asp Leu Lys Glu Val Arg Gly
            340                 345                 350

Leu Leu Ala Lys Asp Leu Ala Val Leu Ala Leu Arg Glu Gly Leu Asp
            355                 360                 365

Leu Ala Pro Ser Asp Asp Pro Met Leu Leu Ala Tyr Leu Leu Asp Pro
370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ala Glu Arg Leu Gln Gln
            405                 410                 415

Asn Leu Leu Glu Arg Leu Lys Gly Glu Glu Lys Leu Leu Trp Leu Tyr
            420                 425                 430

Gln Glu Val Glu Lys Pro Leu Ser Arg Val Leu Ala His Met Glu Ala
            435                 440                 445

Thr Gly Val Arg Leu Asp Val Ala Tyr Leu Lys Ala Leu Ser Leu Glu
450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
530                 535                 540

Asn Thr Tyr Val Asp Pro Leu Pro Gly Leu Val His Pro Arg Thr Gly
545                 550                 555                 560

Arg Leu His Thr Arg Phe Asn Gln Thr Ala Thr Ala Thr Gly Arg Leu
            565                 570                 575

Ser Ser Ser Asp Pro Asn Leu Gln Asn Ile Pro Ile Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
610                 615                 620
```

```
Ser Gly Asp Glu Asn Leu Ile Arg Val Phe Gln Gly Lys Asp Ile
625                 630                 635                 640

His Thr Gln Thr Ala Ser Trp Met Phe Gly Val Ser Pro Glu Ala Val
            645                 650                 655

Asp Pro Leu Met Arg Arg Ala Ala Lys Thr Val Asn Phe Gly Val Leu
        660                 665                 670

Tyr Gly Met Ser Ala His Arg Leu Ser Gln Glu Leu Ala Ile Pro Tyr
    675                 680                 685

Glu Glu Ala Val Ala Phe Ile Glu Arg Tyr Phe Gln Ser Phe Pro Lys
690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
            725                 730                 735

Ala Arg Val Lys Ser Val Arg Glu Ala Ala Glu Arg Met Ala Phe Asn
        740                 745                 750

Met Pro Val Gln Gly Thr Ala Ala Asp Leu Met Lys Leu Ala Met Val
    755                 760                 765

Lys Leu Phe Pro His Leu Arg Glu Met Gly Ala Arg Met Leu Leu Gln
770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
            805                 810                 815

Val Pro Leu Glu Val Glu Val Gly Ile Gly Glu Asp Trp Leu Ser Ala
        820                 825                 830

Lys Gly

<210> SEQ ID NO 56
<211> LENGTH: 30
<212> TYPE: DNA
<213> ORGANISM: Bacteriophage lambda

<400> SEQUENCE: 56
actcattcgt tttatacctc tgaatcaata                                   30

<210> SEQ ID NO 57
<211> LENGTH: 40
<212> TYPE: DNA
<213> ORGANISM: Bacteriophage lambda

<400> SEQUENCE: 57
gttgatattg attcagaggt ataaaacgaa tgagtactgc                        40

<210> SEQ ID NO 58
<211> LENGTH: 30
<212> TYPE: DNA
<213> ORGANISM: Bacteriophage lambda

<400> SEQUENCE: 58
actaataagc cgatagatag ccacggactt                                   30

<210> SEQ ID NO 59
<211> LENGTH: 40
<212> TYPE: DNA
<213> ORGANISM: Bacteriophage lambda

<400> SEQUENCE: 59
```

```
ctacgaagtc cgtggctatc tatcggctta ttagtacttg                           40
```

<210> SEQ ID NO 60
<211> LENGTH: 10
<212> TYPE: PRT
<213> ORGANISM: Artificial sequence
<220> FEATURE:
<223> OTHER INFORMATION: Epitope

<400> SEQUENCE: 60

Glu Asp Gly Asp Ala Val Ile Val Val Phe
1               5                   10

<210> SEQ ID NO 61
<211> LENGTH: 11
<212> TYPE: PRT
<213> ORGANISM: Artificial sequence
<220> FEATURE:
<223> OTHER INFORMATION: Epitope

<400> SEQUENCE: 61

Lys Glu Asp Gly Asp Ala Val Ile Val Val Phe
1               5                   10

<210> SEQ ID NO 62
<211> LENGTH: 11
<212> TYPE: PRT
<213> ORGANISM: Artificial sequence
<220> FEATURE:
<223> OTHER INFORMATION: Epitope

<400> SEQUENCE: 62

Glu Asp Gly Tyr Lys Ala Val Phe Val Val Phe
1               5                   10

<210> SEQ ID NO 63
<211> LENGTH: 12
<212> TYPE: PRT
<213> ORGANISM: Artificial sequence
<220> FEATURE:
<223> OTHER INFORMATION: Epitope

<400> SEQUENCE: 63

Lys Glu Asp Gly Tyr Lys Ala Val Phe Val Val Phe
1               5                   10

<210> SEQ ID NO 64
<211> LENGTH: 7
<212> TYPE: PRT
<213> ORGANISM: Artificial sequence
<220> FEATURE:
<223> OTHER INFORMATION: Epitope

<400> SEQUENCE: 64

His Glu Ala Tyr Gly Gly Tyr
1               5

<210> SEQ ID NO 65
<211> LENGTH: 7
<212> TYPE: PRT
<213> ORGANISM: Artificial sequence
<220> FEATURE:
<223> OTHER INFORMATION: Epitope

<400> SEQUENCE: 65

His Glu Ala Tyr Glu Ala Tyr

```
<210> SEQ ID NO 66
<211> LENGTH: 9
<212> TYPE: PRT
<213> ORGANISM: Artificial sequence
<220> FEATURE:
<223> OTHER INFORMATION: Epitope

<400> SEQUENCE: 66

His Leu Ile Thr Pro Glu Trp Leu Trp
1               5

<210> SEQ ID NO 67
<211> LENGTH: 12
<212> TYPE: PRT
<213> ORGANISM: Artificial sequence
<220> FEATURE:
<223> OTHER INFORMATION: Epitope

<400> SEQUENCE: 67

Lys Tyr Gly Leu Arg Pro Glu Gln Trp Val Asp Phe
1               5                   10

<210> SEQ ID NO 68
<211> LENGTH: 13
<212> TYPE: PRT
<213> ORGANISM: Artificial sequence
<220> FEATURE:
<223> OTHER INFORMATION: Epitope

<400> SEQUENCE: 68

Glu Lys Tyr Gly Leu Arg Pro Asp Gln Trp Ala Asp Tyr
1               5                   10

<210> SEQ ID NO 69
<211> LENGTH: 12
<212> TYPE: PRT
<213> ORGANISM: Artificial seqence
<220> FEATURE:
<223> OTHER INFORMATION: Epitope

<400> SEQUENCE: 69

Lys Tyr Gly Leu Arg Pro Asp Gln Trp Ala Asp Tyr
1               5                   10

<210> SEQ ID NO 70
<211> LENGTH: 10
<212> TYPE: PRT
<213> ORGANISM: Artificial sequence
<220> FEATURE:
<223> OTHER INFORMATION: Epitope

<400> SEQUENCE: 70

Gly Leu Arg Pro Glu Gln Trp Val Asp Phe
1               5                   10

<210> SEQ ID NO 71
<211> LENGTH: 7
<212> TYPE: PRT
<213> ORGANISM: Artificial sequence
<220> FEATURE:
<223> OTHER INFORMATION: Epitope

<400> SEQUENCE: 71

Ile Thr Pro Glu Trp Leu Trp
1               5
```

```
<210> SEQ ID NO 72
<211> LENGTH: 22
<212> TYPE: PRT
<213> ORGANISM: Artificial sequence
<220> FEATURE:
<223> OTHER INFORMATION: Epitope

<400> SEQUENCE: 72

Tyr Leu Ile Thr Pro Ala Trp Leu Trp Glu Lys Tyr Gly Leu Arg Pro
1               5                   10                  15

Asp Gln Trp Ala Asp Tyr
            20

<210> SEQ ID NO 73
<211> LENGTH: 22
<212> TYPE: PRT
<213> ORGANISM: Artificial sequence
<220> FEATURE:
<223> OTHER INFORMATION: Epitope

<400> SEQUENCE: 73

His Leu Ile Thr Pro Glu Trp Leu Trp Glu Lys Tyr Gly Leu Arg Pro
1               5                   10                  15

Glu Gln Trp Val Asp Phe
            20

<210> SEQ ID NO 74
<211> LENGTH: 22
<212> TYPE: PRT
<213> ORGANISM: Artificial sequence
<220> FEATURE:
<223> OTHER INFORMATION: Epitope

<400> SEQUENCE: 74

His Leu Ile Thr Pro Glu Trp Leu Trp Glu Lys Tyr Gly Leu Lys Pro
1               5                   10                  15

Glu Gln Trp Val Asp Phe
            20

<210> SEQ ID NO 75
<211> LENGTH: 6
<212> TYPE: PRT
<213> ORGANISM: Artificial sequence
<220> FEATURE:
<223> OTHER INFORMATION: Epitope

<400> SEQUENCE: 75

Leu Glu Arg Leu Glu Phe
1               5

<210> SEQ ID NO 76
<211> LENGTH: 11
<212> TYPE: PRT
<213> ORGANISM: Artificial sequence
<220> FEATURE:
<223> OTHER INFORMATION: Epitope

<400> SEQUENCE: 76

Leu Glu Arg Leu Glu Phe Gly Ser Leu Leu His
1               5                   10

<210> SEQ ID NO 77
<211> LENGTH: 13
<212> TYPE: PRT
```

```
<213> ORGANISM: Artificial sequence
<220> FEATURE:
<223> OTHER INFORMATION: Epitope

<400> SEQUENCE: 77

Leu Glu Arg Leu Glu Phe Gly Ser Leu Leu His Glu Phe
1               5                   10

<210> SEQ ID NO 78
<211> LENGTH: 10
<212> TYPE: PRT
<213> ORGANISM: Artificial sequence
<220> FEATURE:
<223> OTHER INFORMATION: Epitope

<400> SEQUENCE: 78

Leu Arg Ala Phe Leu Glu Arg Leu Glu Phe
1               5                   10

<210> SEQ ID NO 79
<211> LENGTH: 9
<212> TYPE: PRT
<213> ORGANISM: Artificial sequence
<220> FEATURE:
<223> OTHER INFORMATION: Epitope

<400> SEQUENCE: 79

Arg Ala Phe Leu Glu Arg Leu Glu Phe
1               5

<210> SEQ ID NO 80
<211> LENGTH: 14
<212> TYPE: PRT
<213> ORGANISM: Artificial sequence
<220> FEATURE:
<223> OTHER INFORMATION: Epitope

<400> SEQUENCE: 80

Arg Ala Phe Leu Glu Arg Leu Glu Phe Gly Ser Leu Leu His
1               5                   10

<210> SEQ ID NO 81
<211> LENGTH: 8
<212> TYPE: PRT
<213> ORGANISM: Artificial sequence
<220> FEATURE:
<223> OTHER INFORMATION: Epitope

<400> SEQUENCE: 81

Leu Glu Phe Gly Ser Leu Leu His
1               5

<210> SEQ ID NO 82
<211> LENGTH: 10
<212> TYPE: PRT
<213> ORGANISM: Artificial sequence
<220> FEATURE:
<223> OTHER INFORMATION: Epitope

<400> SEQUENCE: 82

Leu Glu Phe Gly Ser Leu Leu His Glu Phe
1               5                   10

<210> SEQ ID NO 83
<211> LENGTH: 17
<212> TYPE: PRT
<213> ORGANISM: Artificial sequence
```

```
<220> FEATURE:
<223> OTHER INFORMATION: Epitope

<400> SEQUENCE: 83

Leu Arg Ala Phe Leu Glu Arg Leu Glu Phe Gly Ser Leu Leu His Glu
1               5                   10                  15

Phe

<210> SEQ ID NO 84
<211> LENGTH: 14
<212> TYPE: PRT
<213> ORGANISM: Artificial sequence
<220> FEATURE:
<223> OTHER INFORMATION: Heavy Chain CDR3
<220> FEATURE:
<221> NAME/KEY: MISC_FEATURE
<222> LOCATION: (3)..(3)
<223> OTHER INFORMATION: X is Ala, Ser, Asp, Lys, His, or Arg.
<220> FEATURE:
<221> NAME/KEY: MISC_FEATURE
<222> LOCATION: (4)..(4)
<223> OTHER INFORMATION: X is Gly, Ala, Asp, Pro, Lys, His, or Arg.
<220> FEATURE:
<221> NAME/KEY: MISC_FEATURE
<222> LOCATION: (5)..(5)
<223> OTHER INFORMATION: X is Ser, Thr, Leu, Tyr, or Ile.
<220> FEATURE:
<221> NAME/KEY: MISC_FEATURE
<222> LOCATION: (7)..(7)
<223> OTHER INFORMATION: X is Ala, Val, Ile, Arg, or Leu.
<220> FEATURE:
<221> NAME/KEY: MISC_FEATURE
<222> LOCATION: (8)..(8)
<223> OTHER INFORMATION: X is Ala, Val, Tyr, or Pro.
<220> FEATURE:
<221> NAME/KEY: MISC_FEATURE
<222> LOCATION: (9)..(9)
<223> OTHER INFORMATION: X is Ala, Val, Ser, Thr, or Tyr.
<220> FEATURE:
<221> NAME/KEY: MISC_FEATURE
<222> LOCATION: (14)..(14)
<223> OTHER INFORMATION: X is Val, Ile, Leu, Ser, Thr, or Asn.

<400> SEQUENCE: 84

Val Arg Xaa Xaa Xaa Gly Xaa Xaa Xaa Thr Gly Phe Asp Xaa
1               5                   10

<210> SEQ ID NO 85
<211> LENGTH: 12
<212> TYPE: PRT
<213> ORGANISM: Artificial sequence
<220> FEATURE:
<223> OTHER INFORMATION: Heavy Chain CDR3 Formula
<220> FEATURE:
<221> NAME/KEY: MISC_FEATURE
<222> LOCATION: (3)..(3)
<223> OTHER INFORMATION: X is Ala, Ser, Asp, Lys, His, or Arg
<220> FEATURE:
<221> NAME/KEY: MISC_FEATURE
<222> LOCATION: (4)..(4)
<223> OTHER INFORMATION: X is Gly, Ala, Asp, Pro, Lys, His, or Arg.
<220> FEATURE:
<221> NAME/KEY: MISC_FEATURE
<222> LOCATION: (5)..(5)
<223> OTHER INFORMATION: X is Ser, Thr, Leu, Tyr, or Ile.
<220> FEATURE:
<221> NAME/KEY: MISC_FEATURE
<222> LOCATION: (7)..(7)
<223> OTHER INFORMATION: X is Ala, Val, Ile, Arg, or Leu.
<220> FEATURE:
<221> NAME/KEY: MISC_FEATURE
<222> LOCATION: (8)..(8)
<223> OTHER INFORMATION: X is Ala, Val, Tyr, or Pro.
<220> FEATURE:
```

```
<221> NAME/KEY: MISC_FEATURE
<222> LOCATION: (9)..(9)
<223> OTHER INFORMATION: X is Ala, Val, Ser, Thr, or Tyr.
<220> FEATURE:
<221> NAME/KEY: MISC_FEATURE
<222> LOCATION: (12)..(12)
<223> OTHER INFORMATION: X is Val, Ile, Leu, Ser, Thr, or Asn.

<400> SEQUENCE: 85

Val Arg Xaa Xaa Xaa Gly Xaa Xaa Xaa Phe Asp Xaa
1               5                   10

<210> SEQ ID NO 86
<211> LENGTH: 15
<212> TYPE: PRT
<213> ORGANISM: Artificial sequence
<220> FEATURE:
<223> OTHER INFORMATION: Heavy Chain CDR3 Formula
<220> FEATURE:
<221> NAME/KEY: MISC_FEATURE
<222> LOCATION: (1)..(1)
<223> OTHER INFORMATION: X is Ala or Val.
<220> FEATURE:
<221> NAME/KEY: MISC_FEATURE
<222> LOCATION: (15)..(15)
<223> OTHER INFORMATION: X is Val, Ile, Leu, Ser, Thr, or Asn.

<400> SEQUENCE: 86

Xaa Arg Asp Gly Ala Leu Gly Leu Ala Val Asn Trp Phe Asp Xaa
1               5                   10                  15

<210> SEQ ID NO 87
<211> LENGTH: 11
<212> TYPE: PRT
<213> ORGANISM: Artificial sequence
<220> FEATURE:
<223> OTHER INFORMATION: Heavy Chain CDR3 Formula

<400> SEQUENCE: 87

Ala Thr Ser Asp Asp Tyr Tyr Ala Leu Asn Ile
1               5                   10

<210> SEQ ID NO 88
<211> LENGTH: 15
<212> TYPE: PRT
<213> ORGANISM: Artificial sequence
<220> FEATURE:
<223> OTHER INFORMATION: Heavy Chain CDR3 Formula
<220> FEATURE:
<221> NAME/KEY: MISC_FEATURE
<222> LOCATION: (15)..(15)
<223> OTHER INFORMATION: X is Val, Ile, Leu, Ser, Thr, or Asn.

<400> SEQUENCE: 88

Thr Thr Ala Tyr Tyr Ser Arg Tyr Ser Tyr Tyr Met Phe Asp Xaa
1               5                   10                  15

<210> SEQ ID NO 89
<211> LENGTH: 7
<212> TYPE: PRT
<213> ORGANISM: Artificial sequence
<220> FEATURE:
<223> OTHER INFORMATION: Heavy Chain CDR3 Formula
<220> FEATURE:
<221> NAME/KEY: MISC_FEATURE
<222> LOCATION: (7)..(7)
<223> OTHER INFORMATION: X is Val, Ile, Leu, Ser, Thr, or Asn.

<400> SEQUENCE: 89

Thr Thr Ala Leu Arg Asp Xaa
```

```
1               5

<210> SEQ ID NO 90
<211> LENGTH: 8
<212> TYPE: PRT
<213> ORGANISM: Artificial sequence
<220> FEATURE:
<223> OTHER INFORMATION: Heavy Chain CDR1 Formula
<220> FEATURE:
<221> NAME/KEY: MISC_FEATURE
<222> LOCATION: (5)..(5)
<223> OTHER INFORMATION: X is Asp, Asn, or Ser.
<220> FEATURE:
<221> NAME/KEY: MISC_FEATURE
<222> LOCATION: (6)..(6)
<223> OTHER INFORMATION: X is Asp, Asn, Ser, Lys, or His.
<220> FEATURE:
<221> NAME/KEY: MISC_FEATURE
<222> LOCATION: (7)..(7)
<223> OTHER INFORMATION: X is Tyr or Trp.
<220> FEATURE:
<221> NAME/KEY: MISC_FEATURE
<222> LOCATION: (8)..(8)
<223> OTHER INFORMATION: X is Gly, Trp, or Tyr.

<400> SEQUENCE: 90

Gly Phe Thr Phe Xaa Xaa Xaa Xaa
1               5

<210> SEQ ID NO 91
<211> LENGTH: 14
<212> TYPE: PRT
<213> ORGANISM: Artificial sequence
<220> FEATURE:
<223> OTHER INFORMATION: Heavy Chain CDR3 Formula
<220> FEATURE:
<221> NAME/KEY: MISC_FEATURE
<222> LOCATION: (3)..(3)
<223> OTHER INFORMATION: X is Ala or Arg.
<220> FEATURE:
<221> NAME/KEY: MISC_FEATURE
<222> LOCATION: (4)..(4)
<223> OTHER INFORMATION: X is Pro or Arg.
<220> FEATURE:
<221> NAME/KEY: MISC_FEATURE
<222> LOCATION: (5)..(5)
<223> OTHER INFORMATION: X is Thr or Ile.
<220> FEATURE:
<221> NAME/KEY: MISC_FEATURE
<222> LOCATION: (7)..(7)
<223> OTHER INFORMATION: X is Val or Leu.
<220> FEATURE:
<221> NAME/KEY: MISC_FEATURE
<222> LOCATION: (8)..(8)
<223> OTHER INFORMATION: X is Pro or Ala.
<220> FEATURE:
<221> NAME/KEY: MISC_FEATURE
<222> LOCATION: (9)..(9)
<223> OTHER INFORMATION: X is Thr or Tyr.
<220> FEATURE:
<221> NAME/KEY: MISC_FEATURE
<222> LOCATION: (14)..(14)
<223> OTHER INFORMATION: X is Val, Thr, or Asn.

<400> SEQUENCE: 91

Val Arg Xaa Xaa Xaa Gly Xaa Xaa Xaa Thr Gly Phe Asp Xaa
1               5                   10

<210> SEQ ID NO 92
<211> LENGTH: 12
<212> TYPE: PRT
<213> ORGANISM: Artificial sequence
<220> FEATURE:
<223> OTHER INFORMATION: Heavy Chain CDR3 Formula
```

```
<220> FEATURE:
<221> NAME/KEY: MISC_FEATURE
<222> LOCATION: (3)..(3)
<223> OTHER INFORMATION: X is Ala or Arg.
<220> FEATURE:
<221> NAME/KEY: MISC_FEATURE
<222> LOCATION: (4)..(4)
<223> OTHER INFORMATION: X is Pro or Arg.
<220> FEATURE:
<221> NAME/KEY: MISC_FEATURE
<222> LOCATION: (5)..(5)
<223> OTHER INFORMATION: X is Thr or Ile.
<220> FEATURE:
<221> NAME/KEY: MISC_FEATURE
<222> LOCATION: (7)..(7)
<223> OTHER INFORMATION: X is Val or Leu.
<220> FEATURE:
<221> NAME/KEY: MISC_FEATURE
<222> LOCATION: (8)..(8)
<223> OTHER INFORMATION: X is Pro or Ala.
<220> FEATURE:
<221> NAME/KEY: MISC_FEATURE
<222> LOCATION: (9)..(9)
<223> OTHER INFORMATION: X is Thr or Tyr.
<220> FEATURE:
<221> NAME/KEY: MISC_FEATURE
<222> LOCATION: (12)..(12)
<223> OTHER INFORMATION: X is Val, Thr, or Asn.

<400> SEQUENCE: 92

Val Arg Xaa Xaa Xaa Gly Xaa Xaa Xaa Phe Asp Xaa
1               5                   10

<210> SEQ ID NO 93
<211> LENGTH: 15
<212> TYPE: PRT
<213> ORGANISM: Artificial sequence
<220> FEATURE:
<223> OTHER INFORMATION: Heavy Chain CDR3 Formula
<220> FEATURE:
<221> NAME/KEY: MISC_FEATURE
<222> LOCATION: (1)..(1)
<223> OTHER INFORMATION: X is Ala or Val.
<220> FEATURE:
<221> NAME/KEY: MISC_FEATURE
<222> LOCATION: (15)..(15)
<223> OTHER INFORMATION: X is Val, Thr, or Asn.

<400> SEQUENCE: 93

Xaa Arg Asp Gly Ala Leu Gly Leu Ala Val Asn Trp Phe Asp Xaa
1               5                   10                  15

<210> SEQ ID NO 94
<211> LENGTH: 15
<212> TYPE: PRT
<213> ORGANISM: Artificial sequence
<220> FEATURE:
<223> OTHER INFORMATION: Heavy Chain CDR3 Formula
<220> FEATURE:
<221> NAME/KEY: MISC_FEATURE
<222> LOCATION: (15)..(15)
<223> OTHER INFORMATION: X is Val, Thr, or Asn.

<400> SEQUENCE: 94

Thr Thr Ala Tyr Tyr Ser Arg Tyr Ser Tyr Tyr Met Phe Asp Xaa
1               5                   10                  15

<210> SEQ ID NO 95
<211> LENGTH: 7
<212> TYPE: PRT
<213> ORGANISM: Artificial sequence
<220> FEATURE:
<223> OTHER INFORMATION: Heavy Chain CDR3 Formula
```

```
<220> FEATURE:
<221> NAME/KEY: MISC_FEATURE
<222> LOCATION: (7)..(7)
<223> OTHER INFORMATION: X is Val, Thr, or Asn.

<400> SEQUENCE: 95

Thr Thr Ala Leu Arg Asp Xaa
1               5
```

ANTIBODY CAPABLE OF BINDING SPECIFICALLY TO 5' TO 3' EXONUCLEASE ACTIVE DOMAIN OF DNA POLYMERASE

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: 55,347 bytes ASCII (Text) file named "764795_ST25_ReplacementSequenceListing.txt" created Dec. 5, 2023.

TECHNICAL FIELD

Provided are antibodies that specifically bind to a 5' to 3' exonuclease activity domain (also referred to as "5' to 3' exonuclease domain") of a DNA polymerase for use in nucleic acid amplification methods, in particular, polymerase chain reactions (referred to below as "PCR") etc., and techniques related to the antibodies.

Background Art

DNA synthesis from a nucleic acid template using a DNA polymerase has been used in and applied to various methods, such as sequencing and nucleic acid amplification methods, in the field of molecular biology. In particular, nucleic acid amplification methods have already been put into practical use not only in the research field but also in the forensic field, such as genetic diagnosis and paternity testing, as well as in microbiological testing etc. of food and the environment.

Typical nucleic acid amplification methods include PCR. PCR is a method for amplifying a target nucleic acid in a sample by repeating the following three steps as one cycle: (1) DNA denaturation by heat treatment (dissociation of double-stranded DNA into single-stranded DNA), (2) annealing of primers to the template single-stranded DNA, and (3) extension of the primers using a DNA polymerase. In some cases, (2) annealing and (3) extension may be performed at the same temperature and in a single step so that the one cycle consists of two steps.

PCR has been widely used in medical and biological research, clinical diagnosis, etc., because of its characteristics, such as sensitivity that allows amplification from a single copy of nucleic acid sample in principle and from nucleic acid samples equivalent to several copies even in actuality, and specificity that allows amplification of only a specific moiety. Further development on PCR is currently underway; and there are various techniques, such as multiplex PCR methods, which amplify multiple primers simultaneously, and real-time PCR methods, which use fluorescent dyes and fluorescent-labeled probes to monitor the generation process of amplification products over time.

These nucleic acid amplification methods are also widely used in genetic analysis of a large amount of samples, such as high-throughput screening (HTS), and in food or environmental testing, in which many samples need to be processed. When analyzing a large amount of samples, the reaction liquid for nucleic acid amplification is assumed to be left for a long period of time after preparation (e.g., hours to days). However, there is a concern that leaving the reaction liquid at room temperature may reduce the stability of the reaction liquid. For example, in the TaqMan (registered trademark) probe method (see, for example, Non-patent Literature (NPL) 1), several examples of phenomena have been confirmed in which leaving a reaction liquid at room temperature after preparation caused a delay in the Ct (threshold cycle) value or made the detection of the Ct value itself impossible (Patent Literature (PTL) 1 and 2).

CITATION LIST

Patent Literature

PTL 1: JP2017-163904A
PTL 2: JP2016-136324A1

Non-Patent Literature

NPL 1: Holland et al., Proc. Natl. Acad. Sci. vol. 88, 1991, pp. 7276-7280

SUMMARY OF INVENTION

Technical Problem

The present inventors have found so far the problem that nucleic acid templates, primers, probes, etc. used in nucleic acid amplification methods etc. would be degraded when present together with a DNA polymerase having a 5' to 3' exonuclease domain.

A main object of the present invention is to provide an antibody against (that specifically binds to) a 5' to 3' exonuclease domain of a DNA polymerase, or a fragment thereof, and a method for producing the antibody or a fragment thereof.

Solution to Problem

As a result of extensive research to solve the above problems, the present inventors found an antibody against (that specifically binds to) a 5' to 3' exonuclease domain of a DNA polymerase, or a fragment thereof, and a useful method for producing the antibody or a fragment thereof. The present invention has been completed as a result of further extensive research based on these findings.

The present invention typically encompasses the following.

Item 1.
An antibody that specifically binds to a 5' to 3' exonuclease domain of a DNA polymerase, or a fragment thereof (antigen-binding fragment).

Item 2.
The antibody or a fragment thereof according to Item 1, wherein the DNA polymerase is selected from the group consisting of Taq polymerase, Tth polymerase, and Z05 polymerase.

Item 3.
An antibody or a fragment thereof (antigen-binding fragment), the antibody comprising:
heavy chain CDR1 comprising an amino acid sequence represented by formula (A-1):

$$\text{(A-1)}$$
$$\text{GFX}^{43}\text{X}^{44}\text{X}^{45}\text{X}^{46}\text{X}^{47}\text{X}^{48},$$

wherein
$X^{43}$ is T or S,
$X^{44}$ is F, L, or I,
$X^{45}$ is D, N, S, or T,
$X^{46}$ is D, N, S, T, K, R, or H, $X^{A7}$ is Y, F, or W, and
$X^{A8}$ is G, S, T, W, Y, or F;
heavy chain CDR2 comprising an amino acid sequence represented by formula (B-1):

$$\text{(B-1)}$$
$$IX^{B2}X^{B3}X^{B4}X^{B5}X^{B6}X^{B7}X^{B8},$$

wherein
$X^{B2}$ is G, S, T, K, R, H, D, or N,
$X^{B3}$ is F, Y, L, I, G, S, T, D, or N,
$X^{B4}$ is G, S, T, D, N, K, R, or H,
$X^{B5}$ is G, S, T, or A,
$X^{B6}$ is G, S, T, D, or N,
$X^{B7}$ is S, T, F, Y, D, N, K, R, or H, and
$X^{B8}$ is S, T, V, L, I, or M;
heavy chain CDR3 comprising an amino acid sequence represented by any one of formulas (C-1) to (C-6):

$$\text{(C-1)}$$
$$VRX^{C1}X^{C2}X^{C3}GX^{C4}X^{C5}X^{C6}TGFDX^{C7},$$

$$\text{(C-2)}$$
$$VRX^{C1}X^{C2}X^{C3}GX^{C4}X^{C5}X^{C6}FDX^{C7},$$

$$\text{(C-3)}$$
$$X^{C8}RDGALGLAVNWFDX^{C7},$$

$$\text{(C-4)}$$
$$ATSDDYYALNI,$$

$$\text{(C-5)}$$
$$TTAYYSRYSYYMFDX^{C7},$$
and $$\text{(C-6)}$$
$$TTALRDX^{C7},$$

wherein
$X^{C1}$ is A, S, D, K, H, or R,
$X^{C2}$ is G, A, D, P, K, H, or R,
$X^{C3}$ is S, T, L, Y, or I,
$X^{C4}$ is A, V, I, R, or L,
$X^{C5}$ is A, V, Y, or P,
$X^{C6}$ is A, V, S, T, or Y,
$X^{C7}$ is V, I, L, S, T, or N, and
$X^{C8}$ is A or V;
light chain CDR1 comprising an amino acid sequence represented by formula (D-1):

$$\text{(D-1)}$$
$$X^{D1}X^{D2}X^{D3}X^{D4}X^{D5}X^{D6},$$

wherein
$X^{D1}$ is E, Q, D, or N,
$X^{D2}$ is G, A, S, or T,
$X^{D3}$ is A, V, L, I, or F,
$X^{D4}$ is S, T, K, R, or H,
$X^{D5}$ is S, T, D, N, K, R, or H, and
$X^{D6}$ is F, Y, or W;
light chain CDR2 comprising an amino acid sequence represented by formula (E-1):

$$\text{(E-1)}$$
$$X^{E1}X^{E2}X^{E3},$$

wherein
$X^{E1}$ is G, S, T, D, N, F, Y, K, R, or H,
$X^{E2}$ is G, A, S, T, V, L, or I, and
$X^{E3}$ is K, R, H, D, N, S, or T; and light chain CDR3 comprising an amino acid sequence represented by formula (F-1) or (F-2):

$$\text{(F-1)}$$
$$(X^{F1}X^{F2}X^{F3}X^{F4}X^{F5}X^{F6}X^{F7}X^{F8}$$
or $$\text{(F-2)}$$
$$(X^{F1}X^{F2}X^{F3}X^{F4}X^{F5}X^{F6}X^{F7}X^{F8}X^{F9},$$

wherein
$X^{F1}$ is L, I, E, Q, F, Y, or W,
$X^{F2}$ is D, N, E, or Q,
$X^{F3}$ is S, T, F, or Y,
$X^{F4}$ is G, S, T, F, Y, N, or Q,
$X^{F5}$ is S, T, N, Q, L, or I,
$X^{F6}$ is G, S, T, F, Y, or W,
$X^{F7}$ is S, T, P, Y, or W,
$X^{F8}$ is L, I, P, K, R, H, Y, T, or W, and
$X^{F9}$ is G, S, T, D, or E.
Item 4.
The antibody or a fragment thereof according to Item 3, further comprising a sequence region adjacent to the C-terminus of the light chain CDR2, the sequence region comprising an amino acid sequence represented by formula (E-2):

$$\text{(E-2)}$$
$$X^{E4}X^{E5}X^{E6}X^{E7},$$

wherein
$X^{E4}$ is G, S, R, H, K, D, N, F, Y, or T,
$X^{E5}$ is L, I, K, H, or R,
$X^{E6}$ is G, A, S, T, P, F, or Y, and
$X^{E7}$ is G, A, D, N, S, or T.
Item 5.
An antibody or a fragment thereof (antigen-binding fragment), the antibody comprising:
heavy chain CDR1 comprising an amino acid sequence represented by formula (A-1-1):

$$\text{(A-1-1)}$$
$$GFTFX^{A51}X^{A61}X^{A71}X^{A81},$$

wherein
$X^{A51}$ is D, N, or S,
$X^{A61}$ is D, N, S, K, or H,
$X^{A71}$ is Y or W, and
$X^{A81}$ is G, W, or Y;
heavy chain CDR2 comprising an amino acid sequence represented by formula (B-1-1):

$$\text{(B-1-1)}$$
$$IX^{B21}X^{B31}X^{B41}X^{B51}X^{B61}X^{B71}X^{B81},$$

wherein
$X^{B21}$ is G, S, T, K, or N,
$X^{B31}$ is Y, L, G, T, or N,
$X^{B41}$ is G, S, T, D, or H,
$X^{B51}$ is G or S,
$X^{B61}$ is G, S, T, or D,
$X^{B71}$ is S, T, Y, D, or H, and
$X^{B81}$ is S, T, V, I, or M;
heavy chain CDR3 comprising an amino acid sequence represented by any one of formulas (C-1-1) to (C-6-1):

(C-1-1)
VRX$^{C11}$X$^{C2}$X$^{C31}$GX$^{C41}$X$^{C51}$X$^{C61}$TGFDX$^{C71}$, (C-2-1)
VRX$^{C11}$X$^{C21}$X$^{C31}$GX$^{C41}$X$^{C51}$X$^{C61}$FDX$^{C71}$, (C-3-1)
X$^{C81}$RDGALGLAVNWFDX$^{C71}$, (C-4)
ATSDDYYALNI, (C-5-1)
TTAYYSRYSYYMFDX$^{C71}$,
and (C-6-1)
TTALRDX$^{C71}$, wherein
X$^{C11}$ is A or R,
X$^{C21}$ is P or R,
X$^{C31}$ is T or I,
X$^{C41}$ is V or L,
X$^{C51}$ is P or A,
X$^{C61}$ is T or Y,
X$^{C71}$ is V, T, or N, and)
X$^{C81}$ is A or V;
light chain CDR1 comprising an amino acid sequence represented by formula (D-1-1):

(D-1-1)
QX$^{D21}$X$^{D31}$X$^{D41}$X$^{D51}$X$^{D61}$, wherein
X$^{D21}$ is G or S,
X$^{D31}$ is V or I,
X$^{D41}$ is S or K,
X$^{D51}$ is N, or K, and
X$^{D61}$ is F or Y;
light chain CDR2 comprising an amino acid sequence represented by formula (E-1-1):

(E-1-1)
X$^{E11}$X$^{E21}$X$^{E31}$, wherein
X$^{E11}$ is G, T, D, Y, or R,
X$^{E21}$ is A, T, or V, and
X$^{E31}$ is K, D, N, or S; and
light chain CDR3 comprising an amino acid sequence represented by formula (F-1-1) or (F-2-1):

(F-1-1)
(X$^{F11}$QX$^{F31}$X$^{F41}$X$^{F51}$X$^{F61}$X$^{F71}$X$^{F81}$
or (F-2-1)
(X$^{F11}$QX$^{F31}$X$^{F41}$X$^{F51}$X$^{F61}$X$^{F71}$X$^{F81}$T, wherein
X$^{F11}$ is L, Q, F, or Y,
X$^{F31}$ is S or Y,
X$^{F41}$ is G, N, Q, or Y,
X$^{F51}$ is S, N, or I,
X$^{F61}$ is G, S, Y, or W,
X$^{F71}$ is S, P, or W, and
X$^{F81}$ is L, P, H, Y, or T.

Item 6.

The antibody or a fragment thereof according to Item 5, further comprising a sequence region adjacent to the C-terminus of the light chain CDR2, the sequence region comprising an amino acid sequence represented by formula (E-2-1) or (E-2-2):

(E-2-1)
SLX$^{E61}$S
or (E-2-2)
X$^{E42}$X$^{E52}$X$^{E62}$X$^{E72}$, wherein
X$^{E61}$ is A or P,
X$^{E42}$ is R, N, Y, or T,
X$^{E52}$ is L or R,
X$^{E62}$ is A or Y, and
X$^{E72}$ is S or T.

Item 7.

The antibody or a fragment thereof according to any one of Items 3 to 6, wherein the antibody specifically binds to a 5' to 3' exonuclease domain of Taq polymerase.

Item 8.

The antibody or a fragment thereof according to any one of Items 3 to 6, wherein the antibody specifically binds to a 5' to 3' exonuclease domain of Tth polymerase.

Item 9.

The antibody or a fragment thereof according to any one of Items 3 to 6, wherein the antibody specifically binds to a 5' to 3' exonuclease domain of Z05 polymerase.

Item 10.

An antibody that specifically binds to a 5' to 3' exonuclease domain of a DNA polymerase, or a fragment thereof (antigen-binding fragment),
wherein
at least one epitope is present in
an amino acid region A selected from a region at positions 56 to 66 from the N-terminus of SEQ ID NO: 1 or a region at positions 56 to 67 from the N-terminus of SEQ ID NO: 2 or 3;
an amino acid region B selected from a region at positions 75 to 81 from the N-terminus of SEQ ID NO: 1 or a region at positions 76 to 82 from the N-terminus of SEQ ID NO: 2 or 3;
an amino acid region C selected from a region at positions 161 to 182 from the N-terminus of SEQ ID NO: 1 or a region at positions 162 to 183 from the N-terminus of SEQ ID NO: 2 or 3; or
an amino acid region D selected from a region at positions 269 to 285 from the N-terminus of SEQ ID NO: 1 or a region at positions 271 to 287 from the N-terminus of SEQ ID NO: 2 or 3.

Item 11.

The antibody or a fragment thereof according to Item 10, wherein the at least one epitope is present in the amino acid region A or B.

Item 12.

The antibody or a fragment thereof according to Item 10 or 11,
wherein
the epitope in the amino acid region A is represented by any one of SEQ ID NOs: 60 to 63, the epitope in the amino acid region B is represented by SEQ ID NO: 64 or 65, the epitope in the amino acid region C is represented by any one of SEQ ID NOs: 66 to 74, and the epitope in the amino acid region D is represented by any one of SEQ ID NOs: 75 to 83.

Item 13.

The antibody or a fragment thereof according to any one of Items 10 to 12,
wherein
the epitope in the amino acid region A is represented by SEQ ID NO: 61 or 62, the epitope in the amino acid region B is represented by SEQ ID NO: 64 or 65, the epitope in the amino acid region C is represented by SEQ ID NO: 66, 67, 68, 70, or 71, and the epitope in the amino acid region D is represented by SEQ ID NO: 77, 78, 80, or 82.

Item 14.

The antibody or a fragment thereof according to any one of Items 1 to 13, which is a monoclonal antibody or a fragment thereof.

Item 15.

The antibody or a fragment thereof according to any one of Items 1 to 14,
wherein
the heavy chain CDR3 comprises the amino acid sequence of any one of SEQ ID NOs: 21 to 28, or an amino acid sequence in which one to three amino acids are mutated in any one of these amino acid sequences, and
the light chain CDR3 comprises the amino acid sequence of any one of SEQ ID NOs: 42 to 48, or an amino acid sequence in which one to three amino acids are mutated in any one of these amino acid sequences.

Item 16.

The antibody or a fragment thereof according to any one of Items 1 to 15,
wherein
the heavy chain CDR3 comprises the amino acid sequence of any one of SEQ ID NOs: 21 to 28, and
the light chain CDR3 comprises the amino acid sequence of any one of SEQ ID NOs: 42 to 48.

Item 17.

The antibody or a fragment thereof according to any one of Items 1 to 16, comprising:
heavy chain CDR1 comprising the amino acid sequence of any one of SEQ ID NOs: 4 to 11, or an amino acid sequence in which one to three amino acids are mutated in any one of these amino acid sequences;
heavy chain CDR2 comprising the amino acid sequence of any one of SEQ ID NOs: 12 to 20, or an amino acid sequence in which one to three amino acids are mutated in any one of these amino acid sequences,
heavy chain CDR3 comprising the amino acid sequence of any one of SEQ ID NOs: 21 to 28, or an amino acid sequence in which one to three amino acids are mutated in any one of these amino acid sequences,
light chain CDR1 comprising the amino acid sequence of any one of SEQ ID NOs: 29 to 35, or an amino acid sequence in which one to three amino acids are mutated in any one of these amino acid sequences,
light chain CDR2 comprising the amino acid sequence represented by YTN, YTD, YAD, YAN, DAS, GVK, RAK, GAK, or TAS; and
light chain CDR3 comprising the amino acid sequence of any one of SEQ ID NOs: 42 to 48, or an amino acid sequence in which one to three amino acids are mutated in any one of these amino acid sequences.

Item 18.

The antibody or a fragment thereof according to any one of Items 1 to 17, comprising:
heavy chain CDR1 comprising the amino acid sequence of any one of SEQ ID NOs: 4 to 11;
heavy chain CDR2 comprising the amino acid sequence of any one of SEQ ID NOs: 12 to 20;
heavy chain CDR3 comprising the amino acid sequence of any one of SEQ ID NOs: 21 to 28;
light chain CDR1 comprising the amino acid sequence of any one of SEQ ID NOs: 29 to 35;
light chain CDR2 comprising the amino acid sequence represented by YTN, YTD, YAD, YAN, DAS, GVK, RAK, GAK, or TAS; and
light chain CDR3 comprising the amino acid sequence of any one of SEQ ID NOs: 42 to 48.

Item 19.

The antibody or a fragment thereof according to Item 17 or 18, further comprising a sequence region adjacent to the C-terminus of the light chain CDR2, the sequence region comprising the amino acid sequence of any one of SEQ ID NOs: 36 to 41, or an amino acid sequence in which one to three amino acids are mutated in any one of these amino acid sequences.

Item 20.

The antibody or a fragment thereof according to any one of Items 17 to 19, further comprising a sequence region adjacent to the C-terminus of the light chain CDR2, the sequence region comprising the amino acid sequence of any one of SEQ ID NOs: 36 to 41.

Item 21.

The antibody or a fragment thereof according to any one of Items 15, 17, and 19, wherein the mutation is a conservative substitution.

Item 22.

A fragment of the antibody of any one of Items 1 to 21, wherein the fragment is Fab, F(ab')2, or scFv (antigen-binding fragment).

Item 23.

A reagent comprising the antibody or a fragment thereof of any one of Items 1 to 21, or the fragment of Item 22.

Item 24.

The reagent according to Item 23, further comprising at least one member selected from the group consisting of a DNA polymerase having a 5' to 3' exonuclease domain, a primer, a probe, and deoxyribonucleoside-5'-phosphate.

Item 25.

The reagent according to Item 24, wherein the DNA polymerase is selected from the group consisting of Taq polymerase, Tth polymerase, and Z05 polymerase.

Item 26.

The reagent according to any one of Items 23 to 25, which is a nucleic acid amplification reagent.

Item 27.

A method for producing an antibody that specifically binds to a 5' to 3' exonuclease domain of a DNA polymerase, or a fragment thereof (antigen-binding fragment),
the method comprising
step A of selecting an antibody having binding ability for the entirety of a DNA polymerase from antibodies produced by an animal immunized with an immunogen consisting of a portion of the DNA polymerase, the portion containing a 5' to 3' exonuclease domain.

Item 28.

The production method according to Item 27, wherein the immunogen consists of the 5' to 3' exonuclease domain of the DNA polymerase.

Item 29.

The production method according to Item 27 or 28, wherein the DNA polymerase is selected from the group consisting of Taq polymerase, Tth polymerase, and Z05 polymerase.

Item 30.

The production method according to any one of Items 27 to 29, wherein the immunogen consists of a 5' to 3' exonuclease domain of Tth polymerase.

Item 31.

The production method according to Item 27, wherein step A is a step of selecting an antibody having binding ability for the entirety of Taq polymerase from antibodies produced by an animal immunized with an immunogen consisting of a portion of Tth polymerase, the portion containing a 5' to 3' exonuclease domain.

Item 32.

The production method according to Item 27, wherein step A is a step of selecting an antibody having binding ability for the entirety of Taq polymerase from antibodies produced by an animal immunized with an immunogen consisting of a 5' to 3' exonuclease domain of Tth polymerase.

Item 33.

A method for producing an antibody fragment (antigen-binding fragment),
the method comprising
expressing a portion of an amino acid sequence by genetic engineering technique based on the amino acid sequence of the antibody obtained by the production method of any one of Items 27 to 32.

Item 34.

The antibody or a fragment thereof according to any one of Items 1 to 21, or the fragment according to Item 22, having an inhibition ability for the 5' to 3' exonuclease of the DNA polymerase of 60% or more when present together at 37° C. for 24 hours with a DNA polymerase.

Item 35.

The antibody or a fragment thereof according to any one of Items 1 to 21 and 34, or the fragment according to Item 22, having a substrate DNA degradation rate of 40% or less when present together at 25° C. for 24 hours with a DNA polymerase having a 5' to 3' exonuclease domain and a substrate DNA, the substrate DNA being single or double stranded and optionally functioning as a probe.

Item 36.

A reagent for stabilizing a composition comprising a DNA polymerase having a 5' to 3' exonuclease domain and at least one nucleic acid selected from the group consisting of a primer, a probe, and a nucleic acid template, the reagent containing the antibody or a fragment thereof of any one of Items 1 to 21, 34, and 35 or the fragment of Item 22.

Item 37.

A method for stabilizing a composition comprising a DNA polymerase having a 5' to 3' exonuclease domain and at least one nucleic acid selected from the group consisting of a primer, a probe, and a nucleic acid template, the method comprising
adding the antibody or a fragment thereof of any one of Items 1 to 21, 34, and 35 or the fragment of Item 22 to the composition.

Advantageous Effects of Invention

The present invention provides an antibody that specifically binds to a 5' to 3' exonuclease domain of a DNA polymerase, or a fragment thereof, and a useful method for producing the antibody or a fragment thereof. For example, addition of the antibody or a fragment thereof to a reagent containing a DNA polymerase having a 5' to 3' exonuclease domain and nucleic acids, such as a primer and a probe, can inhibit the degradation of the nucleic acids and improve the stability of the reagent. When a target nucleic acid is amplified using this reagent, the generation of fragments due to the degradation of nucleic acids can be suppressed, thus preventing nonspecific amplification of the target nucleic acid and enabling highly efficient amplification of the target nucleic acid, which makes it possible to detect even a very small amount of the target nucleic acid with high sensitivity.

DESCRIPTION OF EMBODIMENTS

1. Definitions Etc.

In this specification, amino acids may be natural or non-natural amino acids. Examples of non-natural amino acids include, but are not limited to, citrulline, ornithine, ε-acetyl-lysine, β-alanine, aminobenzoic acid, 6-aminocaproic acid, aminobutyric acid, hydroxyproline, mercaptopropionic acid, 3-nitrotyrosine, norleucine, and pyroglutamic acid. The amino acids may be, for example, L-, D-, or DL-amino acids.

In this specification, the identity of an amino acid sequence refers to the degree of identical amino acids when two or more amino acid sequences for comparison are optimally aligned. The identity of an amino acid sequence can be calculated using analysis tools that are commercially available or available through telecommunication lines (internet). For example, the identity may be calculated using the commercially available software GENETYX (Genetyx Corporation) or using default parameters in the homology algorithm BLAST (Basic Local Alignment Search Tool) (http://www.ncbi.nlm.nih.gov/BLAST/) of the National Centre for Biotechnology Information (NCBI).

As long as binding to a 5' to 3' exonuclease domain of a DNA polymerase is not impaired, the amino acid sequences disclosed in this specification may be such that one or more (e.g., one, two, or three) amino acids are deleted, substituted, or modified in the sequence, and such that one or more (e.g., one, two, or three) amino acids are inserted or added to the sequence.

The substitution of an amino acid is preferably a substitution with another amino acid that is similar in structure and/or properties (conservative substitution). The conservative substitution may include, for example, substitutions within the groups shown in Table 1.

TABLE 1

| | | | Group |
|---|---|---|---|
| Classification by the structure of side chain | Non-aromatic group | H or unbranched hydrocarbon | Glycine (G), alanine (A) |
| | | β branched hydrocarbon | Valine (V), leucine (L), isoleucine (I) |
| | | Oxygen-containing | Serine (S), threonine (T) |

TABLE 1-continued

| | | Group |
|---|---|---|
| | Sulfur-containing | Cysteine (C), methionine (M) |
| | Nitrogen-containing | Lysine (K), arginine (R), asparagine (N), glutamine (Q), proline (P) |
| | Aromatic group | Phenylalanine (F), tryptophan (W), histidine (H), tyrosine (Y) |
| Classification by the charge/polarity of side chain | Hydrophobic, Nonpolar | Alanine (A), valine (V), leucine (L), isoleucine (I), proline (P), phenylalanine (F), methionine (M), tryptophan (W) |
| | Uncharged, Polar | Glycine (G), asparagine (N), glutamine (Q), serine (S), threonine (T), tyrosine (Y), cysteine (C) |
| | Acidic | Aspartic acid (D), glutamic acid (E) |
| | Basic | Lysine (K), arginine (R), histidine (H) |

Examples of modification of an amino acid include modification of the functional groups, such as amino, carboxyl, hydroxyl, and sulfhydryl (SH) groups. Examples of the modification of the functional groups include glycosylation; methylation; esterification; amidation; PEGylation; phosphorylation; hydroxylation; linkage of a protecting group, such as t-butoxycarbonyl (Boc) and 9-fluorenylmethyloxycarbonyl (Fmoc); biotinylation; linkage of a fluorescent dye, such as fluorescein isothiocyanate (FITC); and linkage of an enzyme, such as peroxidase (HRP) and alkaline phosphatase (ALP).

In this specification, antibodies may be monoclonal or polyclonal antibodies, and are preferably monoclonal antibodies. The antibodies may be of any isotype, such as IgG, IgA, IgD, IgE, and IgM. Examples of antibodies include, but are not limited to, mouse antibodies, rat antibodies, guinea pig antibodies, and human antibodies. The antibodies may also be chimeric antibodies, such as guinea pig-mouse chimeric antibodies and mouse-human chimeric antibodies.

In this specification, fragments of antibodies may be any fragment as long as they comprise heavy chain CDR1 to CDR3 and light chain CDR1 to CDR3. Examples include Fv, Fab, Fab', (Fab')$_2$, scFv, scFv-Fc, diabodies, triabodies, tetrabodies, and minibodies. The fragments of antibodies are preferably fragments with an antigen-binding ability (antigen-binding fragments).

In this specification, heavy chain CDR1 to CDR3 and light chain CDR1 to CDR3 are identified by homology search using IMGT/BlastSearch (http://www.imgt.org/blast/).

Nucleotides, such as DNA and RNA, may be analogues that have been subjected to known chemical modifications as described below as examples. For example, to avoid degradation by hydrolytic enzymes, such as nucleases, the phosphate residue (phosphate) of each nucleotide can be substituted with a chemically modified phosphate residue, such as phosphorothioate (PS), methylphosphonate, or phosphorodithioate. Further, the hydroxyl group at position 2 of the sugar (ribose) of each ribonucleotide may be substituted with —OR (wherein R represents, for example, —CH$_3$, —CH$_2$CH$_2$OCH$_3$, —CH$_2$CH$_2$NHC (NH) NH$_2$, —CH$_2$CONHCH$_3$, or —CH$_2$CH$_2$CN). Furthermore, the base moiety (pyrimidine, purine) can be chemically modified, for example, by introducing a methyl group or cationic functional group into position 5 of the pyrimidine base, or by substituting the carbonyl group at position 2 with thiocarbonyl. Furthermore, the phosphate moiety and hydroxyl moiety can be modified with, for example, biotin, an amino group, a lower alkylamine group, or an acetyl group.

However, the modifications are not limited to these examples.

2. Antibody that Specifically Binds to 5' to 3' Exonuclease Domain of DNA Polymerase (Referred to Below as "Domain E")

The antibody or a fragment thereof of the present invention specifically binds to domain E of a DNA polymerase, and is thus capable of inhibiting the 5' to 3' exonuclease activity. Accordingly, the antibody or a fragment thereof of the present invention is useful as a 5' to 3' exonuclease activity inhibitor (also referred to as "5' to 3' exonuclease inhibitor"). The 5' to 3' exonuclease inhibitor of the present invention, which is an antibody, has high specificity, and is advantageously easily applied to a hot-start method since the inhibitory activity can be inactivated by heating etc. The DNA polymerase may be any DNA polymerase as long as it has domain E. The DNA polymerase may be a wild-type DNA polymerase, a recombinant DNA polymerase obtained by introducing a gene encoding the DNA polymerase into any host cell, or a DNA polymerase obtained by modifying the gene. For example, the DNA polymerase may be a DNA polymerase in which domain E is fused to a DNA polymerase of a wild type that does not have domain E.

In one embodiment, the DNA polymerase is preferably a thermostable DNA polymerase. The term "thermostable" as used here refers to the property of retaining preferably 50% or more DNA polymerase activity even after heat treatment at a high temperature, such as 60° C. for 30 minutes. Examples of thermostable DNA polymerases include, but are not limited to, a DNA polymerase from *Thermus aquaticus* (Taq polymerase), a DNA polymerase from *Thermus thermophilus* HB8 (Tth polymerase), a DNA polymerase from *Thermus* sp. Z05 (Z05 polymerase), a DNA polymerase from *Bacillus* caldotenax (Bca polymerase), a DNA polymerase from *Bacillus stearothermophilus* (Bst polymerase), a DNA polymerase from *Thermococcus kodakarensis* (KOD polymerase), a DNA polymerase from *Pyrococcus furiosus* (Pfu polymerase), a DNA polymerase from *Pyrococcus woesei* (Pwo polymerase), a DNA polymerase from *Thermus brockianus* (Tbr polymerase), a DNA polymerase from *Thermus filiformis* (Tfi polymerase), a DNA polymerase from *Thermus flavus* (Tfl polymerase), a DNA polymerase from *Thermotoga maritima* (Tma polymerase), a DNA polymerase from *Thermotoga neapolitana* (Tne polymerase), a DNA polymerase from *Thermococcus litoralis* (Vent polymerase), and a DNA polymerase from *Pyrococcus* GB-D (DEEPVENT polymerase). Terms such as Taq polymerase also include mutants. A mutant as used here refers to one consisting of an amino acid sequence having 80% or more identity with the amino acid sequence of the original DNA polymerase, and in which enzymatic properties, such as polymerase activity, 5' to 3' exonuclease activity, and thermostability, are maintained. The polymerase activity domain (also referred to as "polymerase domain") of a mutant preferably consists of an amino acid sequence having 85% or more (preferably 90% or more or 95% or more) identity with the amino acid sequence of the polymerase domain of the original DNA polymerase. Domain E of a mutant preferably consists of an amino acid sequence having 85% or more (preferably 90% or more or 95% or more) identity with the amino acid sequence of domain E of the original DNA polymerase. The amino acid mutation in the mutant is preferably a conservative substitution.

In one embodiment, the DNA polymerase is preferably a DNA polymerase belonging to Family A. Examples of DNA polymerases belonging to Family A include, but are not limited to, Taq polymerase, Tth polymerase, Z05 polymerase, Tma polymerase, Bca polymerase, and Bst polymerase.

The DNA polymerase is preferably at least one member selected from the group consisting of Taq polymerase, Tth polymerase, and Z05 polymerase. In a specific embodiment, the DNA polymerase is preferably two or more DNA polymerases selected from the group consisting of Taq polymerase, Tth polymerase, and Z05 polymerase, and more preferably a combination of Taq polymerase with at least one member selected from the group consisting of Tth polymerase and Z05 polymerase.

The polymerase activity of DNA polymerase is measured as described below. However, when the polymerase activity is high, the measurement is performed as described below after a DNA polymerase solution is diluted with a preservation buffer (50 mM Tris-HCl (pH of 8.0), 50 mM KCl, 1 mM dithiothreitol, 0.1% (v/v) polyethylene glycol sorbitan monolaurate (Tween (trademark) 20), 0.1% (v/v) octylphenyl-polyethylene glycol (Nonidet (trademark) P40), 50% (v/v) glycerin).

(1) Liquid A (25 µl) described below, 5 µl of liquid B described below, 5 µl of liquid C described below, 10 µl of sterilized water, and 5 µl of a DNA polymerase solution are added to a microtube to cause a reaction at 75° C. for 10 minutes.
(2) The resulting product is cooled with ice, 50 µl of liquid E and 100 µl of liquid D are added thereto, and the mixture is stirred and then cooled with ice for another 10 minutes.
(3) The resulting liquid is filtrated through a glass filter (Whatman GF/C filter) and washed thoroughly with 0.1N hydrochloric acid and ethanol.
(4) The radioactivity of the filter is measured with a liquid scintillation counter (produced by Packard) to measure the incorporation of the nucleotide of the template DNA. One unit of polymerase activity is defined as the amount of the DNA polymerase that incorporates 10 nmol of nucleotide into an acid-insoluble fraction (i.e., a fraction that becomes insoluble when liquid D is added) per 30 minutes under these conditions.

Liquid A: 40 mM Tris-HCl buffer (pH of 7.5), 16 mM magnesium chloride, 15 mM dithiothreitol, and 100 µg/mL bovine serum albumin (BSA)
Liquid B: 1.5 µg/µl Activated calf thymus DNA
Liquid C: 1.5 mM dNTP (250 cpm/pmol [3H] dTTP)
Liquid D: 20% (w/v) Trichloroacetic acid (2 mM sodium pyrophosphate)
Liquid E: 1 mg/mL Calf thymus DNA In one embodiment, the antibody or a fragment thereof of the present invention preferably binds to at least one domain E selected from the group consisting of the amino acid sequence of SEQ ID NO: 1:

MRGMLPLFEPKGRVLLVDGHHLAYRTFHALKGLTTSRGEPVQAVYGFA

KSLLKALKEDGDAVIVVFDAKAPSFRHEAYGGYKAGRAPTPEDFPRQL

ALIKELVDLLGLARLEVPGYEADDVLASLAKKAEKEGYEVRILTADKD

LYQLLSDRIHVLHPEGYLITPAWLWEKYGLRPDQWADYRALTGDESDN

LPGVKGIGEKTARKLLEEWGSLEALLKNLDRLKPAIREKILAHMDDLK

LSWDLAKVRTDLPLEVDFAKRREPDRERLRAFLERLEFGSLLHEFGLL

ES (the amino acid sequence of domain E of Taq polymerase (wild type)),
the amino acid sequence of SEQ ID NO: 2:

MEAMLPLFEPKGRVLLVDGHHLAYRTFFALKGLTTSRGEPVQAVYGFA

KSLLKALKEDGYKAVFVVFDAKAPSFRHEAYEAYKAGRAPTPEDFPRQ

LALIKELVDLLGFTRLEVPGYEADDVLATLAKKAEKEGYEVRILTADR

DLYQLVSDRVAVLHPEGHLITPEWLWEKYGLRPEQWVDFRALVGDPSD

NLPGVKGIGEKTALKLLKEWGSLENLLKNLDRVKPENVREKIKAHLED

LRLSLELSRVRTDLPLEVDLAQGREPDREGLRAFLERLEFGSLLHEFG

LLEA (the amino acid sequence of domain E of Tth polymerase (wild type)),
the amino acid sequence of SEQ ID NO: 3:

MKAMLPLFEPKGRVLLVDGHHLAYRTFFALKGLTTSRGEPVQAVYGFA

KSLLKALKEDGYKAVFVVFDAKAPSFRHEAYEAYKAGRAPTPEDFPRQ

LALIKELVDLLGFTRLEVPGFEADDVLATLAKKAEREGYEVRILTADR

DLYQLVSDRVAVLHPEGHLITPEWLWEKYGLKPEQWVDFRALVGDPSD

NLPGVKGIGEKTALKLLKEWGSLENILKNLDRVKPESVRERIKAHLED

LKLSLELSRVRSDLPLEVDFARRREPDREGLRAFLERLEFGSLLHEFG

LLEA (the amino acid sequence of domain E of Z05 polymerase (wild type)), and
amino acid sequences having 80% or more (preferably 85% or more, 90% or more, or 95% or more) identity with these amino acid sequences.

In one embodiment, the antibody or a fragment thereof of the present invention preferably binds to (or recognizes) a portion or the entirety of any one of the four amino acid regions enclosed in square boxes in any one of the amino acid sequences of SEQ ID NOs: 1 to 3 above as at least one epitope (e.g., one, two, three, four, or five epitopes). Of the four amino acid regions enclosed in the square boxes above, the amino acid region at positions 56 to 66 from the N-terminus of SEQ ID NO: 1 or the amino acid region at positions 56 to 67 from the N-terminus of SEQ ID NO: 2 or 3 is referred to as an "amino acid region A";

the amino acid region at positions 75 to 81 from the N-terminus of SEQ ID NO: 1 or the amino acid region at positions 76 to 82 from the N-terminus of SEQ ID NO: 2 or 3 is referred to as an "amino acid region B";

the amino acid region at positions 161 to 182 from the N-terminus of SEQ ID NO: 1 or the amino acid region at positions 162 to 183 from the N-terminus of SEQ ID NO: 2 or 3 is referred to as an "amino acid region C"; and the amino acid region at positions 269 to 285 from the N-terminus of SEQ ID NO: 1 or the amino acid region at positions 271 to 287 from the N-terminus of SEQ ID NO: 2 or 3 is referred to as an "amino acid region D."

The pol I polymerase family, including Taq polymerase, is known to have multiple regions that are particularly highly conserved from the N-terminus to about position 200 (Kim Y et al., Mol. Cells, vol. 7, No. 4, pp. 468-472 (incorporated herein by reference in its entirety)). The antibody or a fragment thereof of the present invention particularly preferably binds to at least one epitope (e.g., one, two, three, four, or five epitopes) present within the region from the N-terminus to about position 200 (e.g., the amino acid regions A to C) of the pol I polymerase. From this standpoint, the antibody or a fragment thereof of the present invention preferably binds to a portion or the entirety of the amino acid region A and/or the amino acid region B as at least one epitope. In a specific embodiment, the antibody or a fragment thereof of the present invention preferably binds to at least a portion or the entirety of the amino acid region A and a portion or the entirety (in particular, a portion) of either the amino acid region C or D as epitopes. In another embodiment, the antibody or a fragment thereof preferably binds to at least a portion or the entirety (in particular, the entirely) of the amino acid region B and a portion or the entirety (in particular, a portion) of either the amino acid region C or D as epitopes.

Examples of epitopes of a portion or the entirety of the amino acid region A include, but are not limited to, EDGDAVIVVF (SEQ ID NO: 60), KEDGDAVIVVF (SEQ ID NO: 61), EDGYKAVFVVF (SEQ ID NO: 62), and KEDGYKAVFVVF (SEQ ID NO: 63). In one embodiment, the epitope of a portion or the entirety of the amino acid region A preferably comprises SEQ ID NO: 60 or 62. In a preferred embodiment, the epitope of a portion or the entirety of the amino acid region A is SEQ ID NO: 60, 61, or 62, and more preferably SEQ ID NO: 61 or 62.

Examples of epitopes of a portion or the entirety of the amino acid region B include, but are not limited to, HEAYGGY (SEQ ID NO: 64) and HEAYEAY (SEQ ID NO: 65).

Examples of epitopes of a portion or the entirety of the amino acid region C include, but are not limited to, HLITPEWLW (SEQ ID NO: 66), KYGLRPEQWVDF (SEQ ID NO: 67), EKYGLRPDQWADY (SEQ ID NO: 68), KYGLRPDQWADY (SEQ ID NO: 69), GLRPEQWVDF (SEQ ID NO: 70), ITPEWLW (SEQ ID NO: 71), YLITPAWLWEKYGLRPDQWADY (SEQ ID NO: 72), HLITPEWLWEKYGLRPEQWVDF (SEQ ID NO: 73), and HLITPEWLWEKYGLKPEQWVDF (SEQ ID NO: 74). In one embodiment, the epitope of a portion or the entirety of the amino acid region C preferably comprises SEQ ID NO: 68, 70, or 71. In a preferred embodiment, the epitope of a portion or the entirety of the amino acid region C is SEQ ID NO: 66, 67, 68, 70, or 71.

Examples of epitopes of a portion or the entirety of the amino acid region D include, but are not limited to, LERLEF (SEQ ID NO: 75), LERLEFGSLLH (SEQ ID NO: 76), LERLEFGSLLHEF (SEQ ID NO: 77), LRAFLERLEF (SEQ ID NO: 78), RAFLERLEF (SEQ ID NO: 79), RAFLERLEFGSLLH (SEQ ID NO: 80), LEFGSLLH (SEQ ID NO: 81), LEFGSLLHEF (SEQ ID NO: 82), and LRAFLERLEFGSLLHEF (SEQ ID NO: 83). In one embodiment, the epitope of a portion or the entirety of the amino acid region D preferably comprises SEQ ID NO: 75, 76, 78, 79, or 81. In a preferred embodiment, the epitope of a portion or the entirety of the amino acid region D is SEQ ID NO: 77, 78, 80, or 82.

The epitopes described above may have any length. For example, the epitope may be composed of 5 to 25 residues, preferably 6 to 20 residues, more preferably 6 to 15 residues, and still more preferably 7 to 14 residues.

In one embodiment, the heavy chain CDR1 of the antibody or a fragment thereof of the present invention preferably comprises the following amino acid sequence:
- an amino acid sequence represented by formula (A-1) shown in Table 2,
- an amino acid sequence having 90% or more (preferably 95% or more) identity with the amino acid sequence, or
- an amino acid sequence in which one to three amino acids are (preferably one or two, more preferably one amino acid is) mutated (preferably conservatively substituted) in the amino acid sequence.

TABLE 2

| $GFX^{43}X^{44}X^{45}X^{46}X^{47}X^{48}$ | $GFTFX^{451}X^{461}X^{471}X^{481}$ | GFTFDDYG |
|---|---|---|
| (A-1) | (A-1-1, SEQ ID NO: 90) | (A-1-2, SEQ ID NO: 4) |
| (In the formula, | (In the formula, | GFTFSNYY |
| $X^{43}$ is T or S, | $X^{451}$ is D, N, or S, | (A-1-3, SEQ ID NO: 5) |
| $X^{44}$ is F, L or I, | $X^{461}$ is D, N, S, K, or H, | GFTFNNYY |
| $X^{45}$ is D, N, S, or T, | $X^{471}$ is Y or W, and | (A-1-4, SEQ ID NO: 6) |
| $X^{46}$ is D, N, S, T, K, R, or H, | $X^{481}$ is G, W, or Y.) | GFTFSSYY |
| $X^{47}$ is Y, F, or W, and | | (A-1-5, SEQ ID NO: 7) |
| $X^{48}$ is G, S, T, W, Y, or F.) | | GFTFSKWY |
| | | (A-1-6, SEQ ID NO: 8) |
| | | GFTFSHYY |
| | | (A-1-7, SEQ ID NO: 9) |
| | | GFTFSNYW |
| | | (A-1-8, SEQ ID NO: 10) |
| | | GFTFSSYG |
| | | (A-1-9, SEQ ID NO: 11) |

In formula (A-1), $X^{A3}$ is preferably T, $X^{A4}$ is preferably F, $X^{A5}$ is preferably D, N, or S, $X^{A6}$ is preferably D, N, S, K, or H, or D, N, S, or H, $X^{A7}$ is preferably Y or W, or Y, and $X^{A8}$ is preferably G, W, or Y.

The heavy chain CDR1 of the antibody or a fragment thereof of the present invention preferably comprises an amino acid sequence represented by formula (A-1-1), more preferably an amino acid sequence selected from the group consisting of amino acid sequences represented by formulas (A-1-2) to (A-1-9), or an amino acid sequence having 90% or more identity with any one of these amino acid sequences. The identity is preferably 91% or more, 92% or more, 93% or more, 94% or more, or 95% or more.

In one embodiment, the heavy chain CDR2 of the antibody or a fragment thereof of the present invention preferably comprises the following amino acid sequence:

an amino acid sequence represented by formula (B-1) shown in Table 3,
an amino acid sequence having 90% or more (preferably 95% or more) identity with the amino acid sequence, or
an amino acid sequence in which one to three amino acids are (preferably one or two, more preferably one amino acid is) mutated (preferably conservatively substituted) in the amino acid sequence.

H, $X^{B5}$ is preferably G or S, or G, $X^{B6}$ is preferably G, S, T, or D, G, S, or T, or G or S, $X^{B7}$ is preferably S, T, Y, D, or H, more preferably S, T, or Y, S or T, or T, Y, D, or H, $X^{B8}$ is preferably S, T, V, I, or M, more preferably S, T, or I, S or T, or T, V, I, or M.

The heavy chain CDR2 of the antibody or a fragment thereof of the present invention preferably comprises an amino acid sequence represented by formula (B-1-1), more preferably an amino acid sequence selected from the group consisting of amino acid sequences represented by formulas (B-1-2) to (B-1-10), or an amino acid sequence having 90% or more identity with any one of these amino acid sequences. The identity is preferably 91% or more, 92% or more, 93% or more, 94% or more, or 95% or more.

In one embodiment, the heavy chain CDR3 of the antibody or a fragment thereof of the present invention preferably comprises the following amino acid sequence:

an amino acid sequence represented by any one of formulas (C-1) to (C-6) shown in Table 4,
an amino acid sequence having 90% or more (preferably 95% or more) identity with any one of these amino acid sequences, or

TABLE 3

| | | |
|---|---|---|
| $IX^{B2}X^{B3}X^{B4}X^{B5}X^{B6}X^{B7}X^{B8}$ (B-1) (In the formula, $X^{B2}$ is G, S, T, K, R, H, D, or N, $X^{B3}$ is F, Y, L, I, G, S, T, D, or N, $X^{B4}$ is G, S, T, D, N, K, R, or H, $X^{B5}$ is G, S, T, or A, $X^{B6}$ is G, S, T, D, or N, $X^{B7}$ is S, T, F, Y, D, N, K, R, or H, and $X^{B8}$ is S, T, V, L, I, or M.) | $IX^{B21}X^{B31}X^{B41}X^{B51}X^{B61}X^{B71}X^{B81}$ (B-1-1) (In the formula, $X^{B21}$ is G, S, T, K, or N, $X^{B31}$ is Y, L, G, T, or N, $X^{B41}$ is G, S, T, D, or H, $X^{B51}$ is G or S, $X^{B61}$ is G, S, T, or D, $X^{B71}$ is S, T, Y, D, or H, and $X^{B81}$ is S, T, V, I, or M.) | ISLSGGSS (B-1-2, SEQ ID NO: 12) ISNTGGST (B-1-3, SEQ ID NO: 13) ISNTGGTT (B-1-4, SEQ ID NO: 14) ISNSGSST (B-1-5, SEQ ID NO: 15) ITYHSDDM (B-1-6, SEQ ID NO: 16) ISGGGSYI (B-1-7, SEQ ID NO: 17) IKGDSSTI (B-1-8, SEQ ID NO: 18) IGGHGTHV (B-1-9, SEQ ID NO: 19) INTDGGTT (B-1-10, SEQ ID NO: 20) |

In formula (B-1), $X^{B2}$ is preferably G, S, T, K, or N, G, S, or K, or S, $X^{B3}$ is preferably Y, L, G, T, or N, more preferably L, G, or N, L or N, or Y, G, or T, $X^{B4}$ is preferably G, S, T, D, or H, more preferably G, S, T, or D, S or T, or G, D, or an amino acid sequence in which one to three amino acids are (preferably one or two, more preferably one amino acid is) mutated (preferably conservatively substituted) in any one of these amino acid sequences.

TABLE 4

| | | |
|---|---|---|
| $VRX^{C1}X^{C2}X^{C3}GX^{C4}X^{C5}$ $X^{C6}TGFDX^{C7}$ (C-1, SEQ ID NO: 84) (In the formula, $X^{C1}$ is A, S, D, K, H, or R, $X^{C2}$ is G, A, D, P, K, H, or R, $X^{C3}$ is S, T, L, Y, or I, $X^{C4}$ is A, V, I, R, or L, $X^{C5}$ is A, V, Y, or P, $X^{C6}$ is A, V, S, T, or Y, and $X^{C7}$ is V, I, L, S, T, or N.) | $VRX^{C11}X^{C21}X^{C31}GX^{C41}X^{C51}$ $X^{C61}TGFDX^{C71}$ (C-1-1, SEQ ID NO: 91) (In the formula $X^{C11}$ is A or R, $X^{C21}$ is P or R, $X^{C31}$ is T or I, $X^{C41}$ is V or L, $X^{C51}$ is P or A, $X^{C61}$ is T or Y, and $X^{C71}$ is V, T, or N.) | VRRRTGVPTTGFDV (C-1-2, SEQ ID NO: 21) |
| $VRX^{C1}X^{C2}X^{C3}GX^{C4}$ $X^{C5}X^{C6}FDX^{C7}$ (C-2, SEQ ID NO: 85) (In the formula, $X^{C1}$ is A, S, D, K, H, or R, $X^{C2}$ is G, A, D, P, K, H, or R, $X^{C3}$ is S, T, L, Y, or I, $X^{C4}$ is A, V, I, R, or L, $X^{C5}$ is A, V, Y, or P, | $VRX^{C11}X^{C21}X^{C31}GX^{C41}$ $X^{C51}X^{C61}FDX^{C71}$ (C-2-1, SEQ ID NO: 92) (In the formula, $X^{C11}$ is A or R, $X^{C21}$ is P or R, $X^{C31}$ is T or I, $X^{C41}$ is V or L, | VRAPIGVAYFDV (C-2-2, SEQ ID NO: 22) VRAPIGLAYFDT (C-2-3, SEQ ID NO: 23) |

TABLE 4-continued

| | | |
|---|---|---|
| $X^{C6}$ is A, V, S, T, or Y, and<br>$X^{C7}$ is V, I, L, S, T, or N.) | $X^{C51}$ is P or A,<br>$X^{C61}$ is T or Y, and<br>$X^{C71}$ is V, T, or N.) | |
| $X^{C8}$RDGALGLAV<br>NWFDX$^{C7}$(C-3, SEQ ID NO: 86)<br>(In the formula,<br>$X^{C7}$ is V, I, L, S, T, or N, and<br>$X^{C8}$ is A or V.) | $X^{C81}$RDGALGLAV<br>NWFDX$^{C71}$(C-3-1, SEQ ID NO: 93)<br>(In the formula,<br>$X^{C71}$ is V, T, or N, and<br>$X^{C81}$ is A or V.) | ARDGALGLAVNWFDN<br>(C-3-2, SEQ ID NO: 24)<br>VRDGALGLAVNWFDN<br>(C-3-3, SEQ ID NO: 25) |
| | ATSDDYYALNL (C-4, SEQ ID NO: 26) | |
| TTAYYSRYSYYMFDX$^{C7}$<br>(C-5, SEQ ID NO: 88)<br>(In the formula,<br>$X^{C7}$ is V, I, L, S, T, or N.) | TTAYYSRYSYYMFDX$^{C71}$<br>(C-5-1, SEQ ID NO: 94)<br>(In the formula,<br>$X^{C71}$ is V, T, or N.) | TTAYYSRYSYYMFDV<br>(C-5-2, SEQ ID NO: 27) |
| TTALRDX$^{C7}$ (C-6, SEQ ID NO: 89)<br>(In the formula,<br>$X^{C7}$ is V, I, L, S, T, or N.) | TTALRDX$^{C71}$ (C-6-1, SEQ ID NO: 95)<br>(In the formula,<br>$X^{C71}$ is V, T, or N.) | TTALRDV<br>(C-6-2, SEQ ID NO: 28) |

In formula (C-1), $X^{C1}$ is preferably A or R, more preferably R, $X^{C2}$ is preferably P or R, more preferably R, $X^{C3}$ is preferably T or I, more preferably T, $X^{C4}$ is preferably V or L, more preferably V, $X^{C5}$ is preferably P or A, more preferably P, $X^{C6}$ is preferably T or Y, more preferably T, and $X^{C7}$ is preferably V, T, or N, more preferably V.

In formula (C-2), $X^{C1}$ is preferably A or R, more preferably A, $X^{C2}$ is preferably P or R, more preferably P, $X^{C3}$ is preferably T or I, more preferably I, $X^{C4}$ is preferably V or L, $X^{C5}$ is preferably P or A, more preferably A, $X^{C6}$ is preferably T or Y, more preferably Y, and $X^{C7}$ is preferably V, T, or N, more preferably V or T.

In formula (C-3), $X^{C7}$ is preferably V, T, or N, more preferably N.

In formula (C-5), $X^{C7}$ is preferably V, T, or N, more preferably V.

In formula (C-6), $X^{C7}$ is preferably V, T, or N, more preferably V.

The heavy chain CDR3 of the antibody or a fragment thereof of the present invention preferably comprises an amino acid sequence selected from the group consisting of amino acid sequences represented by formulas (C-1-1), (C-2-1), (C-3-1), (C-4), (C-5-1), and (C-6-1), more preferably an amino acid sequence selected from the group consisting of amino acid sequences represented by formulas (C-1-2), (C-2-2), (C-2-3), (C-3-2), (C-3-3), (C-4), (C-5-2), and (C-6-2), or an amino acid sequence having 90% or more identity with any one of these amino acid sequences. The identity is preferably 91% or more, 92% or more, 93% or more, 94% or more, or 95% or more.

In one embodiment, the light chain CDR1 of the antibody or a fragment thereof of the present invention preferably comprises the following amino acid sequence:

an amino acid sequence represented by formula (D-1) shown in Table 5, an amino acid sequence having 90% or more (preferably 95% or more) identity with the amino acid sequence, or an amino acid sequence in which one to three amino acids are (preferably one or two, more preferably one amino acid is) mutated (preferably conservatively substituted) in the amino acid sequence.

TABLE 5

| | | |
|---|---|---|
| $X^{D1}X^{D2}X^{D3}X^{D4}X^{D5}X^{D6}$ (D-1)<br>(In the formula,<br>$X^{D1}$ is E, Q, D, or N,<br>$X^{D2}$ is G, A, S, or T,<br>$X^{D3}$ is A, V, L, I, or F,<br>$X^{D4}$ is S, T, K, R, or H,<br>$X^{D5}$ is S, T, D, N, K, R, or H, and<br>$X^{D6}$ is F, Y, or W.) | Q$X^{D21}X^{D31}X^{D41}X^{D51}X^{D61}$<br>(D-1-1)<br>(In the formula,<br>$X^{D21}$ is G or S,<br>$X^{D31}$ is V or I,<br>$X^{D41}$ is S or K,<br>$X^{D51}$ is S, N, or K, and<br>$X^{D61}$ is F or Y.) | QSISNY (D-1-2, SEQ ID NO: 29)<br>QSVKNY (D-1-3, SEQ ID NO: 30)<br>QSVKSY (D-1-4, SEQ ID NO: 31)<br>QSVSKY (D-1-5, SEQ ID NO: 32)<br>QGISSY (D-1-6, SEQ ID NO: 33)<br>QGISNY (D-1-7, SEQ ID NO: 34)<br>QGVSSF (D-1-8, SEQ ID NO: 35) |

In formula (D-1), $X^{D1}$ is preferably Q, $X^{D2}$ is preferably G or S, $X^{D3}$ is preferably V or I, $X^{D4}$ is preferably S or K, $X^{D5}$ is preferably S, N, or K, or S or N, and $X^{D6}$ is preferably F or Y, or Y.

The light chain CDR1 of the antibody or a fragment thereof of the present invention preferably comprises an amino acid sequence represented by formula (D-1-1), more preferably an amino acid sequence selected from the group consisting of amino acid sequences represented by formulas (D-1-2) to (D-1-8), or an amino acid sequence having 90% or more identity with any one of these amino acid sequences. The identity is preferably 91% or more, 92% or more, 93% or more, 94% or more, or 95% or more.

In one embodiment, the light chain CDR2 of the antibody or a fragment thereof of the present invention preferably comprises the following amino acid sequence:

an amino acid sequence represented by formula (E-1) shown in Table 6A, an amino acid sequence having 90% or more (preferably 95% or more) identity with the amino acid sequence, or an amino acid sequence in which one to three amino acids (preferably one or two, more preferably one amino acid) are mutated (preferably conservatively substituted) in the amino acid sequence.

In formula (E-2), $X^{E4}$ is preferably S, R, N, Y, or T, more preferably S, or R, N, Y, or T, $X^{E5}$ is preferably L or R, or L, $X^{E6}$ is preferably A, P, or Y, more preferably A or P, or A or Y, and $X^{E7}$ is preferably S or T, or S.

The C-terminus of the light chain CDR2 of the antibody or a fragment thereof of the present invention is preferably

TABLE 6A

| $X^{E1}X^{E2}X^{E3}$ (E-1) | $X^{E11}X^{E21}X^{E31}$ (E-1-1) | $X^{E12}X^{E22}X^{E32}$ (E-1-2) | YTN (E-1-4) |
|---|---|---|---|
| (In the formula, | (In the formula, | (In the formula, | YTD (E-1-5) |
| $X^{E1}$ is G, S, T, D, N, F, Y, K, | $X^{E11}$ is G, T, D, Y, or R, | $X^{E12}$ is Y, | YAD (E-1-6) |
| R, or H, | $X^{E21}$ is A, T, or V, and | $X^{E22}$ is A or T, and | YAN (E-1-7) |
| $X^{E2}$ is G, A, S, T, V, L or I, | $X^{E31}$ is K, D, N, or S.) | $X^{E32}$ is D or N.) | |
| and | | $X^{E13}X^{E23}X^{E33}$ (E-1-3) | DAS (E-1-8) |
| $X^{E3}$ is K, R, H, D, N, S, or T.) | | (In the formula, | GVK (E-1-9) |
| | | $X^{E13}$ is G, T, D, or R, | RAK (E-1-10) |
| | | $X^{E23}$ is A or V, and | GAK (E-1-11) |
| | | $X^{E33}$ is K or S.) | TAS (E-1-12) |

In formula (E-1), $X^{E1}$ is preferably G, T, D, Y, or R, more preferably G, Y, or R, or G, T, D, or R, and still more preferably Y, or G, T, D, or R, $X^{E2}$ is preferably A, T, or V, more preferably A or T, or A or V, and $X^{E3}$ is preferably K, D, N, or S, more preferably K, D, or N, or K or S, and still more preferably D or N, or K or S.

The light chain CDR2 of the antibody or a fragment thereof of the present invention preferably comprises an amino acid sequence represented by formula (E-1-1), more preferably an amino acid sequence represented by formula (E-1-2) or (E-1-3), and still more preferably an amino acid sequence selected from the group consisting of amino acid sequences represented by formulas (E-1-4) to (E-1-12), or an amino acid sequence having 90% or more identity with any one of these amino acid sequences. The identity is preferably 91% or more, 92% or more, 93% or more, 94% or more, or 95% or more.

In one embodiment, the following amino acid sequence is preferably adjacent to the C-terminus of the light chain CDR2 of the antibody or a fragment thereof of the present invention:

an amino acid sequence represented by formula (E-2) shown in Table 6B, an amino acid sequence having 90% or more (preferably 95% or more) identity with the amino acid sequence, or an amino acid sequence in which one to three amino acids are (preferably one or two, more preferably one amino acid is) mutated (preferably conservatively substituted) in the amino acid sequence.

adjacent to an amino acid sequence represented by formula (E-2-1) or (E-2-2), more preferably an amino acid sequence selected from the group consisting of amino acid sequences represented by formulas (E-2-3) to (E-2-8), or an amino acid sequence having 90% or more identity with any one of these amino acid sequences. The identity is preferably 91% or more, 92% or more, 93% or more, 94% or more, or 95% or more.

The amino acid adjacent to the N-terminus of the light chain CDR2 of the antibody or a fragment thereof of the present invention is preferably, but is not limited to, Y, F, or H. It is also preferable that these amino acids are conservatively substituted.

In one embodiment, the light chain CDR3 of the antibody or a fragment thereof of the present invention preferably comprises the following amino acid sequence:

an amino acid sequence represented by formula (F-1) or (F-2) shown in Table 7, an amino acid sequence having 90% or more (preferably 95% or more) identity with the amino acid sequence, or an amino acid sequence in which one to three amino acids are (preferably one or two, more preferably one amino acid is) mutated (preferably conservatively substituted) in the amino acid sequence.

TABLE 6B

| $X^{E4}X^{E5}X^{E6}X^{E7}$ (E-2) | $SLX^{E61}S$ (E-2-1) | SLAS (E-2-3, SEQ ID |
|---|---|---|
| (In the formula, | (In the formula, | NO: 36) |
| $X^{E4}$ is G, S, R, H, K, D, N, F, Y, or T, | $X^{E61}$ is A or P.) | SLPS (E-2-4, SEQ ID |
| $X^{E5}$ is L, I, K, H, or R, | $X^{E42}X^{E52}X^{E62}X^{E72}$ (E-2-2) | NO: 37) |
| $X^{E6}$ is G, A, S, T, P, F, or Y, and | (In the formula, | RRAT (E-2-5, SEQ ID |
| $X^{E7}$ is G, A, D, N, S, or T.) | $X^{E42}$ is R, N, Y, or T, | NO: 38) |
| | $X^{E52}$ is L or R, | NLYS (E-2-6, SEQ ID |
| | $X^{E62}$ is A or Y, and | NO: 39) |
| | $X^{E72}$ is S or T.) | YLYS (E-2-7, SEQ ID |
| | | NO: 40) |
| | | TRAT (E-2-8, SEQ ID |
| | | NO: 41) |

TABLE 7

| $X^{F1}X^{F2}X^{F3}X^{F4}X^{F5}X^{F6}X^{F7}X^{F8}$ (F-1) (In the formula, $X^{F1}$ is L, I, E, Q, F, Y, or W, $X^{F2}$ is D, N, E, or Q, $X^{F3}$ is S, T, F, or Y, $X^{F4}$ is G, S, T, F, Y, N, or Q, $X^{F5}$ is S, T, N, Q, L, or I, $X^{F6}$ is G, S, T, F, Y, or W, $X^{F7}$ is S, T, P, Y, or W, and $X^{F8}$ is L, I, P, K, R, H, Y, T or W.) | $X^{F11}QX^{F31}X^{F41}X^{F51}X^{F61}X^{F71}X^{F81}$ (F-1-1) (In the formula, $X^{F11}$ is L, Q, F, or Y, $X^{F31}$ is S or Y, $X^{F41}$ is G, N, Q, or Y, $X^{F51}$ is S, N or I, $X^{F61}$ is G, S, Y, or W, $X^{F71}$ is S, P, or W, and $X^{F81}$ is L, P, H, Y, or T.) | LQSYIYPL (F-1-2, SEQ ID NO: 42) QQYQSWPY (F-1-3, SEQ ID NO: 43) QQYQSWPH (F-1-4, SEQ ID NO: 44) YQYNSGWT (F-1-5, SEQ ID NO: 45) |
| $X^{F1}X^{F2}X^{F3}X^{F4}X^{F5}X^{F6}X^{F7}X^{F8}X^{F9}$ (F-2) (In the formula, $X^{F1}$ is L, I, E, Q, F, Y, or W, $X^{F2}$ is D, N, E, or Q, $X^{F3}$ is S, T, F, or Y, $X^{F4}$ is G, S, T, F, Y, N, or Q, $X^{F5}$ is S, T, N, Q, L, or I, $X^{F6}$ is G, S, T, F, Y, or W, $X^{F7}$ is S, T, P, Y, or W, $X^{F8}$ is L, I, P, K, R, H, Y, T or W, and $X^{F9}$ is G, S, T, D, or E.) | $X^{F11}QX^{F31}X^{F41}X^{F51}X^{F61}X^{F71}X^{F81}T$ (F-2-1) (In the formula, $X^{F11}$ is L, Q, F, or Y, $X^{F31}$ is S or Y, $X^{F41}$ is G, N, Q, or Y, $X^{F51}$ is S, N or I, $X^{F61}$ is G, S, Y, or W, $X^{F71}$ is S, P, or W, and $X^{F81}$ is L, P, H, Y, or T.) | QQYGSSPPT (F-2-2, SEQ ID NO: 46) QQYGNSPPT (F-2-3, SEQ ID NO: 47) FQYYSGSPT (F24, SEQ ID NO: 48) |

In formula (F-1), $X^{F1}$ is preferably L, Q, F, or Y, more preferably L, Q, or Y, or Q, F, or Y, and still more preferably L, Q, or Y, or Q or F, $X^{F2}$ is preferably Q, $X^{F3}$ is preferably S or Y, or Y, $X^{F4}$ is preferably G, N, Q, or Y, more preferably N, Q, or Y; G, Q, or Y; G, N, or Y; or G or Y, $X^{F5}$ is preferably S, N, or I, more preferably S or I, or S or N, $X^{F6}$ is preferably G, S, Y, or W, more preferably G, Y, or W; S, Y, or W; or G or S, $X^{F7}$ is preferably S, P, or W, more preferably P or W; S or P; or P, and $X^{F8}$ is preferably L, P, H, or Y, more preferably L, H, Y, or T, or P.

The light chain CDR3 of the antibody or a fragment thereof of the present invention preferably comprises an amino acid sequence represented by formula (F-1-1) or (F-2-1), and more preferably an amino acid sequence represented by any one of (F-1-2) to (F-1-5) and (F-2-2) to (F-2-4), or an amino acid sequence having 90% or more identity with any one of these amino acid sequences. The identity is preferably 91% or more, 92% or more, 93% or more, 94% or more, or 95% or more.

Table 8A shows suitable examples of combinations of the heavy chain CDR1 to CDR3 and light chain CDR1 to CDR3 of the antibody or a fragment thereof of the present invention.

TABLE 8A

| Combination | Heavy chain CDR1 | Heavy chain CDR2 | Heavy chain CDR3 | Light chain CDR1 | Light chain CDR2 | Light chain CDR3 |
| --- | --- | --- | --- | --- | --- | --- |
| C1 | (A-1) | (B-1) | (C-1), (C-2), (C-3), (C-4), (C-5), or (C-6) | (D-1) | (E-1) | (F-1), or (F-2) |
| C2 | (A-1-1) | (B-1-1) | (C-1-1), (C-2-1), (C-3-1), (C-4), (C-5-1), or (C-6-1) | (D-1-1) | (E-1-1) or (E-1-2) | (F-1-1), or (F-2-1) |
| C3 | (A-1-2), (A-1-3), (A-1-4), (A-1-5), (A-1-6), (A-1-7), (A-1-8), or (A-1-9) | (B-1-2), (B-1-3), (B-1-4), (B-1-5), (B-1-6), (B-1-7), (B-1-8), (B-1-9), or (B-1-10) | (C-1-2), (C-2-2), (C-2-3), (C-3-2), (C-3-3), (C-4), (C-5-2), or (C-6-2) | (D-1-2), (D-1-3), (D-1-4), (D-1-5), (D-1-6), (D-1-7), or (D-1-8) | (E-1-4), (E-1-5), (E-1-6), (E-1-7), (E-1-8), (E-1-9), (E-1-10), (E-1-11), or (E-1-12) | (F-1-2), (F-1-3), (F-1-4), (F-1-5), (F-2-2), (F-2-3), or (F-2-4) |
| C4 | (A-1-2) | (B-1-2) | (C-1-2) | (D-1-2) | (E-1-4) | (F-1-2) |
| C5 | (A-1-3) | (B-1-3) | (C-2-2) | (D-1-3) | (E-1-5) | (F-1-3) |
| C6 | (A-1-4) | (B-1-4) | (C-2-3) | (D-1-4) | (E-1-6) | (F-1-3) |
| C7 | (A-1-5) | (B-1-5) | (C-2-2) | (D-1-4) | (E-1-7) | (F-1-4) |
| C8 | (A-1-3) | (B-1-3) | (C-2-2) | (D-1-4) | (E-1-7) | (F-1-3) |
| C9 | (A-1-6) | (B-1-6) | (C-4) | (D-1-5) | (E-1-8) | (F-1-5) |
| C10 | (A-1-7) | (B-1-7) | (C-3-2) | (D-1-5) | (E-1-9) | (F-2-2) |
| C11 | (A-1-8) | (B-1-8) | (C-5-2) | (D-1-6) | (E-1-10) | (F-2-3) |

TABLE 8A-continued

| Combination | Heavy chain CDR1 | Heavy chain CDR2 | Heavy chain CDR3 | Light chain CDR1 | Light chain CDR2 | Light chain CDR3 |
|---|---|---|---|---|---|---|
| C12 | (A-1-3) | (B-1-9) | (C-3-3) | (D-1-7) | (E-1-11) | (F-2-2) |
| C13 | (A-1-9) | (B-1-10) | (C-6-2) | (D-1-8) | (E-1-12) | (F-2-4) |

Table 8B shows suitable examples of combinations of the heavy chain CDR1 to CDR3, light chain CDR1 to CDR3, and sequence adjacent to the C-terminus of the light chain CDR2 of the antibody or a fragment thereof of the present invention.

prising an amino acid sequence having 80% or more (preferably 85% or more, 90% or more, or 95% or more) identity with any one of these amino acid sequences.

The equilibrium dissociation constant ($K_D$) of the antibody or a fragment thereof of the present invention for

TABLE 8B

| Combination | Heavy chain CDR1 | Heavy chain CDR2 | Heavy chain CDR3 | Light chain CDR1 | Light chain CDR2 | Sequence adjacent to light chain CDR2 | Light chain CDR3 |
|---|---|---|---|---|---|---|---|
| C14 | (A-1) | (B-1) | (C-1), (C-2), (C-3), (C-4), (C-5), or (C-6) | (D-1) | (E-1) | (E-2) | (F-1), or (F-2) |
| C15 | (A-1-1) | (B-1-1) | (C-1-1), (C-2-1), (C-3-1), (C-4), (C-5-1), or (C-6-1) | (D-1-1) | (E-1-1) or (E-1-2) | (E-2-1) or (E-2-2) | (F-1-1), or (F-2-1) |
| C16 | (A-1-2), (A-1-3), (A-1-4), (A-1-5), (A-1-6), (A-1-7), (A-1-8), or (A-1-9) | (B-1-2), (B-1-3), (B-1-4), (B-1-5), (B-1-6), (B-1-7), (B-1-8), (B-1-9), or (B-1-10) | (C-1-2), (C-2-2), (C-2-3). (C-3-2), (C-3-3), (C-4), (C-5-2), or (C-6-2) | (D-1-2), (D-1-3), (D-1-4), (D-1-5), (D-1-6), (D-1-7), or (D-1-8) | (E-1-4), (E-1-5), (E-1-6), (E-1-7), (E-1-8), (E-1-9), (E-1-10), (E-1-11), or (E-1-12) | (E-2-3), (E-2-4), (E-2-5), (E-2-6), (E-2-7), or (E-2-8) | (F-1-2), (F-1-3), (F-1-4), (F-1-5), (F-2-2), (F-2-3), or (F-2-4) |
| C17 | (A-1-2) | (B-1-2) | (C-1-2) | (D-1-2) | (E-1-4) | (E-2-3) | (F-1-2) |
| C18 | (A-1-3) | (B-1-3) | (C-2-2) | (D-1-3) | (E-1-5) | (E-2-4) | (F-1-3) |
| C19 | (A-1-4) | (B-1-4) | (C-2-3) | (D-1-4) | (E-1-6) | (E-2-3) | (F-1-3) |
| C20 | (A-1-5) | (B-1-5) | (C-2-2) | (D-1-4) | (E-1-7) | (E-2-3) | (F-1-4) |
| C21 | (A-1-3) | (B-1-3) | (C-2-2) | (D-1-4) | (E-1-7) | (E-2-3) | (F-1-3) |
| C22 | (A-1-6) | (B-1-6) | (C-4) | (D-1-5) | (E-1-8) | (E-2-5) | (F-1-5) |
| C23 | (A-1-7) | (B-1-7) | (C-3-2) | (D-1-5) | (E-1-9) | (E-2-6) | (F-2-2) |
| C24 | (A-1-8) | (B-1-8) | (C-5-2) | (D-1-6) | (E-1-10) | (E-2-7) | (F-2-3) |
| C25 | (A-1-3) | (B-1-9) | (C-3-3) | (D-1-7) | (E-1-11) | (E-2-6) | (F-2-2) |
| C26 | (A-1-9) | (B-1-10) | (C-6-2) | (D-1-8) | (E-1-12) | (E-2-8) | (F-2-4) |

In terms of combinations of C14 to C26, it is also preferred that one to three amino acids are (preferably one or two, more preferably one amino acid is) mutated (preferably conservatively substituted) in at least one amino acid sequence of the sequences of the heavy chain CDR1 to CDR3 and light chain CDR1 to CDR3, and the sequence adjacent to the C-terminus of the light chain CDR2.

Regions other than the heavy chain CDR1 to CDR3 and light chain CDR1 to CDR3 may have any amino acid sequence as long as they can be used for antibodies. Examples of constant regions for use include, but are not limited to, the constant regions of IgG1, IgG2, IgG3, IgA1, IgA2, and IgM. The constant regions may be constant regions from any animal including, for examples, mammals, such as mice, hamsters, rats, guinea pigs, rabbits, ferrets, goats, monkeys, and humans. Examples include the amino acid sequences of SEQ ID NOs: 51 and 52 (heavy and light chain constant regions from guinea pigs), the amino acid sequences of SEQ ID NOs: 53 and 54 (heavy and light chain constant regions from mouse), and sequence regions comprising an amino acid sequence having 80% or more (preferably 85% or more, 90% or more, or 95% or more) identity with any one of these amino acid sequences.

domain E of a DNA polymerase is, for example, 50 nM or less, and preferably 10 nM or less, and is, for example, 1 pM or more. The $K_D$ can be measured, for example, using Biacore (trademark) X100 (Cytiva) as described in the Examples below. Specifically, the $K_D$ can be calculated as follows. Specifically, a ligand (a DNA polymerase having a 5' to 3' exonuclease domain) is immobilized on the carboxymethyl dextran on CM5 sensor chip (Cytiva) through an amine coupling reaction with NHS (N-hydroxysuccinimide) and EDC (N-ethyl-N'-(3-dimethylaminopropyl)carbodiimide hydrochloride), followed by blocking with a 1M ethanolamine hydrochloride solution to prepare flow cells in which the ligand is immobilized. Subsequently, serially diluted antibodies are added to the flow cells to analyze the reaction signal.

In one embodiment, when the antibody or a fragment thereof of the present invention is present together with a DNA polymerase at 37° C. for 24 hours, the inhibition ability for the 5' to 3' exonuclease activity of the DNA polymerase is, for example, 50% or more, and preferably 60% or more, 70% or more, 80 or more, or 90% or more. The inhibition ability can be calculated according to the following formula by measuring the radioactivity of a labeled base released when a solution containing the following components is incubated at 37° C. for 24 hours, as described in the Examples below.

Radioisotope-labeled substrate nucleic acid ADNA;

A DNA polymerase alone (1 unit (U)), or a DNA polymerase (1 U) and the antibody or a fragment thereof of the present invention (0.005 μg/μl);

10 mM Tris-HCl (pH of 8.6);

50 mM KCl; and 1.5 mM MgCl$_2$.

Inhibition ability for 5' to 3' exonuclease activity
(%)=(N2−N3)/(N2−N1)×100

N1: The amount of free nucleotides before incubation at 37° C. for 24 hours of a solution that does not contain the antibody or a fragment thereof of the present invention (or after incubation at −20° C. for 24 hours), or the amount of free nucleotides after incubation at 37° C. of 24 hours of a solution that does not contain the antibody or a fragment thereof of the present invention, nor a DNA polymerase N2: The amount of free nucleotides after incubation at 37° C. for 24 hours of a solution that does not contain the antibody or a fragment thereof of the present invention N3: The amount of free nucleotides after incubation at 37° C. for 24 hours of a solution that contains the antibody or a fragment thereof of the present invention In another embodiment, when the antibody or a fragment thereof is present together at 25° C. for 24 hours with a substrate DNA (which may be single or double stranded and may optionally function as a probe) and a DNA polymerase, the inhibition ability for the 5' to 3' exonuclease activity of the DNA polymerase (an ability to inhibit the degradation of the substrate DNA) can also be confirmed quantitatively, for example, according to the following method (1) or (2).

(1) The Ct values in real-time PCR are compared between a reaction liquid after exposure at 25° C. for 24 hours, the reaction liquid containing the antibody or a fragment thereof of the present invention together with a fluorescent-labeled substrate DNA (e.g., a fluorescent-labeled probe), and a control reaction liquid (a reaction liquid after exposure at −20° C. for 24 hours or before exposure at 25° C. for 24 hours in the absence of the antibody or a fragment thereof of the present invention). A smaller difference in the Ct values means a higher inhibition ability for the 5' to 3' exonuclease activity of the DNA polymerase.

(2) The fluorescence intensities at the initial stage of the cycles in real-time PCR are compared between a reaction liquid after exposure at 25° C. for 24 hours, the reaction liquid containing the antibody or a fragment thereof of the present invention together with a fluorescent-labeled substrate DNA (e.g., a fluorescent-labeled probe), and a control reaction liquid (a reaction liquid after exposure at −20° C. for 24 hours or before exposure at 25° C. for 24 hours in the absence of the antibody or a fragment thereof of the present invention). A smaller difference in the fluorescence intensities means a higher inhibition ability for the 5' to 3' exonuclease activity of the DNA polymerase.

The reaction liquid for use in (1) and (2) may be, for example, a reaction liquid containing the following components:
the antibody or a fragment thereof of the present invention (0.06 μg/μl);
Taq polymerase of SEQ ID NO: 49 (0.05 U/μL);
an anti-polymerase antibody for hot start PCR (0.01 μg/μl);
10 mM Tris-HCl (pH of 8.3);
50 mM KCl;
1.5 mM MgCl$_2$;
0.3 mM dNTPs;
cDNA from RNA of HeLa cells (5 ng/μL); and
a primer-and-probe solution (1/20 amount of the total liquid amount), or a reaction liquid containing the following components:
the antibody or a fragment thereof of the present invention (0.06 μg/μl);
Tth polymerase of SEQ ID NO: 50 or Z05 polymerase of SEQ ID NO: 55 (0.05 U/μL);
an anti-polymerase antibody for hot start PCR (0.01 μg/μl);
10 mM Tris-HCl (pH of 8.3);
80 mM KCl;
1.5 mM MgCl$_2$;
0.5 mg/mL BSA;
0.1% (v/v) Triton X-100;
0.1% (w/v) sodium cholate;
0.3 mM dNTPs;
cDNA from RNA of HeLa cells (5 ng/μL); and
a primer-and-probe solution (1/20 amount of the total liquid amount).

The primer-and-probe solution for use in the reaction liquids above may be, for example, the following: TaqMan (registered trademark) gene expression assays produced by Thermo Fisher Scientific K.K.

[Genes:
interleukin 6, Assay ID: Hs00985639_m1 (abbreviated below as "IL6"),
cyclin-dependent kinase 10, Assay ID: Hs00177586_m1 (abbreviated below as "CDK10"),
APC, WNT signaling pathway regulator, Assay ID: Hs01568269_m1 (abbreviated below as "APC"),
mitogen-activated protein kinase 8, Assay ID: Hs00177083_m1 (abbreviated below as "MAPK8"),
SIVA1 apoptosis inducing factor, Assay ID: Hs00276002_m1 (abbreviated below as "SIVA1"),
ribosomal protein S19, Assay ID: Hs03044115_g1 (abbreviated below as "RPS19"), or
serpin family B member 5, Assay ID: Hs00985285_m1 (abbreviated below as "SERPINB5"]

The reaction liquids above preferably satisfy one, two, or three of the following items (a) to (c).

(a) Ct value before exposure at 25° C. for 24 hours (or after exposure at −20° C. for 24 hours)/Ct value after exposure at 25° C. for 24 hours≥0.8

(b) Fluorescence intensity at the initial stage of the cycles before exposure at 25° C. for 24 hours (or after exposure at −20° C. for 24 hours)/fluorescence intensity at the initial stage of the cycles after exposure at 25° C. for 24 hours≥0.3

(in the formula, the fluorescence intensity at the initial stage of the cycles indicates the fluorescence intensity in real-time PCR before the amplification curve starts up, and the initial stage of the cycles usually indicates cycles 1 to 30)

(c) Fluorescent-labeled substrate DNA degradation rate≥40% (in the formula, the fluorescent-labeled substrate DNA degradation rate can be calculated according to the following formula:

Fluorescent-labeled substrate DNA degradation rate (%)=$(F_{13}-F_{11})/(F_{12}-F_{11}) \times 100$ $F_{11}$: fluorescence intensity at the initial stage of the cycles before exposure at 25° C. for 24 hours (or after exposure at −20° C. for 24 hours) without the antibody or a fragment thereof of the present invention $F_{12}$: fluorescence intensity at the initial stage of the cycles after exposure at 25° C. for 24 hours without the antibody or a fragment thereof of the present invention $F_{13}$: fluorescence intensity at the initial stage of the cycles after exposure at 25° C. for 24 hours with the antibody or a fragment thereof of the present invention)

The value in (a) above (Ct value ratio) is preferably 0.9 or more. The value in (b) above (fluorescence intensity ratio) is preferably 0.35 or more, more preferably 0.5 or more, and still more preferably 0.7 or more. The value in (c) above (fluorescent-labeled substrate DNA degradation rate) is preferably 30% or less, more preferably 20% or less.

In still another embodiment, when the antibody or a fragment thereof of the present invention is present together at 25° C. or 37° C. for 24 hours with a substrate DNA (which may be single or double stranded and may optionally function as a probe) and a DNA polymerase, the inhibition ability for the 5' to 3' exonuclease activity of the DNA polymerase (an ability to inhibit the degradation of substrate DNA) can also be confirmed quantitatively, for example, according to the following method (3) or (4).

(3) The band intensities of the substrate DNA after gel electrophoresis are compared between a solution after exposure at 25° C. for 24 hours, the solution containing the antibody or a fragment thereof of the present invention together with a substrate DNA (e.g., a double-stranded substrate DNA), and a control solution (a solution after exposure at −20° C. for 24 hours or before exposure at 25° C. for 24 hours in the absence of the antibody or a fragment thereof of the present invention). A smaller difference in the band intensities means a higher inhibition ability for the 5' to 3' exonuclease activity of the DNA polymerase.

(4) The fluorescence intensities at the initial stage of the cycles in real-time PCR or fluorescence intensities measured by spectrophotometer are compared between a reaction liquid after exposure at 37° C. for 24 hours, the reaction liquid containing the antibody or a fragment thereof of the present invention together with a fluorescent-labeled substrate DNA (e.g., a double-stranded substrate DNA with at least one strand being fluorescently labeled), and a control reaction liquid (a reaction liquid after exposure at −20° C. for 24 hours or before exposure at 37° C. for 24 hours in the absence of the antibody or a fragment thereof of the present invention). A smaller difference in the fluorescence intensities means a higher inhibition ability for the 5' to 3' exonuclease activity of the DNA polymerase.

The solution or reaction liquid for use in (3) or (4) may be, for example,
a solution or reaction liquid containing the following components:
 the antibody or a fragment thereof of the present invention (0.06 µg/µl);
 Taq polymerase of SEQ ID NO: 49 (0.05 U/µL);
 an anti-polymerase antibody for hot start PCR (0.01 µg/µl);
 10 mM Tris-HCl (pH of 8.3);
 50 mM KCl;
 1.5 mM MgCl$_2$; and
 0.3 pM substrate DNA;
or
a solution or reaction liquid containing the following components:
 the antibody or a fragment thereof of the present invention (0.06 µg/µl);
 Tth polymerase of SEQ ID NO: 50 or Z05 polymerase of SEQ ID NO: 55 (0.05 U/µL);
 an anti-polymerase antibody for hot start PCR (0.01 µg/µl);
 10 mM Tris-HCl (pH of 8.3);
 50 mM KCl;
 1.5 mM MgCl$_2$; and
 0.3 µM substrate DNA.

In the method (3), the substrate DNA may or may not be labeled with a fluorescent dye, radioisotope, or the like. In terms of the substrate DNA, examples of double-stranded substrate DNAs include, but are not limited to, a double-stranded substrate DNA in which the 3' terminus of at least one chain protrudes beyond the 5' terminus of the other chain, such as the combination of SEQ ID NO: 56 and SEQ ID NO: 57. The base length of the protruding moiety is, for example, about 3 to 10 base long. Examples of gel electrophoresis techniques include, but are not limited to, agarose gel electrophoresis and polyacrylamide gel electrophoresis. It is preferable to use an apparatus that can quantify the band intensity of nucleic acids. Examples of the apparatus include, but are not limited to, a microchip electrophoresis system for DNA/RNA analysis (MultiNA, Shimadzu Corporation) or a fully automated high-throughput electrophoresis system (TapeStation series, Agilent Technologies Japan, Ltd.).

In the method (4), the substrate DNA is preferably fluorescently labeled. In terms of the substrate DNA, examples of double-stranded substrate DNAs include, but are not limited to, a double-stranded substrate DNA in which the 3' terminus of at least one chain protrudes beyond the 5' terminus of the other chain, and at least one terminus of the other chain is fluorescently labeled, such as the combination of SEQ ID NO: 58 and SEQ ID NO: 59. The base length of the protruding moiety is, for example, about 3 to 10 base long. For example, changes in fluorescence values can be measured by, without limitation, a real-time PCR device or spectrophotometer.

The above solution or reaction liquid preferably satisfies one or two of the following items (d) and (e).
(d) Substrate DNA degradation rate≤40%
(in the formula, the substrate DNA degradation rate can be calculated according to the following formula:

Substrate DNA degradation rate (%)=$(S_{11}-S_{13})/(S_{11}-S_{12}) \times 100$ $S_{11}$: band intensity before exposure at 25° C. for 24 hours (or after exposure at −20° C. for 24 hours) without the antibody or a fragment thereof of the present invention $S_{12}$: band intensity after exposure at 25° C. for 24 hours without the antibody or a fragment thereof of the present invention $S_{13}$: band intensity after exposure at 25° C. for 24 hours with the antibody or a fragment thereof of the present invention)

(e) Fluorescent-labeled substrate DNA degradation rate≤40% (in the formula, the fluorescent-labeled substrate DNA degradation rate can be calculated according to the following formula:

Fluorescent-labeled substrate DNA degradation rate (%)=$(F_{23}-F_{21})/(F_{22}-F_{21}) \times 100$)

$F_{21}$: fluorescence intensity at the initial stage of the cycles before exposure at 37° C. for 24 hours (or after exposure at −20° C. for 24 hours) without the antibody or a fragment thereof of the present invention $F_{22}$: fluorescence intensity at the initial stage of the cycles after exposure at 37° C. for 24 hours without the antibody or a fragment thereof of the present invention $F_{23}$: fluorescence intensity at the initial stage of the cycles after exposure at 37° C. for 24 hours with the antibody or a fragment thereof of the present invention Initial stage of the cycles: usually cycles 1 to 30

Fluorescence intensity: fluorescence intensity during the real-time PCR)

The substrate DNA degradation rate in (d) above is preferably 30% or less, and more preferably 20% or less. The fluorescent-labeled substrate DNA degradation rate in (e) above is preferably 30% or less, and more preferably 20% or less.

Even when the antibody or a fragment thereof of the present invention is present together, for example, at 25° C. for 24, 48, or 72 hours, or at 37° C. for 24 hours with a DNA polymerase and nucleic acids, such as a nucleic acid template, a primer, and a probe, the antibody or a fragment thereof of the present invention is capable of inhibiting the degradation of the nucleic acids caused by the 5' to 3' exonuclease activity of the DNA polymerase. Thus, the antibody or a fragment thereof of the present invention can be suitably used to improve the stability of nucleic acid amplification reagents, etc.

The antibody or a fragment thereof of the present invention can be obtained, for example, by immunizing an animal with an immunogen consisting of a portion of a DNA polymerase, the portion containing domain E, or consisting of the entire DNA polymerase. The immunogen preferably consists of a portion of a DNA polymerase, the portion containing domain E, more preferably consists of a portion of at least one DNA polymerase selected from the group consisting of Taq polymerase, Tth polymerase, and Z05 polymerase, the portion containing domain E, and still more preferably a portion of Tth polymerase, the portion containing domain E. Examples of animals include, but are not limited to, mammals, such as mice, hamsters, rats, guinea pigs, rabbits, ferrets, goats, monkeys, and humans.

The antibodies of the present invention can be obtained by screening antibodies produced by the animal immunized with the immunogen mentioned above. For example, when the immunogen consists of a portion of a DNA polymerase, the portion containing domain E, the screening may be performed using the binding ability for the entire DNA polymerase as an indicator. Alternatively, when the immunogen consists of the entire DNA polymerase, screening may be performed using the binding ability for a portion of the DNA polymerase, the portion containing domain E, or using the difference between the binding ability for the entire DNA polymerase and the binding ability for portions other than the portion of the DNA polymerase, the portion containing domain E, as an indicator. In one embodiment, it is preferred to use an immunogen consisting of a portion of a DNA polymerase, the portion containing domain E, and perform screening using the binding ability for the entire DNA polymerase as an indicator. It is more preferred to use an immunogen consisting of a portion of Tth polymerase, the portion containing domain E, and perform screening using the binding ability for the entire DNA polymerase as an indicator.

Specific examples of usable screening methods include a hybridoma method, in which mammalian spleen cells are fused to myeloma cells, and a phage display method, in which antibodies with affinity for a target molecule are selected from an antibody phage library. The screening method may also be a method comprising sorting antigen-specific plasma cells from immunized animals, and isolating antibody genes (full length or part of variable regions, etc.) to obtain a recombinant antibody with high affinity for antigen.

Examples of methods for sorting antigen-specific plasma cells include the method described in U.S. Patent Application Publication No. 2014/031528 (incorporated herein by reference in its entirety), and the method described in U.S. Patent Application Publication No. 2018/292407 (incorporated herein by reference in its entirety). In the former method, a cell suspension solution prepared from an immune animal is subjected to the action of a fluorescent-labeled antigen and a fluorescent dye with endoplasmic reticulum affinity, and an antibody expressed on the cell surface is fluorescently labeled, whereby antigen-specific plasma cells can be identified. In the latter method, a cell population containing antibody-producing cells is subjected to fixing treatment with a crosslinking agent and cell membrane lysis treatment with a surfactant to bind the antibody expressed inside the cells to a fluorescent-labeled antigen, whereby antigen-specific plasma cells can be identified. In these methods, at least one plasma cell binding to a target antigen can be separated by performing single-cell analysis using a cell sorter. Further, in these methods, fluorescent probes of high dye selectivity for the endoplasmic reticulum of cells can be used to distinguish plasma cells and plasmablasts from other cells. For such fluorescent probes, for example, those described in US Patent Application Publication No. 2013/029325 (incorporated herein by reference in its entirety) may be used.

Examples of the method for obtaining antibody genes from antigen-specific plasma cells include, but are not limited to, a hybridoma method and antibody gene cloning. The latter method may be, for example, a method comprising extracting mRNA from antigen-specific plasma cells, performing reverse transcription, and synthesizing cDNA to obtain antibody genes. The method described in U.S. Patent Application Publication No. 2011/020879 (incorporated herein by reference in its entirety) may also be used. In this method, mRNA is extracted from antigen-specific plasma cells using magnetic beads to obtain antibody genes by RT-PCR. This method uses a reaction device, optionally comprises a washing step, and can perform multiple sequential reactions, such as cDNA synthesis from mRNA and DNA amplification, in parallel.

The method for obtaining recombinant antibodies from antibody genes may be, for example, a method comprising constructing an antibody expression vector that contains an antibody gene and expressing an antibody from the antibody expression vector. Examples of such methods include the method described in U.S. Patent Application Publication No. 2013/023009 (incorporated herein by reference in its entirety) and the method described in U.S. Patent Application Publication No. 2011/117609 (incorporated herein by reference in its entirety). The former method permits the specific production of a joined DNA fragment containing a sequence derived from a desired target gene by causing one or more double-stranded DNA fragments to bind to a PCR amplification product containing a target gene sequence without purifying the PCR amplification product. In the latter method, a sequence of an amplification primer and an internal sequence of the amplification primer sequence that only exists in a target gene are added to homologous recombination regions existing on both ends of a linearized vector, thereby target DNA fragments can be selectively subjected to homologous recombination to construct a vector.

The antibody or a fragment thereof of the present invention may also be obtained by genetic engineering techniques based on the amino acid sequence information of antibodies or fragments thereof obtained by the above methods. For example, the antibody or a fragment thereof of the present invention may be obtained by expressing in any host cell known in this field an expression vector comprising an antibody gene designed such that the amino acid sequences of the light chain CDR1 to CDR3 and optionally the region adjacent to the C-terminus of the light chain CDR2 respectively have 80% or more identity with the amino acid sequences of the light chain CDR1 to CDR3 and optionally the region adjacent to the C-terminus of the light chain CDR2 of the antibody obtained by the above methods, and such that the amino acid sequences of the heavy chain CDR1 to CDR3 respectively have 80% or more identity with the amino acid sequences of the heavy chain CDR1 to CDR3 of the antibody obtained by the above methods.

3. Polynucleotide

The polynucleotide of the present invention preferably comprises the coding sequence of the antibody or a fragment thereof described above in section 2.

In one embodiment, the polynucleotide of the present invention preferably comprises an expression cassette of the antibody or a fragment thereof described above in section 2. The expression cassette may be any expression cassette as long as it allows expression in host cells, and comprises, for example, a promoter and a coding sequence placed under the control of the promoter.

The promoter may be any promoter and can be appropriately selected according to the type of the host cells. The promoter for use may be, for example, any pol II promoter. Examples of pol II promoters include, but are not limited to, a CMV promoter, EF1 promoter, SV40 promoter, and MSCV promoter. In addition, examples of promoters include a tryptophan promoter, such as trc and tac; lac promoter; T7 promoter; T5 promoter; T3 promoter; SP6 promoter; arabinose-induced promoter; cold-shock promoter; and tetracycline-induced promoter.

The expression cassette may comprise other elements as necessary. Examples of other elements include multiple cloning sites (MCS), drug resistance genes, replication origins, enhancer sequences, repressor sequences, insulator sequences, reporter protein-coding sequences, and drug resistance-gene-coding sequences. These may be used alone or in a combination of two or more.

The polynucleotide of the present invention can be, for example, in the form of a vector. An appropriate vector is selected according to the purpose of use, host cell type, etc. Examples of vectors that use *E. coli* as the host include M13 phage or a variant thereof, λ phage or a variant thereof, and pBR322 or a variant thereof (e.g., pB325, pAT153, pUC8). Examples of vectors that use yeast as the host include pYepSec1, pMFa, pYES2, and pPIC3.5K. Examples of vectors that use insect cells as the host include pAc and pVL. Examples of vectors that use mammalian cells as the host include pcDNA, pCDM8, and pMT2PC.

4. Cell

The cell of the present invention preferably comprises the polynucleotide described above in section 3. Examples of cells include *Escherichia coli*, such as *Escherichia coli* K12, *Bacillus* bacteria, such as *Bacillus subtilis* MI114, yeasts, such as *Saccharomyces cerevisiae* AH22, Sf cell line from *Spodoptera frugiperda* or High Five cell line from *Trichoplusia ni*, and insect cells and animal cells, such as olfactory nerve cells. The animal cells are preferably cultured cells derived from mammals. Specific examples include COS7 cells, CHO cells, HEK293 cells, Expi293 cells, 293F cells, 293T cells, 293FT cells, Hela cells, PC12 cells, N1E-115 cells, and SH-SYSY cells.

In one embodiment, the cell of the present invention is preferably a cell expressing an antibody that specifically binds to domain E of a DNA polymerase, or a fragment thereof.

In one embodiment, the cell of the present invention is preferably secreting or having on the cell surface an antibody that specifically binds to domain E of a DNA polymerase, or a fragment thereof.

5. Reagent

The reagent of the present invention preferably comprises the antibody or a fragment thereof described in section 2 above, the polynucleotide described in section 3 above, or the cell described in section 4 above. The reagent of the present invention preferably further comprises an excipient or a carrier and/or an additive.

Examples of the excipient or carrier include starch, lactose, crystalline cellulose, sorbitol, calcium hydrogen phosphate, water, ethanol, (poly)ethylene glycol, (poly)propylene glycol, glycerol, and vegetable oil. These may be used alone or in a combination of two or more.

Examples of the additive include a buffering agent, a tonicity agent, a thickener, a chelating agent, an emulsifier, a coloring agent, and a preservative. These may be used alone or in a combination of two or more.

The reagent of the present invention is preferably a nucleic acid amplification reagent.

In one embodiment, the reagent of the present invention preferably comprises a DNA polymerase having domain E and an antibody that specifically binds to domain E of the DNA polymerase, or a fragment thereof. The molar ratio of the antibody or a fragment thereof to the DNA polymerase may be any ratio as long as the effect of the present invention is achieved. The molar ratio is preferably about 1:1 to about 500:1. The reagent may further comprise a DNA polymerase that does not have domain E. The reagent is preferably a nucleic acid amplification reagent.

In one embodiment, it is preferred that the reagent of the present invention comprises at least one member selected from the group consisting of a DNA polymerase having domain E, a primer, a probe, and deoxyribonucleoside-5'-phosphate, and comprises an antibody that specifically binds to domain E of a DNA polymerase (preferably an antibody that binds to at least one epitope (e.g., one or two epitopes) present in any one of the amino acid regions A to D in domain E), or a fragment thereof. The reagent may further comprise, for example, a metal salt, such as manganese or magnesium, a buffering agent, and the like in order to improve the DNA polymerase activity. The reagent is preferably a nucleic acid amplification reagent.

When the reagent of the present invention comprises a DNA polymerase having domain E, the DNA polymerase may be, for example, those described in section 2 above.

When the reagent of the present invention comprises a primer, the primer may be at least two types of primers. The at least two types of primers may be oligonucleotides that are substantially complementary to a nucleic acid sequence to be amplified, and additionally, may be those that define both ends of the nucleic acid sequence to be amplified and function as a template for further synthesis when the extension product synthesized from each primer is separated from its complement. The primers for use may be any primer and may be appropriately selected or designed according to the target nucleic acid. When the target nucleic acid is assumed to be a subtype, the primers may be degenerate primers. Typically, the primers may be oligonucleotides with 12 to 60 nucleotides. The primers can be synthesized by a DNA synthesizer or isolated from a biological source.

When the reagent of the present invention comprises a probe, the probe may be a hybridization probe labeled with at least one labeling substance. By using such a probe, the nucleic acid amplification product can be analyzed by monitoring the fluorescent signal without using the usual electrophoresis, which reduces the labor for analysis. Furthermore, it is not necessary to open the reaction vessel, which can further reduce the risk of contamination. For example, it is also possible to identify subtypes of target nucleic acids by labeling hybridization probes with different fluorescent dyes corresponding to the subtypes of the nucleic acid sequences to be detected. Examples of hybridization probes include TaqMan hydrolysis probes (U.S. Pat. Nos. 5,210,015, 5,538, 848, 5,487,972, and U.S. Pat. No. 5,804,375 (incorporated herein by reference in their entirety)), molecular beacons (U.S. Pat. No. 5,118,801 (incorporated herein by reference in its entirety)), and FRET hybridization probes (WO97/46707, WO97/46712, and WO97/46714 (incorporated herein by reference in their entirety)).

Instead of the probe, the reagent of the present invention may comprise a fluorescent compound binding to a double-stranded DNA. Examples of the fluorescent compound binding to a double-stranded DNA include, but are not limited to, SYBR (registered trademark) Green I, SYBR (registered trademark) Gold, SYTO-9, SYTP-13, and SYTO-82 (Life Technologies), EvaGreen (registered trademark, Biotium), LCGreen (Idaho), and LightCycler (registered trademark) 480 ResoLight (Roche Applied Science).

When the reagent of the present invention comprises deoxyribonucleoside-5'-phosphate, the deoxyribonucleoside-5'-phosphate is, for example, dATP, dCTP, dTTP, dGTP, or a mixture thereof. The terms, such as "dATP," also encompass those that have been chemically modified.

When the reagent of the present invention is a nucleic acid amplification reagent, examples of nucleic acid amplification methods include, but are not limited to, PCR methods, loop-mediated isothermal amplification (LAMP) methods, transcription-reverse transcription concerted reaction (TRC) methods, and nucleic acid sequence-based amplification (NASBA) methods. The nucleic acid amplification method is preferably a PCR method. Among PCR methods, for example, a PCR method in which primer annealing is inhibited up to a predetermined temperature with a monoclonal antibody specific for a DNA polymerase, i.e., a hot-start PCR method, is preferable. The reagent for hot start PCR of the present invention when comprising a combination of an antibody that specifically binds to a polymerase domain of a DNA polymerase and an antibody that specifically binds to domain E of a DNA polymerase is capable of suppressing non-specific reactions more effectively. The reagent for hot start PCR of the present invention preferably comprises a primer, deoxyribonucleoside-5'-phosphate, a DNA polymerase, an antibody that specifically binds to the polymerase domain of the DNA polymerase, and an antibody that specifically binds to domain E of the DNA polymerase. When this reagent is mixed with a reagent comprising a target nucleic acid, and the resulting mixture is heated to 60° C. or higher (e.g., heated at 95° C. for 20 seconds or more) to inactivate both of the antibodies, a primer extension product can be obtained.

EXAMPLES

The present invention is described below in more detail with reference to Test Examples. However, the present invention is not limited to the Test Examples.

Test Example 1: Production of Antigen

When the entirety of a DNA polymerase was used as an antigen, Taq polymerase having the amino acid sequence of SEQ ID NO: 49 (TAP-201; Toyobo Co., Ltd.; hereinafter referred to as "whole Taq"), and Tth polymerase having the amino acid sequence of SEQ ID NO: 50 (TTH-301; Toyobo Co., Ltd.; hereinafter referred to as "whole Tth") were used. The sequence identity between whole Taq and whole Tth was about 87%.

When domain E of a DNA polymerase was used as an antigen, a polypeptide having the amino acid sequence of SEQ ID NO: 1 (from the N-terminus to the 290th amino acid of whole Taq) (hereinafter referred to as "Taq exo"), and a polypeptide having the amino acid sequence of SEQ ID NO: 2 (from the N-terminus to the 292nd amino acid of whole Tth) (hereinafter referred to as "Tth exo") were expressed using E. coli JM109 strain and purified by heparin-Sepharose chromatography for use. All of the antigens were dissolved in phosphate buffer.

Test Example 2: Immunization of Guinea Pig

Antigen preparations (each 0.8 mL) each containing 400 μg of an antigen were individually injected subcutaneously in the back (lower back) of Slc:Hartley guinea pigs (7-week-old male). The antigen preparations were obtained by mixing each of the antigen solutions obtained by dissolving the antigens in phosphate buffer in Test Example 1, with Titer-Max Gold adjuvant (TiterMax) at 1:1 (liquid volume ratio) to form emulsions. After 3 weeks, booster immunization was performed by further injecting 0.8 mL of each antigen preparation containing 400 μg of antigen. After another 3 weeks, booster immunization was performed by injecting 0.4 mL of each antigen preparation containing 400 μg of antigen. The lymph node swelling of the immunized guinea pigs increased in the order of whole Taq, Taq exo, whole Tth, and Tth exo.

Test Example 3: Production of Fluorescent-Labeled Protein

The entire DNA polymerases and DNA polymerases lacking domain E were fluorescently labeled. The DNA polymerases lacking domain E were obtained by individually expressing Taq polymerase in which amino acids from the N-terminus to the 289th amino acid were deleted in SEQ ID NO: 49 (hereinafter referred to as "ΔTaq") and Tth polymerase in which amino acids from the N-terminus to the 291st amino acid were deleted in SEQ ID NO: 50 (hereinafter referred to as "ΔTth") using E. coli JM109 strain, and purifying them by heparin-Sepharose chromatography.

Whole Taq and whole Tth were fluorescently labeled with DyLight (trademark) 488 NHS Ester (Thermo Fisher Scientific). ΔTaq and ΔTth were fluorescently labeled with DyLight (trademark) 550 NHS Ester (Thermo Fisher Scientific).

Test Example 4: Isolation of Domain E-Specific Plasma Cell and Construction of Antibody Expression Vector Cell suspensions were prepared from iliac lymph nodes of the guinea pigs immunized in Test Example 2, and domain E-specific plasma cells were selected using flow cytometer, by the methods described in US Patent Application Publication No. 2014/031528, US Patent Application Publication No. 2018/292407, and US Patent Application Publication No. 2013/029325. The selection of domain E-specific plasma cells was performed by the following five methods, using different combinations of the antigens used for immunization and the fluorescent-labeled proteins prepared in Test Example 3.

Method 1

Domain E-specific plasma cells were selected from cells immunized with whole Taq by subtraction using DyLight 488-labeled whole Taq and DyLight 550-labeled ΔTaq. Specifically, plasma cells in which fluorescence corresponding to DyLight 488 was confirmed and in which fluorescence corresponding to DyLight 550 was not confirmed were selected.

Method 2

Domain E-specific plasma cells were selected from cells immunized with Taq exo using DyLight 488-labeled whole Taq.

Method 3

Domain E-specific plasma cells were selected from cells immunized with Tth exo using DyLight 488-labeled whole Taq.

Method 4

Domain E-specific plasma cells were selected from cells immunized with whole Tth by subtraction using DyLight 488-labeled whole Tth and DyLight 550-labeled ΔTth. Specifically, plasma cells in which fluorescence corresponding to DyLight 488 was confirmed and in which fluorescence corresponding to DyLight 550 was not confirmed were selected.

Method 5

Domain E-specific plasma cells were selected from cells immunized with Tth exo using DyLight 488-labeled whole Tth.

The number of plasma cells selected using domain E of Taq polymerase as a target was greater in method 3 than in methods 1 and 2; in method 3, 288 plasma cells were selected. The number of plasma cells selected using domain E of Tth polymerase as a target was 192 in method 4 and 240 in method 5.

Antibody expression vectors were constructed using the plasma cells selected in methods 3 to 5 by the methods described in US Patent Application Publication No. 2011/020879, US Patent Application Publication No. 2013/023009, and US Patent Application Publication No. 2011/117609. In constructing antibody expression vectors, the amino acid sequences set forth in SEQ ID NOs: 51 and 52 were used for the guinea pig heavy and light chain constant regions, respectively. From method 3, 22 antibody expression vectors were obtained; from method 4, 9 antibody expression vectors were obtained; and from method 5, 66 antibody expression vectors were obtained.

When methods 3 to 5 were used, the guinea pig lymph nodes were more swollen and the number of isolated plasma cells was greater than when methods 1 and 2 were used, indicating that Tth polymerase induced a greater immune response as an antigen than Taq polymerase. This result shows that the use of Tth polymerase as an antigen enables domain E-specific plasma cells to be efficiently selected for both Taq polymerase and Tth polymerase. Further, when method 5 was used, the number of isolated plasma cells and the number of antibody expression vectors obtained were greater than when method 4 was used. This result shows that antibodies that specifically bind to domain E (anti-domain E antibodies) can be obtained more efficiently when immunization is performed with domain E alone than when immunization is performed with the entire DNA polymerase.

In the Test Examples below, antibodies obtained by expressing the antibody expression vectors obtained by using methods 3 to 5 were used.

Test Example 5: Evaluation of Binding Ability of Antibody to Domain E

The antibody expression vectors were introduced into 293FT cells, and culture supernatants in which antibodies were secreted were collected, by the method described in US Patent Application Publication No. 2018/292407. A commercially available hot-start antibody (TCP-101; produced by Toyobo Co., Ltd.) was immobilized on an ELISA plate (Sumitomo Bakelite Co., Ltd.; MS-8896F) using carbonate buffer. After the wells were washed, blocking was performed using 1×TBS (Nacalai Tesque, Inc.) containing 1% (w/v) bovine serum albumin (globulin-free, Nacalai Tesque, Inc.). After the wells were washed, antigens (whole Taq, whole Tth) diluted with 1×TBS-T (Nacalai Tesque, Inc.) were added to the wells. After the wells were washed, the culture supernatants were added to the respective wells. After the wells were washed, Goat Anti-Guinea pig IgG H&L (HRP) (Abcam) was 50000-fold diluted and added. After the wells were washed, a TMB solution (TMBW-1000-01, Surmodics) was added to develop color, and the reaction was stopped by adding 1 N sulfuric acid (Nacalai Tesque, Inc.), followed by measurement of wavelengths of 450 to 620 nm with a plate reader. In this binding ability evaluation, since the DNA polymerase domain is occupied by the immobilized antibodies, the binding ability of the antibodies to domain E is evaluated.

Of the 22 antibodies obtained by using method 3, 20 antibodies bound to whole Taq (hit rate: 91%), and 19 antibodies bound to both whole Taq and whole Tth (hit rate: 86%).

Of the nine antibodies obtained by using method 4, one antibody bound to whole Tth (hit rate: 11%), and this antibody did not show binding to whole Taq.

Of 66 antibodies obtained by using method 5, 32 antibodies bound to whole Tth (hit rate: 48%), and 12 antibodies bound to both whole Tth and whole Taq (hit rate: 18%).

In the case of using method 3, the hit rate for each DNA polymerase and the hit rate for both DNA polymerases were approximately 2 to 8 times higher than in the cases of using method 4 and using method 5. This result shows that the method of selecting domain E-specific plasma cells using Tth Exo, which strongly induces immune response, as an antigen and using fluorescent-labeled whole Taq is efficient in obtaining antibodies that specifically bind to domain E of Taq polymerase. It was also found that the method of selecting domain E-specific plasma cells using Tth Exo as an antigen and using fluorescent-labeled whole Tth produces an unexpected effect in terms of obtaining antibodies that specifically bind to domain E of Tth polymerase, enabling isolation of domain E-specific antibodies with high probability.

Test Example 6: Degradation of Probe Due to DNA Polymerase Having Domain E

It was confirmed that when a PCR reaction liquid containing a DNA polymerase having domain E was exposed at 25° C. for 24 hours, the probe was degraded.

(1) Components of PCR Reaction Liquid
PCR Mix
PCR mix 1 having the following composition was prepared. PCR Mix 1:
Taq polymerase (0.05 U/µL; TAP-201; produced by Toyobo Co., Ltd.);
anti-polymerase antibody for hot-start PCR (0.01 µg/µl; TCP-101; produced by Toyobo Co., Ltd.);
10 mM Tris-HCl (pH 8.3);
50 mM KCl;
1.5 mM $MgCl_2$; and
0.3 mM dNTPs
Primer/Probe
TaqMan (registered trademark) Gene Expression Assays (Thermo Fisher Scientific) were used as primer/probe mixtures at a 20-fold concentration. The genes amplified/detected by the primers/probes in the mixtures were IL6, CDK10, APC, MAPK8, SIVA1, RPS19, and SERPINB5.
Nucleic Acid Template
cDNA produced from HeLa cell (derived from human cervical cancer) RNA was used. For RNA extraction and cDNA synthesis, Human HeLa Cell Total RNA (636543; Takara Bio Inc.) and SuperPrep (trademark) II Cell Lysis & RT Kit for qPCR (SCQ-401; Toyobo Co., Ltd.) were used. The procedure was performed according to the instruction manual.
(2) Reaction
Each primer/probe set and the nucleic acid template were each mixed with PCR mix 1 in an amount that is 1/20th of the total liquid volume to prepare PCR reaction liquids (each 20 µL). The PCR reaction liquids were stored at −20° C. or 25° C. for 24 hours. Thereafter, reactions were performed in the following temperature cycles with a real-time PCR device (Applied Biosystems 7500 Fast Real-Time PCR System). Fluorescence readings were performed in the extension step at 60° C. for 60 seconds.
Temperature Cycle
Step 1: 95° C. 1 min
Step 2: 95° C. 15 sec-60° C. 60 sec, 50 cycles (PCR)
(3) Results
In this reaction system, each gene was detected in FAM channel. Table 9 shows the Ct values in detecting the genes (IL6, CDK10, APC, MAPK8, SIVA1, RPS19, and SERPINB5) in HeLa cDNA and the fluorescence values at the 10th cycle in multicomponent data, obtained using real-time PCR.

When the PCR reaction liquids were exposed at 25° C. for 24 hours, there were delays of 2 or more in the Ct values for the IL6, CDK10, and SIVA1 genes compared with when they were exposed at −20° C. for 24 hours, and no Ct value was calculated for the RPS19 gene (indicated by "–" in the table of the results). The reason why no Ct value was calculated for the RPS19 gene is presumably because the probe was entirely degraded, resulting in no increase in the fluorescence value corresponding to the amplification products.

When the PCR reaction liquids were exposed at 25° C. for 24 hours, the fluorescence values at the 10th cycle for all of the seven genes were higher than when they were exposed at −20° C. for 24 hours. The reason for the higher fluorescence values is presumably because the fluorescent-labeled probes underwent degradation before the start of the cycles due to exposure at 25° C. for 24 hours to release the fluorescent label, resulting in elimination of quenching by the quencher to generate fluorescence. It was thus found that all of the fluorescent-labeled probes that detect the seven genes are degraded when exposure is performed at 25° C. for 24 hours.

TABLE 9

|  |  | Gene name | | | | | | |
| --- | --- | --- | --- | --- | --- | --- | --- | --- |
|  |  | IL6 | CDK10 | APC | MAPK8 | SIVA1 | RPS19 | SERPINB5 |
| Ct value | −20° C./24 h | 27.6 | 31.1 |  |  | 24.8 | 21.9 | 30.3 |
|  | 25° C./24 h | 33.1 | 34.7 |  |  | 27.1 | — | 31.6 |
| Fluorescence value | −20° C./24 h | 382128 | 172415 | 360414 | 152963 | 126552 | 449992 | 358082 |
|  | 25° C./24 h | 929396 | 1002497 | 677449 | 652429 | 743985 | 1142201 | 817910 |

Test Example 7: Suppression of Probe Degradation by Anti-Domain E Antibody

It was confirmed whether an anti-domain E antibody suppresses probe degradation when a PCR reaction liquid containing a DNA polymerase having domain E and the anti-domain E antibody is exposed at 25° C. for 24 hours.
(1) Preparation of Anti-Domain E Antibody
The antibody expression vectors obtained by using the methods disclosed in Test Examples 1 to 4 were introduced into 293FT cells, and culture supernatants in which antibodies were secreted were collected, by the method described in US Patent Application Publication No. 2018/292407. The culture supernatants were passed through HiTrap Protein A HP columns (Cytiva) to adsorb the antibodies using AKTA pure 25 (Cytiva). The columns were washed with wash buffer (20 mM phosphate buffer; pH: 7.4), followed by elution with elution buffer (0.1 M citric acid-NaOH; pH: 3.5). The antibodies were concentrated using Amicon Ultra-15 (Merck), and quantified with NanoDrop One (Thermo Fisher Scientific). Clone numbers Anti-TAQ 1 to Anti-TAQ 5 are anti-domain E antibodies obtained by using method 3 of Test Example 4, and clone numbers Anti-TTH 1 to Anti-TTH 5 are anti-domain E antibodies obtained by using method 5 of Test Example 4.
(2) Components of PCR Reaction Liquid
PCR Mix
The same PCR mix 1 as that used in Test Example 6 was used. Further, the following two PCR mixes 2 and 3 were prepared and used.
PCR Mix 2:
Tth polymerase (0.05 U/µL; TTH-301; produced by Toyobo Co., Ltd.);
anti-polymerase antibody for hot-start PCR (0.01 µg/µl; TCP-101; produced by Toyobo Co., Ltd.);
10 mM Tris-HCl (pH 8.3);
80 mM KCl;
1.5 mM $MgCl_2$;
0.5 mg/mL BSA;
0.1% (v/v) Triton X-100;

0.1% (w/v) sodium cholate; and
0.3 mM dNTPs

PCR Mix 3:
Tth polymerase (mutant) described in WO2018/096961 (0.05 U/μL);
anti-polymerase antibody for hot-start PCR (0.01 μg/μl; TCP-101; produced by Toyobo Co., Ltd.);
10 mM Tris-HCl (pH 8.3);
80 mM KCl;
1.5 mM MgCl$_2$;
0.5 mg/mL BSA;
0.1% (v/v) Triton X-100;
0.1% (w/v) sodium cholate; and
0.3 mM dNTPs Primer/Probe TaqMan (registered trademark) Gene Expression Assays (Thermo Fisher Scientific) were used as a primer/probe mixture at a 20-fold concentration. The gene amplified/detected by the primers/probe in the mixture was RPS19.

Nucleic Acid Template cDNA produced from HeLa cell (derived from human cervical cancer) RNA was used. For RNA extraction and cDNA synthesis, Human HeLa Cell Total RNA (636543; Takara Bio Inc.) and SuperPrep (trademark) II Cell Lysis & RT Kit for qPCR (SCQ-401; Toyobo Co., Ltd.) were used. The procedure was performed according to the instruction manual.

(3) Reaction

Reaction Liquid 1

The primer/probe set and the nucleic acid template were each mixed with PCR mix 1 in an amount that is 1/20th of the total liquid volume to prepare 19 μL of a mixture. As a control, 1 μL of 20 mM Tris-HCl (pH 7.5) was added to the mixture, followed by exposure at −20° C. or 25° C. for 24 hours. Also as a control, 1 μL of Platinum Taq Monoclonal Antibody (10965-028; Thermo Fisher Scientific) was added to the mixture, followed by exposure at 25° C. for 24 hours. For each anti-domain E antibody, 1 μL of a 0.8 mg/mL solution thereof (amount brought in: 0.8 μg) was added to the mixture, followed by exposure at 25° C. for 24 hours.

Reaction Liquid 2

The primer/probe set and the nucleic acid template were each mixed with PCR mix 2 in an amount that is 1/20th of the total liquid volume to prepare 19 μL of a mixture. As a control, 1 μL of 20 mM Tris-HCl (pH 7.5) was added to the mixture, followed by exposure at −20° C. or 25° C. for 24 hours. For each anti-domain E antibody, 1 μL of a 1.2 mg/mL solution thereof (amount brought in: 1.2 μg) was added to the mixture, followed by exposure at 25° C. for 24 hours.

Reaction Liquid 3

The primer/probe set and the nucleic acid template were each mixed with PCR mix 3 in an amount that is 1/20th of the total liquid volume to prepare 19 μL of a mixture. As a control, 1 μL of 20 mM Tris-HCl (pH 7.5) was added to the mixture, followed by exposure at −20° C. or 25° C. for 24 hours. For each anti-domain E antibody, 1 μL of a 1.2 mg/mL solution thereof (amount brought in: 1.2 μg) was added to the mixture, followed by exposure at 25° C. for 24 hours.

Reaction

Reactions were performed using reaction liquids 1 to 3 in the following temperature cycles with a real-time PCR device (Applied Biosystems 7500 Fast Real-Time PCR System). Fluorescence readings were performed in the extension step at 60° C. for 60 seconds.

Temperature Cycle
Step 1: 95° C. 1 min
Step 2: 95° C. 15 sec-60° C. 60 sec, 50 cycles (PCR)

(4) Results

Tables 10, 11, and 12 show the Ct values in detecting the RPS19 gene and the fluorescence values at the 10th cycle in multicomponent data, in the cases of using reaction liquids 1, 2, and 3, respectively. Table 13 shows the sequences of heavy chain (H chain) complementarity determining regions (CDRs) 1 to 3 and light chain (L chain) complementarity determining regions (CDRs) 1 to 3 of Anti-TAQ 1 to Anti-TAQ 5 and Anti-TTH 1 to Anti-TTH 5, and the sequences adjacent to the C-terminus of the L chain CDR2.

When reaction liquid 1 containing Tris-HCl was exposed at 25° C. for 24 hours, there was a delay of about 5 to 6 in the Ct value for the RPS19 gene, compared with when it was exposed at −20° C. for 24 hours, indicating that the detection sensitivity was reduced about $2^5$- to $2^6$-fold. In contrast, when reaction liquids 1 to which each anti-domain E antibody was individually added were used, the Ct values were all below 30. Furthermore, all of the anti-domain E antibody clones satisfied probe degradation suppression indexes (a) to (c):

(a) Ct value ratio [Ct value measured after exposure at −20° C. for 24 hours (corresponding to before exposure at 25° C. for 24 hours)/Ct value measured after exposure at 25° C. for 24 hours]≥0.8

(b) fluorescence intensity ratio [fluorescence intensity at the initial stage of the cycles measured after exposure at −20° C. for 24 hours (corresponding to before exposure at 25° C. for 24 hours)/fluorescence intensity at the initial stage of the cycles measured after exposure at 25° C. for 24 hours]≥0.3

(c) probe degradation rate [$(F_{33}-F_{31})/(F_{32}-F_{31})\times 100$] ≤40%

$F_{31}$: fluorescence intensity at the initial stage of the cycles measured after exposure at −20° C. for 24 hours (corresponding to before exposure at 25° C. for 24 hours) in the absence of an anti-domain E antibody $F_{32}$: fluorescence intensity at the initial stage of the cycles measured after exposure at 25° C. for 24 hours in the absence of the anti-domain E antibody $F_{33}$: fluorescence intensity at the initial stage of the cycles measured after exposure at 25° C. for 24 hours in the presence of the anti-domain E antibody It was thus found that all of the anti-domain E antibody clones have a probe degradation suppression effect.

When reaction liquid 2 containing Tris-HCl was exposed at 25° C. for 24 hours, the RPS19 gene could not be detected. In contrast, the RPS19 gene was detected in all of the cases of using reaction liquids 2 to which each anti-domain E antibody was individually added. It was also found that all of the anti-domain E antibody clones satisfy probe degradation suppression indexes (a) to (c) and have a probe degradation suppression effect. Anti-TTH 2 and Anti-TTH 3 were found to exhibit the effect in even reaction liquid 1, which contains Taq.

When reaction liquid 3 containing Tris-HCl was exposed at 25° C. for 24 hours, the RPS19 gene could not be detected. In contrast, the RPS19 gene was detected in all of the cases of using reaction liquids 3 to which each anti-domain E antibody was individually added. It was found that all of the anti-domain E antibody clones satisfy probe degradation suppression indexes (a) to (c) and have a probe degradation suppression effect. In reaction liquids 3, the probe degradation suppression index (b) was greatly above 1, and the probe degradation suppression index (c) was greatly above 100%, when each anti-domain E antibody was individually added. This is presumably because during the preparation of the control reagent or during setting in the real-time PCR device, the reaction liquid reached room temperature, and the fluorescent-labeled probe was degraded. Accordingly, these antibodies can suppress the degradation of probes in reaction liquids not only during long-term storage of the reaction liquids, but also during the preparation of common nucleic acid amplification reagents.

TABLE 10

| Control | −20° C./24 h | 25° C./24 h | Platinum Taq Antibody |
|---|---|---|---|
| Ct value | 24.9 | 30.5 | 38.4 |
| Fluorescence value | 118525 | 893963 | 1055881 |
| (a) Ratio of Ct values before and after storage | — | 0.79 | 0.71 |
| (b) Ratio of fluorescence intensities before and after storage | — | 0.12 | 0.11 |
| (c) Probe degradation rate (%) | 0 | 100 | 111 |

| Clone No. | Anti-TAQ1 | Anti-TAQ2 | Anti-TAQ3 | Anti-TAQ4 | Anti-TAQ5 | Anti-TTH2 | Anti-TTH3 |
|---|---|---|---|---|---|---|---|
| Ct value | 26.5 | 24.5 | 24.4 | 24.1 | 24.5 | 25.1 | 27.8 |
| Fluorescence value | 310124 | 374937 | 274781 | 330541 | 380719 | 399935 | 315014 |
| (a) Ratio of Ct values before and after storage | 0.94 | 1.01 | 1.02 | 1.03 | 1.01 | 0.99 | 0.89 |
| (b) Ratio of fluorescence intensities before and after storage | 0.39 | 0.32 | 0.44 | 0.37 | 0.32 | 0.30 | 0.38 |
| (c) Probe degradation rate (%) | 22 | 30 | 18 | 25 | 30 | 33 | 23 |

TABLE 11

| Control | −20° C./24 h | 25° C./24 h |
|---|---|---|
| Ct value | 29.4 | n.d. |
| Fluorescence value | 382968 | 1085575 |
| (a) Ratio of Ct values before and after storage | — | 0.73 |
| (b) Ratio of fluorescence intensities before and after storage | — | 0.28 |
| (c) Probe degradation rate (%) | 0 | 100 |

| Clone No. | Anti-TTH1 | Anti-TTH2 | Anti-TTH4 | Anti-TTH5 |
|---|---|---|---|---|
| Ct value | 29.3 | 30.2 | 29.5 | 29.5 |
| Fluorescence value | 383319 | 399576 | 448323 | 333866 |
| (a) Ratio of Ct values before and after storage | 0.99 | 0.96 | 0.98 | 0.98 |
| (b) Ratio of fluorescence intensities before and after storage | 0.76 | 0.73 | 0.65 | 0.87 |
| (c) Probe degradation rate (%) | 14 | 18 | 14 | 6 |

TABLE 12

| Control | −20° C./24 h | 25° C./24 h |
|---|---|---|
| Ct value | 23.3 | n.d. |
| Fluorescence value | 266199 | 1104373 |
| (a) Ratio of Ct values before and after storage | — | 0.58 |
| (b) Ratio of fluorescence intensities before and after storage | — | 0.24 |
| (c) Probe degradation rate (%) | 0 | 100 |

| Clone No. | Anti-TTH1 | Anti-TTH2 | Anti-TTH4 | Anti-TTH5 |
|---|---|---|---|---|
| Ct value | 23.8 | 25.8 | 23.8 | 29.0 |
| Fluorescence value | 201522 | 196316 | 202495 | 213829 |

TABLE 12-continued

| | | | | |
|---|---|---|---|---|
| (a) Ratio of Ct values before and after storage | 0.98 | 0.90 | 0.98 | 0.80 |
| (b) Ratio of fluorescence intensities before and after storage | 1.29 | 1.48 | 1.44 | 1.36 |
| (c) Probe degradation rate (%) | −7 | −8 | −7 | −6 |

TABLE 13

| Clone No. | Heavy chain (H chain) | | | Light chain (L chain) | | Sequences adjacent to the C-terminus of | |
|---|---|---|---|---|---|---|---|
| | CDR1 | CDR2 | CDR3 | CDR1 | CDR2 | CDR2 | CDR3 |
| Anti-TAQ1 | GFTFDDYG (A-1-2, SEQ ID NO: 4) | ISLSGGSS (B-1-2, SEQ ID NO: 12) | VRRRTGVPTTGFDV (C-1-2, SEQ ID NO: 21) | QSISNY (D-1-2, SEQ ID NO: 29) | YIN (E-1-4) | SLAS (E-2-3 SEQ ID NO: 36) | LQSYIPL (F-1-2 SEQ ID NO: 42) |
| Anti-TAQ2 | GFTFSNYY (A-1-3, SEQ ID NO: 5) | ISNTGGST (B-1-3, SEQ ID NO: 13) | VRAPIGVAYFDV (C-2-2, SEQ ID NO: 22) | QSVKNY (D-1-3, SEQ ID NO: 30) | YTD (E-1-5) | SLPS (E-2-4, SEQ ID NO: 37) | QQYQSWPY (F-1-3, SEQ ID NO: 43) |
| Anti-TAQ3 | GFTFNNYY (A-1-4, SEQ ID NO: 6) | ISNTGGTT (B-1-4, SEQ ID NO: 14) | VRAPIGLAYFDT (C-2-3, SEQ ID NO:23) | QSVKSY (D-1-4, SEQ ID NO: 31) | YAD (E-1-6) | SLAS (E-2-2, SEQ ID NO: 36) | QQYQSWPY (F-1-3, SEQ ID NO: 43) |
| Anti-TAQ4 | GFTFSSYY A-1-5, SEQ ID NO: 7 | ISNSGSST (B-1-5, SEQ ID NO: 15) | VRAPIGVAYFDV (C-2-2, SEQ ID NO: 22) | QSVKSY (D-1-4, SEQ ID NO: 31) | YAN (E-1-7) | SEAS (E-2-3, SEQ ID NO: 36) | QQYQSWPH (F-1-4, SEQ ID NO: 44) |
| Ant-TAQ5 | GFTFSNYY (A-1-3, SEQ ID NO: 5) | ISNTGGST (B-1-3, SEQ ID NO: 13) | VRAPIGVAYFDV (C-2-2, SEQ ID NO: 22) | QSVKSY (D-1-4, SEQ ID NO: 31) | YAN (E-1-7) | SEAS (E-2-3, SEQ ID NO: 36) | QQYQSWPY (F-1-3, SEQ ID NO: 43) |
| Anti-TTH1 | GFTFSKWY (A-1-6, SEQ ID NO: 8) | ITYHSDDM (B-1-6, SEQ ID NO: 16) | ATSDDYYALNI (C-4, SEQ ID NO: 26) | QSVSKY (D-1-5, SEQ ID NO: 32) | DAS (E-1-8) | RRAT (E-2-5, SEQ ID NO: 38) | YQYNSGWT (F-1-5, SEQ ID NO: 45) |
| Anti-TTH2 | GFTFSHYY (A-1-7, SEQ ID NO: 9) | ISGGGSYI (B-1-7, SEQ ID NO: 17) | ARDGALGLAVNWFDN (C-3-2, SEQ ID NO: 24) | QGISSY (D-1-6, SEQ ID NO: 33) | GVK (E-1-9) | NLYS (E-2-6, SEQ ID NO: 39) | QQYGSSPPT (F-2-2, SEQ ID NO: 46) |
| Anti-TTH3 | GFTFSNYW (A-1-8, SEQ ID NO: 10) | IKGDSSTI (B-1-8, SEQ ID NO: 18) | TTAYYSRYSYYMFDV (C-5-2, SEQ ID NO: 27) | QGISSY (D-1-6, SEQ ID NO: 33) | RAK (E-1-10) | YLYS (E-2-7, SEQ ID NO: 40) | QQYGNSPPT (F-2-3, SEQ ID NO: 47) |
| Ati-TTH4 | GFTFSNYY (A-1-3, SEQ ID NO: 5) | IGGHGTHV (B-1-9, SEQ ID NO: 19) | VRDGALGLAVNWNFDN (C-3-3, SEQ ID NO: 25) | QGISNY (D-1-7, SEQ ID NO: 34) | GAK (E-1-11) | NLYS (E-2-6, SEQ ID NO: 39) | QQYGSSPPT (F-2-2, SEQ ID NO: 46) |
| Ati-TH5 | GFTFSSYG (A-1-9, SEQ ID NO: 11) | INTDGGTT (B-1-10, SEQ ID NO: 20) | TTALRDV (C-6-2, SEQ ID NO: 28) | QGVSSF (D-1-3, SEQ ID NO: 25) | TAS (E-1-12) | TRAT (E-2-8, SEQ ID NO: 41) | FQYYSGSPT (F-2-4, SEQ ID NO: 48) |

Test Example 8: Effect of Exposure Time of PCR Reaction Liquid at 25° C.

The probe degradation suppression effect of anti-domain E antibodies was confirmed by varying the exposure time of PCR reaction liquids at 25° C.

delay in the CT values was observed even when the reaction liquids were exposed at 25° C. for 72 hours. Furthermore, no increase in the fluorescence values was observed, indicating that the addition of the anti-domain E antibodies suppressed probe degradation. It was thus confirmed that the use of the antibodies allows storage of PCR reaction liquids even under conditions of 25° C. for 72 hours.

TABLE 14

| | | Clone No. | — | — | Anti-TAQ1 | | | Anti-TAQ2 | | | Anti-TAQ5 | | |
|---|---|---|---|---|---|---|---|---|---|---|---|---|---|
| | | Steals temperature (° C.) | −20 | | | | | 25 | | | | | |
| | | Storage time (h) | 24 | 24 | 24 | 48 | 72 | 24 | 48 | 72 | 24 | 48 | 72 |
| Gene name | IL6 | Ct value | 27.1 | — | 27.1 | 27.2 | 27.2 | 27.1 | 27.1 | 27.1 | 27.1 | 27.2 | 27.0 |
| | CDK10 | | 31.2 | — | 31.0 | 31.3 | 31.2 | 31.1 | 31.2 | 31.1 | 31.0 | 31.1 | 31.3 |
| | RPS19 | | 22.4 | — | 21.8 | 21.4 | 22.3 | 21.7 | 22.1 | 21.7 | 21.5 | 21.8 | 22.4 |

(1) Components of PCR Reaction Liquid
PCR Mix

The same PCR mix 1 as that used in Test Example 6 was used.

Primer/Probe

TaqMan (registered trademark) Gene Expression Assays (Thermo Fisher Scientific) were used as primer/probe mixtures at a 20-fold concentration. The genes amplified/detected by the primers/probes in the mixtures were IL6, CDK10, and RPS19.

Nucleic Acid Template cDNA produced from HeLa cell (derived from human cervical cancer) RNA was used. For RNA extraction and cDNA synthesis, Human HeLa Cell Total RNA (636543; Takara Bio Inc.) and SuperPrep (trademark) II Cell Lysis & RT Kit for qPCR (SCQ-401; Toyobo Co., Ltd.) were used. The procedure was performed according to the instruction manual.

(2) Reaction
Reaction Liquid

Each primer/probe set and the nucleic acid template were each mixed with PCR mix 1 in an amount that is 1/20th of the total liquid volume to prepare mixtures (each 19 µL). As controls, 1 µL of 20 mM Tris-HCl (pH 7.5) was added to each mixture, followed by exposure at −20° C. or 25° C. for 24 hours. For each anti-domain E antibody, 1 µL of a 0.1 mg/mL solution thereof (amount brought in: 0.1 µg) was added to each mixture, followed by exposure at 25° C. for 24 hours. Thereafter, reactions were performed in the following temperature cycles with a real-time PCR device (Applied Biosystems 7500 Fast Real-Time PCR System). Fluorescence readings were performed in the extension step at 60° C. for 60 seconds.

Temperature Cycle
  Step 1: 95° C. 1 min
  Step 2: 95° C. 15 sec-60° C. 60 sec, 50 cycles (PCR)

(3) Results

Table 14 shows the Ct values in detecting the genes (IL6, CDK10, and RPS19). When the reaction liquids containing Tris-HCl were exposed at 25° C. for 24 hours, the three genes were undetectable. In contrast, when the reaction liquids to which 0.1 µg of each anti-domain E antibody was individually added were used, no delay in the Ct values was observed, and all of the genes were detectable. Moreover, no Test Example 9: Suppression of Probe Degradation by Small Amount of Anti-Domain E Antibody It was confirmed whether probe degradation is suppressed when a PCR reaction liquid containing 0.1 µg of an anti-domain E antibody is exposed at 25° C. for 24 hours.

(1) Components of Reaction Liquid
PCR Mix

The same PCR mix 2 as that used in Test Example 7 was used.

Primer/Probe

TaqMan (registered trademark) Gene Expression Assays (Thermo Fisher Scientific) were used as primer/probe mixtures at a 20-fold concentration. The genes amplified/detected by the primers/probes in the mixtures were IL6, CDK10, SIVA1, and RPS19.

Nucleic Acid Template cDNA produced from HeLa cell (derived from human cervical cancer) RNA was used. For RNA extraction and cDNA synthesis, Human HeLa Cell Total RNA (636543; Takara Bio Inc.) and SuperPrep (trademark) II Cell Lysis & RT Kit for qPCR (SCQ-401; Toyobo Co., Ltd.) were used. The procedure was performed according to the instruction manual.

(2) Reaction

Each primer/probe set and the nucleic acid template were each mixed with PCR mix 2 in an amount that is 1/20th of the total liquid volume to prepare mixtures (each 15 µL). As controls, 5 µL of 20 mM Tris-HCl (pH 7.5) was added to each mixture, followed by exposure at −20° C. or 25° C. for 24 hours. For the anti-domain E antibody, 1 µL of a 0.1 mg/mL solution thereof (amount brought in: 0.1 µg) was added to each mixture, followed by exposure at 25° C. for 24 hours.

Reactions were performed using the reaction liquids in the following temperature cycles with a real-time PCR device (Applied Biosystems 7500 Fast Real-Time PCR System). Fluorescence readings were performed in the extension step at 60° C. for 60 seconds.

Temperature Cycle
  Step 1: 95° C. 1 min
  Step 2: 95° C. 15 sec-60° C. 60 sec, 50 cycles (PCR)

(3) Results

Table 15 shows the Ct values in detecting the genes (IL6, CDK10, SIVA1, and RPS19).

When reaction liquids 4 containing Tris-HCl were exposed at 25° C. for 24 hours, a delay in the Ct value was observed for each gene. In contrast, when the reaction liquids 4 to which 0.1 μg of the anti-domain E antibody was added were exposed at 25° C. for 24 hours, no delay in the Ct values was observed.

When the control reaction liquids containing Tris-HCl were exposed at 25° C. for 24 hours, a delay in the Ct value was observed for each gene. In contrast, when the reaction liquids 5 to which 0.1 μg of the anti-domain E antibody was added were exposed at 25° C. for 24 hours, no delay in the Ct values was observed.

TABLE 15

| Storage conditions | Clone No. | Amount added (μg) | IL6 | CDK10 | SIVA1 | RPS19 |
|---|---|---|---|---|---|---|
| −20° C./24 h | — | 0 | 30.0 | 32.4 | 25.6 | 22.5 |
| 25° C./24 h | — | 0 | — | — | 26.3 | 29.9 |
| | Anti-TTH4 | 0.1 | 29.8 | 32.6 | 25.7 | 22.3 |

Test Example 10. Expression of Chimeric Anti-Domain E Antibody (1) Production of Antibody Expression Plasmid An antibody sequence containing the CDRs of Anti-TTH4 was designed, and oligo DNA was obtained by artificial synthesis. An antibody expression plasmid having mouse-derived heavy and light chain constant regions set forth in SEQ ID NOs: 53 and 54 was produced using Mammalian PowerExpress System (trademark) (MPH-102 and MPL-202; Toyobo Co., Ltd.) according to the instruction manual provided.

(2) Expression of Antibody by ExpiCHO-S(trademark) Cell

ExpiCHO (trademark) Expression System (Thermo Fisher Scientific) was used to express an antibody. The culture conditions were culture with shaking at 37° C., 5% (v/v) $CO_2$, and 80 rpm. ExpiCHO-S(trademark) cells were resuscitated and cultured with shaking at a viable cell count of $2.0×10^5$ cells/mL according to the instruction manual provided. Passaging continued until the viability reached 95% to prepare a culture liquid at a viable cell count of $6.0×10^6$ cells/mL. 1.0 μg of the antibody expression plasmid and 80 μL of ExpiFectamine (trademark) CHO Reagent were diluted with 2 mL of OptiPRO SFM (trademark) and added to 25 mL of the culture liquid, followed by culture with shaking at 37° C., 5% (v/v) $CO_2$, and 80 rpm. After 24 hours, 150 μL of ExpiCHO (trademark) Enhancer and 6 mL of ExpiCHO (trademark) Feed were added, and the culture with shaking was continued at 37° C., 5% (v/v) $CO_2$, and 80 rpm until the viability became 50%.

(3) Purification of Antibody with Protein A Column

A culture supernatant of the ExpiCHO-S(trademark) cells was collected by centrifugation. The culture supernatant was passed through a HiTrap Protein A HP column (Cytiva) to adsorb the antibody using AKTA pure 25 (Cytiva). The column was washed with wash buffer (20 mM phosphate buffer; pH: 7.4), followed by elution with elution buffer (0.1 M citric acid-NaOH; pH: 3.5). The antibody was concentrated with Amicon Ultra-15 (Merck) and quantified with NanoDrop One (Thermo Fisher Scientific).

In the Test Examples below, chimeric anti-domain E antibodies having mouse-derived constant regions obtained by the above method were used.

Test Example 11: Suppression of Probe Degradation by Chimeric Anti-Domain E Antibody It was confirmed whether a chimeric anti-domain E antibody suppresses probe degradation when a PCR reaction liquid containing the chimeric anti-domain E antibody is exposed at 25° C. for 24 hours.

(1) Components of Reaction Liquid

PCR Mix

The same PCR mix 1 as that used in Test Example 6 and the same PCR mix 2 as that used in Test Example 7 were used.

Primer/Probe

TaqMan (registered trademark) Gene Expression Assays (Thermo Fisher Scientific) were used as a primer/probe mixture at a 20-fold concentration. The gene amplified/detected by the primers/probe in the mixture was RPS19.

Nucleic Acid Template cDNA produced from HeLa cell (derived from human cervical cancer) RNA was used. For RNA extraction and cDNA synthesis, Human HeLa Cell Total RNA (636543, Takara Bio Inc.) and SuperPrep (trademark) II Cell Lysis & RT Kit for qPCR (SCQ-401; Toyobo Co., Ltd.) were used. The procedure was performed according to the instruction manual.

(2) Reaction

Reaction Liquids 4 and 5

The primer/probe set was mixed with each of PCR mixes 1 and 2 in an amount that is 1/20th of the total liquid volume to prepare mixtures (each 18 μL) (corresponding to reaction liquids 4 and 5, respectively). The nucleic acid template quantified with NanoDrop™ One (Thermo Fisher Scientific) was diluted to 100, 10, 1, or 0.1 ng/μL, and 1 μL thereof (amount brought in: 100, 10, 1, or 0.1 ng) was added to each mixture. As controls, 1 μL of 20 mM Tris-HCl (pH 7.5) was added to each mixture, followed by exposure at −20° C. or 25° C. for 24 hours. For each chimeric anti-domain E antibody, 1 μL of a 0.1 mg/mL solution thereof (amount brought in: 0.1 μg) was added to the mixtures, followed by exposure at 25° C. for 24 hours. Thereafter, reactions were performed in the following temperature cycles with a real-time PCR device (Applied Biosystems 7500 Fast Real-Time PCR System). Fluorescence readings were performed in the extension step at 60° C. for 60 seconds.

Temperature Cycle

Step 1: 95° C. 1 min

Step 2: 95° C. 15 sec-60° C. 60 sec, 50 cycles (PCR)

(3) Results

Tables 16 and 17 show the results of reaction liquids 4 and 5, respectively. These tables show the Ct values in detecting the RPS19 gene and the fluorescence values at the 10th cycle in multicomponent data.

When reaction liquids 4 and 5 containing Tris-HCl were exposed at 25° C. for 24 hours, the RPS19 gene could not be detected. In contrast, when reaction liquids 4 and 5 to which the chimeric anti-domain E antibodies were added were exposed at 25° C. for 24 hours, the RPS19 gene in 100, 10, 1, and 0.1 ng of HeLa cDNA was detectable with Ct values equivalent to those when exposure was performed at −20° C. for 24 hours. The probe degradation rate estimated by the same method as in (c) of Test Example 7 was 4.4% for Anti-TAQ2 and 3.3% for Anti-TTH4.

TABLE 16

| | Clone No. Storage temperature (° C.) Storage time (h) | Ct value −20 | — | Anti-TAQ2 25 |
|---|---|---|---|---|
| | | | 24 | |
| Hela cDNA amount (ng) | 100 | 27.0 | — | 27.5 |
| | 10 | 30.4 | — | 30.7 |
| | 1 | 33.9 | — | 34.2 |
| | 0.1 | 37.0 | — | 38.2 |
| | 0 | — | — | — |
| | Slope | −3.33 | — | −3.57 |
| | Intercept | 33.7 | — | 34.4 |
| | Coefficient of determination R2 | 1.00 | — | 1.00 |
| | PCR efficiency | 1.00 | — | 0.91 |

| Storage temperature (° C.) | Storage time (h) | Clone No. | Fluorescence value average of N = 5 | (c) Probe degradation rate (%) |
|---|---|---|---|---|
| −20 | 24 | — | 310056 | 0 |
| 25 | | | 1256755 | 100 |
| | | Anti-TAQ2 | 351392 | 4.4 |

TABLE 17

| | Clone No. Storage temperature (° C.) Storage time (h) | Ct value −20 | — | Anti-TTH4 25 |
|---|---|---|---|---|
| | | | 24 | |
| Hela cDNA amount (ng) | 100 | 27.5 | — | 27.5 |
| | 10 | 30.9 | — | 30.9 |
| | 1 | 34.5 | — | 34.4 |
| | 0.1 | 38.3 | — | 38.4 |
| | 0 | — | — | — |
| | Slope | −3.62 | — | −3.61 |
| | Intercept | 34.6 | — | 34.6 |
| | R2 | 1.00 | — | 1.00 |
| | PCR efficiency | 0.89 | — | 0.89 |

| Storage temperature (° C.) | Storage time (h) | Clone No. | Fluorescence value average of N = 5 | (c) Probe degradation rate % |
|---|---|---|---|---|
| −20 | 24 | — | 218112 | 0 |
| 25 | | | 1159119 | 100 |
| | | Anti-TTH4 | 243930 | 33 |

Test Example 12: Suppression of Probe Degradation when Taq Polymerase (Mutant) or Z05 Polymerase is Present with Anti-Domain E Antibody It was confirmed whether an anti-domain E antibody suppresses probe degradation when a PCR reaction liquid containing the anti-domain E antibody and Taq polymerase (mutant) or Z05 polymerase is exposed at 25° C. for 24 hours.
(1) Components of Reaction Liquid
PCR Mix
The following three PCR mixes 4 to 6 were prepared and used.
PCR Mix 4:
  QuantiNova Probe RT-PCR Kit (QIAGEN; 208352) containing Taq polymerase (mutant)
PCR Mix 5:
  TaqMan Fast Advanced Master Mix (Thermo Fisher Scientific; 4444556) containing Taq polymerase (mutant)
PCR Mix 6:
  Z05 polymerase (0.05 U/μL; Roche Diagnostics; HawkZ05; SEQ ID NO: 55);
  anti-polymerase antibody for hot-start PCR (0.01 μg/μl; TCP-101; Toyobo Co., Ltd.);
  10 mM Tris-HCl (pH 8.3);
  80 mM KCl;
  1.5 mM MgCl$_2$;
  0.5 mg/mL BSA;
  0.1% (v/v) Triton X-100;
  0.1% (w/v) sodium cholate; and
  0.3 mM dNTPs
Primer/Probe
  TaqMan (registered trademark) Gene Expression Assays (Thermo Fisher Scientific) were used as a primer/probe mixture at a 20-fold concentration. The gene amplified/detected by the primers/probe in the mixture was RPS19.
Nucleic Acid Template
  cDNA produced from HeLa cell (derived from human cervical cancer) RNA was used. For RNA extraction and cDNA synthesis, Human HeLa Cell Total RNA (636543; Takara Bio Inc.) and SuperPrep (trademark) II Cell Lysis & RT Kit for qPCR (SCQ-401; Toyobo Co., Ltd.) were used. The procedure was performed according to the instruction manual.
(2) Reaction
Reaction Liquids 6 to 8
  The primer/probe set and the nucleic acid template were each mixed with each of PCR mixes 4 to 6 in an amount that is 1/20th of the total liquid volume to prepare mixtures (each 19 μL) (corresponding to reaction liquids 6 to 8, respectively). As controls, 1 μL of 20 mM Tris-HCl (pH 7.5) was added to each mixture, followed by exposure at −20° C. or 25° C. for 24 hours. For each anti-domain E antibody, 1 μL of a 0.1 mg/mL solution thereof (amount brought in: 0.1 μg) was added to the mixtures, followed by exposure at 25° C. for 24 hours. Thereafter, reactions were performed in the following temperature cycles with a real-time PCR device (Applied Biosystems 7500 Fast Real-Time PCR System). Fluorescence readings were performed in the extension step at 60° C.

Temperature Cycle for Reaction Liquid 6 Containing PCR Mix 4
step 1: 95° C. 2 min
step 2: 95° C. 5 sec-60° C. 24 sec, 50 cycles (PCR)
Temperature Cycle for Reaction Liquid 7 Containing PCR Mix 5
step 1: 95° C. 20 sec
step 2: 95° C. 3 sec-60° C. 30 sec, 50 cycles (PCR)
Temperature Cycle for Reaction Liquid 8 Containing PCR Mix 6
step 1: 95° C. 60 sec
step 2: 95° C. 15 sec-60° C. 45 sec, 50 cycles (PCR)
(3) Results Tables 18 and 19 show the Ct values in detecting the RPS19 gene and the fluorescence values at the 10th cycle in multicomponent data.

When reaction liquids 8 to 10 containing Tris-HCl were exposed at 25° C. for 24 hours, there was a delay in the Ct value at which the RPS19 gene could be detected, or the gene was undetectable. In contrast, when reaction liquids 8 to 10 to which the anti-domain E antibodies were added were exposed at 25° C. for 24 hours, the gene was detectable with Ct values equivalent to those when exposure was performed at −20° C. for 24 hours. These results reveal that the anti-domain E antibody significantly improves the stability of PCR reaction liquids containing a Taq mutant. It was also found that the anti-domain E antibody significantly improves the stability of PCR reaction liquids containing Z05 polymerase.

TABLE 18

| Product name | QuantiNova RT-PCR Probe Kit | | TaqMan Fast Advanced Master Mix | |
|---|---|---|---|---|
| Storage temperature (° C.) | −20 | 25 | −20 | 25 |
| Storage time (h) | | 24 | | |
| Clone No. | — | Anti-TAQ2 | — | Anti-TAQ2 |
| Ct value | 25.0 | 25.0 | 25.1 | 28.9 | 24.8 |

TABLE 19

| Product name | Hawk Z05 DNA Polymerase | |
|---|---|---|
| Storage temperature (° C.) | −20 | 25 |
| Storage time (h) | | 24 |
| Clone No. | — | Anti-TTH4 |
| Ct value | 26.9 | — | 27.0 |

Test Example 13: Inhibition Ability of Anti-Domain E Antibody for 5' to 3' Exonuclease Activity The inhibition ability of obtained anti-domain E antibodies for 5' to 3' exonuclease activity of Taq polymerase or Tth polymerase was confirmed.
(1) Reaction
Reaction Liquid 9

A Taq enzyme liquid containing 1 unit of Taq polymerase (TAP-201; Toyobo Co., Ltd.) and 0.2 µg of commercially available hot-start antibody Anti-Taq high (TCP-101; Toyobo Co., Ltd.) was prepared. A mixture of the Taq polymerase enzyme liquid and 0.1 µg of Anti-TAQ2 was added to a reaction liquid (final concentration: 10 mM Tris-HCl (pH 8.6), 50 mM KCl, 1.5 mM $MgCl_2$) containing substrate DNA radiolabeled with $^{32}P$ at the 5' end (9000 cpm; counting rate: 80%) to give a liquid volume of 20 µL (sample 3). As controls, sample 1 containing neither the Taq polymerase enzyme liquid nor Anti-TAQ2 and sample 2 containing only the Taq polymerase enzyme liquid were prepared, and each sample was incubated at 37° C. for 24 hours. Thereafter, 100 µL of 10% (w/v) TCA was added to each sample to precipitate the substrate DNA, and the radioactivity of free $^{32}P$-labeled bases remaining in the supernatants was measured.
Reaction Liquid 10

A Tth enzyme liquid containing 1 unit of Tth polymerase (TTH-301; Toyobo Co., Ltd.) and 0.6 µg of commercially available hot-start antibody Anti-Taq high (TCP-101; Toyobo Co., Ltd.) was prepared. A mixture of the Tth polymerase enzyme liquid and 0.1 µg of Anti-TTH4 was added to a reaction liquid (final concentration: 10 mM Tris-HCl (pH 8.6), 50 mM KCl, 1.5 mM $MgCl_2$) containing substrate DNA radiolabeled with $^{32}P$ at the 5' end (9000 cpm; counting rate: 80%) to give a liquid volume of 20 µL (sample 3). As controls, sample 1 containing neither the Tth polymerase enzyme liquid nor Anti-TTH4 and sample 2 containing only the Tth polymerase enzyme liquid were prepared, and each sample was incubated at 37° C. for 24 hours. Thereafter, 100 µL of 10% (w/v) TCA was added to each sample to precipitate the substrate DNA, and the radioactivity of free $^{32}P$-labeled bases remaining in the supernatants was measured.
Substrate DNA A reaction liquid was prepared by mixing 10 µg of ΛDNA and 30 units of Sca I (Toyobo Co., Ltd.) according to the instruction manual and incubated at 37° C. for 24 hours. Pellets produced by phenol/chloroform/isoamyl alcohol (liquid volume ratio 25:24:1) treatment and ethanol precipitation were dissolved in 100 µL of TE buffer. To 80 µL of the solution, 5 µL of P-32 Adenosine 5'-triphosphate, [γ-32P]- (produced by PerkinElmer; NEG002), 5 µL of T4 Polynucleotide Kinase (produced by Toyobo Co., Ltd.; PNK-111), and 10 µL of 10× Blunt End Kinase Buffer (produced by Toyobo Co., Ltd.; included in PNK-111) were added, followed by incubation at 37° C. for 1 hour. Pellets produced by phenol/chloroform/isoamyl alcohol (liquid volume ratio 25:24:1) treatment and ethanol precipitation were dissolved in 100 µL of TE buffer.
(2) Results Table 20 shows the results of reaction liquid 9. The percentage of the remaining substrate DNA in sample 3 was calculated as the ability to inhibit 5' to 3' exonuclease activity, based on the percentage of the remaining substrate DNA in sample 1 containing neither the Taq polymerase enzyme liquid nor Anti-TAQ2, in which the substrate DNA is not degraded, taken as 100%, and the percentage of the remaining substrate DNA in sample 2 containing only the Taq polymerase enzyme liquid, in which the substrate DNA is the most degraded, taken 0%. The ability of Anti-TAQ2 to inhibit the activity was calculated to be 91%.

Table 21 shows the results of reaction liquid 10. The percentage of the remaining substrate DNA in sample 3 was calculated as the ability to inhibit 5' to 3' exonuclease activity, based on the percentage of the remaining substrate DNA in sample 1 containing neither the Tth polymerase enzyme liquid nor Anti-TTH4, in which the substrate DNA is not degraded, taken as 100%, and the percentage of the remaining substrate DNA in sample 2 containing only the Tth polymerase enzyme liquid, in which the substrate DNA is the most degraded, taken as 0%. The ability of Anti-TTH4 to inhibit the activity was calculated to be 98%.

TABLE 20

|  | Taq polymerase | Clone No. Anti-TAQ2 | Average of N = 2 (cpm) | Activity (%) |
|---|---|---|---|---|
| Sample 1 | − | − | 1888 | 100 |
| Sample 2 | + | − | 2841 | 0 |
| Sample 3 | + | + | 1973 | 91 |

TABLE 21

|  | Tth polymerase | Clone No. Anti-TTH4 | Average of N = 2 (cpm) | Activity (%) |
|---|---|---|---|---|
| Sample 1 | − | − | 2014 | 100 |
| Sample 2 | + | − | 2916 | 0 |
| Sample 3 | + | + | 2029 | 98 |

Test Example 14: Inhibition Ability of Varying Amounts of Anti-Domain E Antibody for 5' to 3' Exonuclease Activity The inhibition ability for 5' to 3' exonuclease activity of Taq polymerase was confirmed by varying the amount of anti-domain E antibody obtained.
(1) Reaction
Reaction Liquid
A Taq polymerase enzyme liquid containing 1 unit of Taq polymerase (TAP-201; Toyobo Co., Ltd.) and 0.2 μg of commercially available hot-start antibody Anti-Taq high (TCP-101; Toyobo Co., Ltd.) was prepared. A mixture of the Taq polymerase enzyme liquid and 0.05, 0.1, 0.2, or 0.4 μg of Anti-TAN was added to a reaction liquid (final concentration: 10 mM Tris-HCl (pH 8.6), 50 mM KCl, 1.5 mM MgCl$_2$) containing substrate DNA radiolabeled with $^{32}$P at the 5' end (9000 cpm; counting rate: 80%) to give a liquid volume of 20 μL (samples 3 to 6). As controls, sample 1 containing neither the Taq polymerase enzyme liquid nor Anti-TAQ2 and sample 2 containing only the Taq polymerase enzyme liquid were prepared, and each sample was incubated at 37° C. for 24 hours. Thereafter, 100 μL of 10% (w/v) TCA was added to each sample to precipitate the substrate DNA, and the radioactivity of free $^{32}$P-labeled bases remaining in the supernatants was measured.
Substrate DNA
The same substrate DNA as that used in Test Example 13 was used.
(2) Result
Table 22 shows the results. The percentage of the remaining substrate DNA in each of samples 3 to 6 was calculated as the ability to inhibit 5' to 3' exonuclease activity, based on the percentage of the remaining substrate DNA in sample 1 containing neither the Taq polymerase enzyme liquid nor Anti-TAQ2, in which the substrate DNA is not degraded, taken as 100%, and the percentage of the remaining substrate DNA in sample 2 containing only the Taq polymerase enzyme liquid, in which the substrate DNA is the most degraded, taken as 0%.

TABLE 22

|  | Taq polymerase | Amount of Anti-TAQ2 added (μg) | Counts per minute (cpm) | Activity (%) |
|---|---|---|---|---|
| Sample 1 | − | 0 | 755 | 100 |
| Sample 2 | + | 0 | 1924 | 0 |
| Sample 3 | + | 0.05 | 762 | 99 |
| Sample 4 | + | 0.1 | 731 | 102 |
| Sample 5 | + | 0.2 | 742 | 101 |
| Sample 6 | + | 0.4 | 717 | 103 |

Test Example 15: Suppression of Probe Degradation Due to Tth Polymerase by Antibody that Specifically Binds to Domain E of Taq Polymerase It was confirmed whether an antibody that specifically binds to domain E of Taq polymerase suppresses probe degradation due to Tth polymerase when a PCR reaction liquid containing the antibody and Tth polymerase is exposed at 25° C. for 24 hours.
(1) Components of PCR Reaction Liquid
PCR Mix
The same PCR mix 1 as that used in Test Example 6 and the same PCR mix 2 as that used in Test Example 7 were used.
Primer/Probe
TaqMan (registered trademark) Gene Expression Assays (Thermo Fisher Scientific) were used as primer/probe mixtures at a 20-fold concentration. The genes amplified/detected by the primers/probes in the mixtures were IL6, CDK10, SIVA1, RPS19, and SERPINB5.
Nucleic Acid Template
cDNA produced from HeLa cell (derived from human cervical cancer) RNA was used. For RNA extraction and cDNA synthesis, Human HeLa Cell Total RNA (product code: 636543; Takara Bio Inc.) and SuperPrep (trademark) II Cell Lysis & RT Kit for qPCR (SCQ-401; Toyobo Co., Ltd.) were used. The procedure was performed according to the instruction manual.
(2) Reaction
Each primer/probe set was mixed with PCR Mix 1 or 2 in an amount that is 1/20th of the total liquid volume to prepare mixtures (each 18 μL). The nucleic acid template quantified with NanoDrop™ One (Thermo Fisher Scientific) was diluted to 100 ng/μL, and 1 μL thereof (amount brought in: 100 ng) was added. As controls, 1 μL of 20 mM Tris-HCl (pH 7.5) was added, followed by exposure at −20° C. or 25° C. for 24 hours. For Anti-TAQ2, 4 μL of a 0.1 mg/mL solution thereof (amount brought in: 0.4 μg) was added, followed by exposure at 25° C. for 24 hours. Thereafter, reactions were performed in the following temperature cycles with a real-time PCR device (Applied Biosystems 7500 Fast Real-Time PCR System). Fluorescence readings were performed in the extension step at 60° C. for 45 seconds.
Temperature Cycle
 Step 1: 95° C. 1 min
 Step 2: 95° C. 15 sec-60° C. 45 sec, 50 cycles (PCR)
(3) Result
Table 23 shows the Ct values in detecting the genes and the fluorescence values at the 10th cycle in multicomponent data. When the reaction liquids containing Tris-HCl were exposed at 25° C. for 24 hours, genes could not be detected or significant delays in the Ct values were observed, i.e., the detection sensitivity was reduced. In contrast, when the reaction liquids containing Anti-TAQ2 were exposed at 25° C. for 24 hours, the genes in HeLa cDNA were detectable with Ct values equivalent to those when the reaction liquids containing Tris-HCl were exposed at −20° C. for 24 hours. Furthermore, it was confirmed that Anti-TAQ2 has an ability to suppress probe degradation for both Taq polymerase and Tth polymerase. It was thus confirmed that an antibody having neutralizing activity against both Taq and Tth can be obtained by method 3, in which Tth exo is used as an immunogen and antibodies against whole Taq are screened.

TABLE 23

| Enzyme | Storage conditions | Antibody No. | Gene name | | | | |
|---|---|---|---|---|---|---|---|
| | | | IL6 | CDK10 | SIVA1 | RPS19 | SERPINB5 |
| Taq polymerase | −20° C./24 h | — | 32.7 | 37.0 | 31.3 | 26.7 | 35.9 |
| | 25° C./24 h | — | — | — | 42.7 | — | 38.8 |
| | | Anti-TAQ2 | 32.9 | 37.3 | 31.8 | 26.6 | 35.7 |
| Tth polymerase | −20° C./24 h | — | 35.3 | 37.8 | 30.8 | 27.3 | 35.9 |
| | 25° C./24 h | — | — | — | 32.4 | — | — |
| | | Anti-TAQ2 | 34.9 | 38.4 | 31.2 | 27.5 | 36.3 |

Test Example 16: Inhibition Ability of Anti-Domain E Antibody for 5' to 3' Exonuclease Activity When Substrate DNA Is Changed Double-stranded substrate DNA derived from ADNA set forth in SEQ ID NOs: 56 and 57 was designed, and the inhibition ability of an anti-domain E antibody for 5' to 3' exonuclease activity of Taq polymerase or Tth polymerase was confirmed.

(1) Sample Preparation

The following two activity measurement mixes 1 and 2 were prepared and used.

Activity Measurement Mix 1:
Taq polymerase (0.05 U/µL; TAP-201; produced by Toyobo Co., Ltd.);
anti-polymerase antibody for hot-start PCR (0.01 µg/µl; TCP-101; produced by Toyobo Co., Ltd.);
10 mM Tris-HCl (pH 8.6);
50 mM KCl;
1.5 mM MgCl$_2$; and
0.3 µM double-stranded substrate DNA Activity Measurement Mix 2:
Tth polymerase (0.05 U/µL; TTH-301; produced by Toyobo Co., Ltd.);
anti-polymerase antibody for hot-start PCR (0.01 µg/µl; TCP-101; produced by Toyobo Co., Ltd.);
10 mM Tris-HCl (pH 8.6);
50 mM KCl;
1.5 mM MgCl$_2$; and
0.3 µM double-stranded substrate DNA Double-Stranded Substrate DNA Double-stranded substrate DNA derived from ADNA containing the oligonucleotides set forth in SEQ ID NOs: 56 and 57 was designed. The oligonucleotides set forth in SEQ ID NOs: 56 and 57 were separately synthesized, mixed in equal amounts, and used.

As controls, 1 µL of 20 mM Tris-HCl (pH 7.5) was added to 19 µL of each activity measurement mix, followed by exposure at −20° C. or 25° C. for 24 hours. Regarding the anti-domain E antibody, 1 µL of a 0.1 mg/mL solution thereof (amount brought in: 0.1 µg) was added to 19 µL of activity measurement mix 1, and 1 µL of a 0.4 mg/mL solution thereof (amount brought in: 0.4 µg) was added to 19 µL of activity measurement mix 2, followed by exposure at 25° C. for 24 hours. Thereafter, each sample was analyzed with a microchip electrophoresis system for DNA/RNA analysis (MultiNA; Shimadzu Corporation) and a DNA-500 kit (S292-27910-91; Shimadzu Corporation).

(2) Result

Table 24 shows the quantitative values of the bands when each sample was analyzed. When Tris-HCl was added to activity measurement mixes 1 and 2, and the resulting mixtures were exposed at 25° C. for 24 hours, the quantitative values of the bands were significantly lower than those when they were exposed at −20° C. for 24 hours, confirming the degradation of the double-stranded substrate DNA. In contrast, when Anti-TAQ2 was added to activity measurement mixes 1 and 2, and the resulting mixtures were exposed at 25° C. for 24 hours, the quantitative values of the bands were equivalent to those when Tris-HCl was added, and the resulting mixtures were exposed at −20° C. for 24 hours, and no degradation of the double-stranded substrate DNA was observed.

The ability to inhibit 5' to 3' exonuclease activity was determined by calculating (d) the double-stranded substrate DNA degradation rate below.

(d)Double-stranded substrate DNA degradation rate (%)[$(S_{21}-S_{23})/(S_{21}-S_{22})\times 100$]

$S_{21}$: band intensity after exposure at −20° C. for 24 hours (corresponding to before exposure at 25° C. for 24 hours) without the anti-domain E antibody $S_{22}$: band intensity after exposure at 25° C. for 24 hours without the anti-domain E antibody.

$S_{23}$: band intensity after exposure at 25° C. for 24 hours with the anti-domain E antibody In the samples containing Anti-TAN and exposed at 25° C. for 24 hours, (d) the double-stranded substrate DNA degradation rates (%) due to Taq polymerase and Tth polymerase were calculated to be 10%. Thus, Anti-TAQ2 was found to exhibit sufficient ability to suppress double-stranded substrate DNA degradation for both Taq polymerase and Tth polymerase.

TABLE 24

| Enzyme | Double-stranded substrate DNA | Storage conditions | Antibody No. | Average of area values (N = 3) (mV · μm) | (d) Double-stranded substrate DNA degradation rate (%) |
|---|---|---|---|---|---|
| Taq pofymerase | SEQ ID No: 56 and SEQ ID No: 57 | −20° C./24 h | — | 401 | 0 |
| | | 25° C./24 h | — | 170 | 100 |
| | | | Anti-TAQ2 | 381 | 9 |
| Tth polymerase | | −20° C./24 h | — | 536 | 0 |
| | | 25° C./24 h | — | 14 | 100 |
| | | | Anti-TAQ2 | 568 | −6 |

Test Example 17: Suppression of Fluorescent-Labeled Double-Stranded Substrate DNA (Probe) Degradation Due to DNA Polymerase by Antibody that Specifically Binds to Domain E of Taq Polymerase It was confirmed whether an antibody that specifically binds to domain E of Taq polymerase suppresses degradation of fluorescent-labeled double-stranded substrate DNA due to a polymerase when a PCR reaction liquid containing the antibody and a DNA polymerase (Taq polymerase or Tth polymerase) is exposed at 37° C. for 24 hours.

(1) Components of Reaction Liquid
PCR Mix
The following two PCR Mixes 7 and 8 were prepared and used.
PCR Mix 7:
  Taq polymerase (0.05 U/μL; TAP-201; produced by Toyobo Co., Ltd.);
  anti-polymerase antibody for hot-start PCR (0.01 μg/μl; TCP-101; produced by Toyobo Co., Ltd.);
  10 mM Tris-HCl (pH 8.6);
  50 mM KCl;
  1.5 mM MgCl$_2$; and
  0.3 μM fluorescent-labeled double-stranded substrate DNA
PCR Mix 8:
  Tth polymerase (0.05 U/μL; TTH-301; produced by Toyobo Co., Ltd.);
  anti-polymerase antibody for hot-start PCR (0.01 μg/μl; TCP-101; produced by Toyobo Co., Ltd.);
  10 mM Tris-HCl (pH 8.6);
  50 mM KCl;
  1.5 mM MgCl$_2$; and
  0.3 μM fluorescent-labeled double-stranded substrate DNA Fluorescent-labeled Double-Stranded Substrate DNA
Fluorescent-labeled double-stranded substrate DNA derived from λDNA containing the oligonucleotides set forth in SEQ ID NOs: 58 and 59 was designed (here, the 5' end of SEQ ID NO: 58 was labeled with FAM and the 5' end was labeled with BHQ1). The oligonucleotides set forth in SEQ ID NOs: 58 and 59 were separately synthesized, mixed in equal amounts, and used.

(2) Reaction
As controls, reaction liquids obtained by adding 1 μL of 20 mM Tris-HCl (pH 7.5) to 19 μL of each PCR mix were exposed at −20° C. or 37° C. for 24 hours. Reaction liquids obtained by adding 1 μL of a 0.4 mg/mL anti-domain E antibody solution (amount brought in: 0.4 μg) to 19 μL of each PCR mix were exposed at 37° C. for 24 hours.

Thereafter, reactions were performed in the following temperature cycles with a real-time PCR device (Applied Biosystems 7500 Fast Real-Time PCR System). Fluorescence readings were performed in the extension step at 60° C. for 45 seconds.

Temperature Cycle
  Step 1: 95° C. 1 min
  Step 2: 95° C. 15 sec-60° C. 45 sec, 50 cycles (PCR)

(3) Results
Table 25 shows the fluorescence values at the 10th cycle in multicomponent data. When the reaction liquids containing Tris-HCl were exposed at 37° C. for 24 hours, increases in the fluorescence values were observed compared with when they were exposed at −20° C. for 24 hours. In contrast, when the reaction liquids to which Anti-TAQ2 was added were exposed at 37° C. for 24 hours, the fluorescence values were equivalent to those when the reaction liquids containing Tris-HCl were exposed at −20° C. for 24 hours, and no increase in the fluorescence values was observed in both cases of Taq polymerase and Tth polymerase.

Specifically, (e) the fluorescent-labeled double-stranded substrate DNA degradation rate can be calculated using the following formula.

$$\text{fluorescent-labeled double-stranded substrate DNA degradation rate}[(F_{43}-F_{41})/(F_{42}-F_{41})\times 100)] \quad (e)$$

$F_{41}$: fluorescence intensity at the 10th cycle after exposure at −20° C. for 24 hours (corresponding to before exposure at 37° C. for 24 hours) without the anti-domain E antibody $F_{42}$: fluorescence intensity at the 10th cycle after exposure at 37° C. for 24 hours without the anti-domain E antibody $F_{43}$: fluorescence intensity at the 10th cycle after exposure at 37° C. for 24 hours with the anti-domain E antibody In the samples containing Anti-TAN and exposed at 37° C. for 24 hours, (e) the fluorescent-labeled double-stranded substrate DNA degradation rates (%) due to Taq polymerase and Tth polymerase were calculated to both be ≤10%. Thus, Anti-TAQ2 was found to exhibit a sufficient ability to suppress fluorescent-labeled double-stranded substrate DNA degradation for both Taq polymerase and Tth polymerase.

TABLE 25

| Enzyme | Double-stranded substrate DNA | Storage conditions | Antibody No. | Fluorescence value | (e) Fluorescent-labeled double-stranded substrate DNA degradation rate (%) |
|---|---|---|---|---|---|
| Taq polymerase | SEQ ID No: 58 and SEQ ID No: 59 | −20° C./24 h | — | 856281 | 0 |
|  |  | 37° C./24 h | — | 1027883 | 100 |
|  |  |  | Anti-TAQ2 | 847805 | −5 |
| Tth polymerase |  | −20° C./24 h | — | 861605 | 0 |
|  |  | 37° C./24 h | — | 1204385 | 100 |
|  |  |  | Anti-TAQ2 | 854871 | −2 |

Test Example 18: Measurement of Association Rate Constant (ka Value), Dissociation Rate Constant (kd Value), and Equilibrium Dissociation Constant ($K_D$ Value) of Antibody The affinities of antibodies for Tth polymerase were determined using surface plasmon resonance (SPR). The measuring device used was Biacore X100 (Cytiva). As running buffer, 0.01 M HEPES, 0.15 M NaCl, 3 mM EDTA, and 0.05% (v/v) Surfactant P20 (Cytiva) were used.
(1) Immobilization by Amine Coupling
A ligand (Tth polymerase) was immobilized on a CM5 sensor chip (Cytiva) using EDC and NHS, and blocking was performed with a 1 M ethanolamine hydrochloride solution. As a result, Tth polymerase was immobilized at a density of 200 to 500 RU on flow cells 1 to 4.
(2) Interaction Measurement
The antibodies were serially diluted in the range of 0.222 to 81 nM and added on the flow cells. The resulting sensorgrams were fitted to the bivalent analyte model of Biacore X100 evaluation software to determine the association rate constants (ka), dissociation rate constants (kd), and equilibrium dissociation constants ($K_D$).
(3) Results
Table 24 shows the results of analysis of the interaction of Anti-TTH2, Anti-TTH4, and Anti-TTH5 as anti-domain E antibodies. All of the anti-domain E antibodies showed a $K_D$ of 10 nM or less.

TABLE 26

| Antibody No. | ka1(1/Ms) | kd1(1/s) | ka2(1/RUs) | kd2(1/s) | $k_D$(nM) |
|---|---|---|---|---|---|
| Anti-TTH2 | $4.046 \times 10^5$ | $2.532 \times 10^{-4}$ | 0.003132 | 0.01332 | 0.63 |
| Anti-TTH4 | $1.545 \times 10^6$ | $3.082 \times 10^{-4}$ | $2.452 \times 10^{-4}$ | 0.007099 | 0.20 |
| Anti-TTH5 | $4.546 \times 10^4$ | $3.383 \times 10^{-4}$ | $2.992 \times 10^{-4}$ | 0.001252 | 7.4 |

Test Example 19: Epitope Mapping of Antibody

Epitope mapping was performed using conformational epitope mapping of PEPperPRINT's PEPperMAP (trademark) Peptide Microarray contract analysis service. Of the amino acid sequence of Taq exo set forth in SEQ ID NO: 1 (from the N-terminus to the 290th amino acid of whole Taq) and of the amino acid sequence of Tth exo set forth in SEQ ID NO: 2 (from the N-terminus to the 292nd amino acid of whole Tth), peptides consisting of 7, 10, and 13 amino acids were synthesized on peptide arrays so that they were shifted by 1 amino acid to overlap by 6, 9, and 12 amino acids. Thereafter, detection signals indicating binding of Anti-TAQ2 and Anti-TTH4 were measured for each peptide array to identify the epitopes that interact with the antibodies.
Results
It was confirmed that Anti-TAQ2 binds to at least two regions (amino acid sequences KEDGDAVIVVF (SEQ ID NO: 61) and LERLEFGSLLHEF (SEQ ID NO: 77)) in Taq exo (SEQ ID NO: 1), and binds to at least four regions (amino acid sequences EDGYKAVFVVF (SEQ ID NO: 62), HLITPEWLW (SEQ ID NO: 66), KYGLRPEQWVDF (SEQ ID NO: 67), and LRAFLERLEF (SEQ ID NO: 78)) in Tth exo (SEQ ID NO: 2).

It was also confirmed that Anti-TTH4 binds to at least three regions (amino acid sequences HEAYGGY (SEQ ID NO: 64), EKYGLRPDQWADY (SEQ ID NO: 68), and RAFLERLEFGSLLH (SEQ ID NO: 80)) in Taq exo (SEQ ID NO: 1), and binds to at least five regions (amino acid sequences HEAYEAY (SEQ ID NO: 65), GLRPEQWVDF (SEQ ID NO: 70), ITPEWLW (SEQ ID NO: 71), LRAFLERLEF (SEQ ID NO: 78), and LEFGSLLHEF (SEQ ID NO: 82)) in Tth exo (SEQ ID NO: 2).

Anti-TAQ2 was an antibody that recognizes and binds to an epitope containing a sequence (EDGDAVIVVF (SEQ ID NO: 60) or EDGYKAVFVVF (SEQ ID NO: 62)) in amino acid region A that is common or similar between Taq exo and Tth exo, and an epitope containing a common sequence (LERLEF (SEQ ID NO: 75)) in amino acid region D.

Anti-TTH4 was an antibody that recognizes and binds to an epitope containing a sequence (HEAYGGY (SEQ ID NO: 64) or HEAYEAY (SEQ ID NO: 65)) in amino acid region B that is common or similar between Taq exo and Tth exo, an epitope containing a common sequence (EKYGLRPDQWADY (SEQ ID NO: 68), GLRPEQWVDF (SEQ ID NO: 70), or ITPEWLW (SEQ ID NO: 71)) in amino acid region C, and an epitope containing a common sequence (RAFLERLEF (SEQ ID NO: 79) or LEFGSLLH (SEQ ID NO: 81)) in amino acid region D.

Moreover, it was found that both Anti-TAQ2 and Anti-TTH4 bind to an epitope containing a common sequence (LERLEFGSLLH (SEQ ID NO: 76)) in amino acid region D in the amino acid sequence of Taq exo, and recognize and bind to an epitope containing a common sequence (GLRPEQWVDF (SEQ ID NO: 70) or ITPEWLW (SEQ ID NO: 71)) in amino acid region C and an epitope containing a common sequence (LRAFLERLEF (SEQ ID NO: 78)) in binding region D in the amino acid sequence of Tth exo. It was also confirmed that Anti-TAQ2 and Anti-TTH4 bind to an epitope containing a common sequence (LERLEF (SEQ ID NO: 75)) in amino acid region D in Taq exo and Tth exo.

The invention claimed is:

1. An antibody or a fragment thereof, which binds to a 5' to 3' exonuclease active domain of DNA polymerase, wherein the antibody is any of the following:

(i) an antibody comprising
heavy chain CDR1 comprising the amino acid sequence of SEQ ID NO: 4;
heavy chain CDR2 comprising the amino acid sequence of SEQ ID NO: 12;
heavy chain CDR3 comprising the amino acid sequence of SEQ ID NO: 21;
light chain CDR1 comprising the amino acid sequence of SEQ ID NO: 29;
light chain CDR2 comprising the amino acid sequence of YTN; and
light chain CDR3 comprising the amino acid sequence of SEQ ID NO: 42;

(ii) an antibody comprising
heavy chain CDR1 comprising the amino acid sequence of SEQ ID NO: 5;
heavy chain CDR2 comprising the amino acid sequence of SEQ ID NO: 13;
heavy chain CDR3 comprising an amino acid sequence of any of SEQ ID NO: 22, SEQ ID NO: 23, SEQ ID NO: 96, and SEQ ID NO: 97;
light chain CDR1 comprising the amino acid sequence of SEQ ID NO: 30;
light chain CDR2 comprising the amino acid sequence of YTD; and
light chain CDR3 comprising an amino acid sequence of SEQ ID NO: 43 or 44, (iii) an antibody comprising
heavy chain CDR1 comprising the amino acid sequence of SEQ ID NO: 6;
heavy chain CDR2 comprising the amino acid sequence of SEQ ID NO: 14;
heavy chain CDR3 comprising an amino acid sequence of any of SEQ ID NO: 22, SEQ ID NO: 23, SEQ ID NO: 96, and SEQ ID NO: 97;
light chain CDR1 comprising the amino acid sequence of SEQ ID NO: 31;
light chain CDR2 comprising the amino acid sequence of YAD; and
light chain CDR3 comprising the amino acid sequence of SEQ ID NO: 43 or 44, (iv) an antibody comprising
heavy chain CDR1 comprising the amino acid sequence of SEQ ID NO: 7;
heavy chain CDR2 comprising the amino acid sequence of SEQ ID NO: 15;
heavy chain CDR3 comprising an amino acid sequence of any of SEQ ID NO: 22, SEQ ID NO: 23, SEQ ID NO: 96, and SEQ ID NO: 97;
light chain CDR1 comprising the amino acid sequence of SEQ ID NO: 31;
light chain CDR2 comprising the amino acid sequence of YAN; and
light chain CDR3 comprising an amino acid sequence of SEQ ID NO: 44 or 43, (v) an antibody comprising
heavy chain CDR1 comprising the amino acid sequence of SEQ ID NO: 5;
heavy chain CDR2 comprising the amino acid sequence of SEQ ID NO: 13;
heavy chain CDR3 comprising an amino acid sequence of any of SEQ ID NO: 22, SEQ ID NO: 23, SEQ ID NO: 96, and SEQ ID NO: 97;
light chain CDR1 comprising the amino acid sequence of SEQ ID NO: 31;
light chain CDR2 comprising the amino acid sequence of YAN; and
light chain CDR3 comprising an amino acid sequence of SEQ ID NO: 43 or 44, (vi) an antibody comprising
heavy chain CDR1 comprising the amino acid sequence of SEQ ID NO: 8;
heavy chain CDR2 comprising the amino acid sequence of SEQ ID NO: 16;
heavy chain CDR3 comprising the amino acid sequence of SEQ ID NO: 26;
light chain CDR1 comprising the amino acid sequence of SEQ ID NO: 32;
light chain CDR2 comprising the amino acid sequence of DAS; and
light chain CDR3 comprising the amino acid sequence of SEQ ID NO: 45, (vii) an antibody comprising
heavy chain CDR1 comprising the amino acid sequence of SEQ ID NO: 9;
heavy chain CDR2 comprising the amino acid sequence of SEQ ID NO: 17;
heavy chain CDR3 comprising an amino acid sequence of SEQ ID NO: 24 or 25,
light chain CDR1 comprising the amino acid sequence of SEQ ID NO: 33;
light chain CDR2 comprising the amino acid sequence of GVK; and
light chain CDR3 comprising an amino acid sequence of SEQ ID NO: 46 or 47, (viii) an antibody comprising
heavy chain CDR1 comprising the amino acid sequence of SEQ ID NO: 10;
heavy chain CDR2 comprising the amino acid sequence of SEQ ID NO: 18;
heavy chain CDR3 comprising the amino acid sequence of SEQ ID NO: 27,
light chain CDR1 comprising the amino acid sequence of SEQ ID NO: 33;
light chain CDR2 comprising the amino acid sequence of RAK; and light chain CDR3 comprising the amino acid sequence of SEQ ID NO: 47,
(ix) an antibody comprising
heavy chain CDR1 comprising the amino acid sequence of SEQ ID NO: 5;
heavy chain CDR2 comprising the amino acid sequence of SEQ ID NO: 19;
heavy chain CDR3 comprising an amino acid sequence of SEQ ID NO: 25 or 24,
light chain CDR1 comprising the amino acid sequence of SEQ ID NO: 34;
light chain CDR2 comprising the amino acid sequence of GAK; and
light chain CDR3 comprising an amino acid sequence of SEQ ID NO: 46 or 47, and
(x) an antibody comprising
heavy chain CDR1 comprising the amino acid sequence of SEQ ID NO: 11;
heavy chain CDR2 comprising the amino acid sequence of SEQ ID NO: 20;
heavy chain CDR3 comprising the amino acid sequence of SEQ ID NO: 28,
light chain CDR1 comprising the amino acid sequence of SEQ ID NO: 35;
light chain CDR2 comprising the amino acid sequence of TAS; and
light chain CDR3 comprising the amino acid sequence of SEQ ID NO: 48.

2. The antibody or a fragment thereof according to claim 1, further comprising a sequence region adjacent to the C-terminus of the light chain CDR2, the sequence region comprising an amino acid sequence represented by formula (E-2):

$$X^{E4}X^{E5}X^{E6}X^{E7}, \quad (E\text{-}2)$$

wherein
$X^{E4}$ is G, S, R, H, K, D, N, F, Y, or T,
$X^{E5}$ is L, I, K, H, or R,
$X^{E6}$ is G, A, S, T, P, F, or Y, and
$X^{E7}$ is G, A, D, N, S, or T.

3. The antibody or a fragment thereof according to claim 1, wherein the antibody is any of the following:
(i) an antibody comprising
heavy chain CDR1 comprising the amino acid sequence of SEQ ID NO: 4;
heavy chain CDR2 comprising the amino acid sequence of SEQ ID NO: 12;
heavy chain CDR3 comprising the amino acid sequence of SEQ ID NO: 21;
light chain CDR1 comprising the amino acid sequence of SEQ ID NO: 29;
light chain CDR2 comprising the amino acid sequence of YTN; and
light chain CDR3 comprising the amino acid sequence of SEQ ID NO: 42,
(ii) an antibody comprising
heavy chain CDR1 comprising the amino acid sequence of SEQ ID NO: 5;
heavy chain CDR2 comprising the amino acid sequence of SEQ ID NO: 13;
heavy chain CDR3 comprising an amino acid sequence of any of SEQ ID NO: 22, SEQ ID NO: 23, SEQ ID NO: 96, and SEQ ID NO: 97;
light chain CDR1 comprising the amino acid sequence of SEQ ID NO: 30;
light chain CDR2 comprising the amino acid sequence of YTD; and
light chain CDR3 comprising the amino acid sequence of SEQ ID NO: 43,
(iii) an antibody comprising
heavy chain CDR1 comprising the amino acid sequence of SEQ ID NO: 6;
heavy chain CDR2 comprising the amino acid sequence of SEQ ID NO: 14;
heavy chain CDR3 comprising an amino acid sequence of any of SEQ ID NO: 22, SEQ ID NO: 23, SEQ ID NO: 96, and SEQ ID NO: 97;
light chain CDR1 comprising the amino acid sequence of SEQ ID NO: 31;
light chain CDR2 comprising the amino acid sequence of YAD; and
light chain CDR3 comprising the amino acid sequence of SEQ ID NO: 43,
(iv) an antibody comprising
heavy chain CDR1 comprising the amino acid sequence of SEQ ID NO: 7;
heavy chain CDR2 comprising the amino acid sequence of SEQ ID NO: 15;
heavy chain CDR3 comprising an amino acid sequence of any of SEQ ID NO: 22, SEQ ID NO: 23, SEQ ID NO: 96, and SEQ ID NO: 97;
light chain CDR1 comprising the amino acid sequence of SEQ ID NO: 31;
light chain CDR2 comprising the amino acid sequence of YAN; and
light chain CDR3 comprising the amino acid sequence of SEQ ID NO: 44,
(v) an antibody comprising
heavy chain CDR1 comprising the amino acid sequence of SEQ ID NO: 5;
heavy chain CDR2 comprising the amino acid sequence of SEQ ID NO: 13;
heavy chain CDR3 comprising an amino acid sequence of any of SEQ ID NO: 22, SEQ ID NO: 23, SEQ ID NO: 96, and SEQ ID NO: 97;
light chain CDR1 comprising the amino acid sequence of SEQ ID NO: 31;
light chain CDR2 comprising the amino acid sequence of YAN; and
light chain CDR3 comprising the amino acid sequence of SEQ ID NO: 43,
(vi) an antibody comprising
heavy chain CDR1 comprising the amino acid sequence of SEQ ID NO: 8;
heavy chain CDR2 comprising the amino acid sequence of SEQ ID NO: 16;
heavy chain CDR3 comprising the amino acid sequence of SEQ ID NO: 26;
light chain CDR1 comprising the amino acid sequence of SEQ ID NO: 32;
light chain CDR2 comprising the amino acid sequence of DAS; and
light chain CDR3 comprising the amino acid sequence of SEQ ID NO: 45,
(vii) an antibody comprising
heavy chain CDR1 comprising the amino acid sequence of SEQ ID NO: 9;
heavy chain CDR2 comprising the amino acid sequence of SEQ ID NO: 17;

heavy chain CDR3 comprising an amino acid sequence of SEQ ID NO: 24 or 25,
light chain CDR1 comprising the amino acid sequence of SEQ ID NO: 33;
light chain CDR2 comprising the amino acid sequence of GVK; and
light chain CDR3 comprising the amino acid sequence of SEQ ID NO: 46,
(viii) an antibody comprising
heavy chain CDR1 comprising the amino acid sequence of SEQ ID NO: 10;
heavy chain CDR2 comprising the amino acid sequence of SEQ ID NO: 18;
heavy chain CDR3 comprising the amino acid sequence of SEQ ID NO: 27,
light chain CDR1 comprising the amino acid sequence of SEQ ID NO: 33;
light chain CDR2 comprising the amino acid sequence of RAK; and
light chain CDR3 comprising the amino acid sequence of SEQ ID NO: 47,
(ix) an antibody comprising
heavy chain CDR1 comprising the amino acid sequence of SEQ ID NO: 5;
heavy chain CDR2 comprising the amino acid sequence of SEQ ID NO: 19;
heavy chain CDR3 comprising an amino acid sequence of SEQ ID NO: 25 or 24,
light chain CDR1 comprising the amino acid sequence of SEQ ID NO: 34;
light chain CDR2 comprising the amino acid sequence of GAK; and
light chain CDR3 comprising the amino acid sequence of SEQ ID NO: 46, and
(x) an antibody comprising
heavy chain CDR1 comprising the amino acid sequence of SEQ ID NO: 11;
heavy chain CDR2 comprising the amino acid sequence of SEQ ID NO: 20;
heavy chain CDR3 comprising the amino acid sequence of SEQ ID NO: 28,
light chain CDR1 comprising the amino acid sequence of SEQ ID NO: 35;
light chain CDR2 comprising the amino acid sequence of TAS; and
light chain CDR3 comprising the amino acid sequence of SEQ ID NO: 48.

4. The antibody or a fragment thereof according to claim 3, further comprising a sequence region adjacent to the C-terminus of the light chain CDR2, the sequence region comprising an amino acid sequence represented by formula (E-2-1) or (E-2-2):

$$SLX^{E61}S \quad (E\text{-}2\text{-}1)$$

or $$X^{E42}X^{E52}X^{E62}X^{E72} \quad (E\text{-}2\text{-}2)$$

wherein
$X^{E61}$ is A or P,
$X^{E42}$ is R, N, Y, or T,
$X^{E52}$ is L or R,
$X^{E62}$ is A or Y, and
$X^{E72}$ is S or T.

5. The antibody or a fragment thereof according to claim 1, wherein the antibody specifically binds to a 5' to 3' exonuclease domain of Taq polymerase.

6. The antibody or a fragment thereof according to claim 1, wherein the antibody specifically binds to a 5' to 3' exonuclease domain of Tth polymerase.

7. The antibody or a fragment thereof according to claim 1, wherein the antibody specifically binds to a 5' to 3' exonuclease domain of Z05 polymerase.

8. The antibody or a fragment thereof according to claim 1, wherein the antibody is any of the following:
(i) an antibody comprising
heavy chain CDR1 comprising the amino acid sequence of SEQ ID NO: 4;
heavy chain CDR2 comprising the amino acid sequence of SEQ ID NO: 12;
heavy chain CDR3 comprising the amino acid sequence of SEQ ID NO: 21;
light chain CDR1 comprising the amino acid sequence of SEQ ID NO: 29;
light chain CDR2 comprising the amino acid sequence of YTN; and
light chain CDR3 comprising the amino acid sequence of SEQ ID NO: 42,
(ii) an antibody comprising
heavy chain CDR1 comprising the amino acid sequence of SEQ ID NO: 5;
heavy chain CDR2 comprising the amino acid sequence of SEQ ID NO: 13;
heavy chain CDR3 comprising the amino acid sequence of SEQ ID NO: 22;
light chain CDR1 comprising the amino acid sequence of SEQ ID NO: 30;
light chain CDR2 comprising the amino acid sequence of YTD; and
light chain CDR3 comprising the amino acid sequence of SEQ ID NO: 43,
(iii) an antibody comprising
heavy chain CDR1 comprising the amino acid sequence of SEQ ID NO: 6;
heavy chain CDR2 comprising the amino acid sequence of SEQ ID NO: 14;
heavy chain CDR3 comprising the amino acid sequence of SEQ ID NO: 23;
light chain CDR1 comprising the amino acid sequence of SEQ ID NO: 31;
light chain CDR2 comprising the amino acid sequence of YAD; and
light chain CDR3 comprising the amino acid sequence of SEQ ID NO: 43,
(iv) an antibody comprising
heavy chain CDR1 comprising the amino acid sequence of SEQ ID NO: 7;
heavy chain CDR2 comprising the amino acid sequence of SEQ ID NO: 15;
heavy chain CDR3 comprising the amino acid sequence of SEQ ID NO: 22;
light chain CDR1 comprising the amino acid sequence of SEQ ID NO: 31;
light chain CDR2 comprising the amino acid sequence of YAN; and
light chain CDR3 comprising the amino acid sequence of SEQ ID NO: 44,
(v) an antibody comprising
heavy chain CDR1 comprising the amino acid sequence of SEQ ID NO: 5;

heavy chain CDR2 comprising the amino acid sequence of SEQ ID NO: 13;
heavy chain CDR3 comprising the amino acid sequence of SEQ ID NO: 22;
light chain CDR1 comprising the amino acid sequence of SEQ ID NO: 31;
light chain CDR2 comprising the amino acid sequence of YAN; and
light chain CDR3 comprising the amino acid sequence of SEQ ID NO: 43,
(vi) an antibody comprising
heavy chain CDR1 comprising the amino acid sequence of SEQ ID NO: 8;
heavy chain CDR2 comprising the amino acid sequence of SEQ ID NO: 16;
heavy chain CDR3 comprising the amino acid sequence of SEQ ID NO: 26;
light chain CDR1 comprising the amino acid sequence of SEQ ID NO: 32;
light chain CDR2 comprising the amino acid sequence of DAS; and
light chain CDR3 comprising the amino acid sequence of SEQ ID NO: 45,
(vii) an antibody comprising
heavy chain CDR1 comprising the amino acid sequence of SEQ ID NO: 9;
heavy chain CDR2 comprising the amino acid sequence of SEQ ID NO: 17;
heavy chain CDR3 comprising the amino acid sequence of SEQ ID NO: 24,
light chain CDR1 comprising the amino acid sequence of SEQ ID NO: 33;
light chain CDR2 comprising the amino acid sequence of GVK; and
light chain CDR3 comprising the amino acid sequence of SEQ ID NO: 46,
(viii) an antibody comprising
heavy chain CDR1 comprising the amino acid sequence of SEQ ID NO: 10;
heavy chain CDR2 comprising the amino acid sequence of SEQ ID NO: 18;
heavy chain CDR3 comprising the amino acid sequence of SEQ ID NO: 27,
light chain CDR1 comprising the amino acid sequence of SEQ ID NO: 33;
light chain CDR2 comprising the amino acid sequence of RAK; and
light chain CDR3 comprising the amino acid sequence of SEQ ID NO: 47,
(ix) an antibody comprising
heavy chain CDR1 comprising the amino acid sequence of SEQ ID NO: 5;
heavy chain CDR2 comprising the amino acid sequence of SEQ ID NO: 19;
heavy chain CDR3 comprising the amino acid sequence of SEQ ID NO: 25,
light chain CDR1 comprising the amino acid sequence of SEQ ID NO: 34;
light chain CDR2 comprising the amino acid sequence of GAK; and
light chain CDR3 comprising the amino acid sequence of SEQ ID NO: 46, and
(x) an antibody comprising
heavy chain CDR1 comprising the amino acid sequence of SEQ ID NO: 11;
heavy chain CDR2 comprising the amino acid sequence of SEQ ID NO: 20;
heavy chain CDR3 comprising the amino acid sequence of SEQ ID NO: 28,
light chain CDR1 comprising the amino acid sequence of SEQ ID NO: 35;
light chain CDR2 comprising the amino acid sequence of TAS; and
light chain CDR3 comprising the amino acid sequence of SEQ ID NO: 48.

9. The antibody or a fragment thereof according to claim 8, further comprising a sequence region adjacent to the C-terminus of the light chain CDR2, the sequence region comprising the amino acid sequence of any one of SEQ ID NOs: 36 to 41, or an amino acid sequence in which one to three amino acids are mutated in any one of these amino acid sequences.

10. The antibody or a fragment thereof according to claim 8, further comprising a sequence region adjacent to the C-terminus of the light chain CDR2, the sequence region comprising the amino acid sequence of any one of SEQ ID NOs: 36 to 41.

* * * * *